(12) United States Patent
Perez-Villar et al.

(10) Patent No.: US 7,667,003 B2
(45) Date of Patent: Feb. 23, 2010

(54) ANTIBODY DIRECTED TO HUMAN MIST (MAST CELL IMMUNORECEPTOR SIGNAL TRANSDUCER)

(75) Inventors: Juan J. Perez-Villar, Valencia (ES); Han Chang, Princeton Junction, NJ (US); Steven B. Kanner, Santa Monica, CA (US); Gena S. Whitney, Lawrenceville, NJ (US); Yuli Wu, Newtown, PA (US); Wen-Pin Yang, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/231,623

(22) Filed: Sep. 4, 2008

(65) Prior Publication Data
US 2009/0042226 A1 Feb. 12, 2009

Related U.S. Application Data

(62) Division of application No. 11/640,775, filed on Dec. 18, 2006, now Pat. No. 7,442,770.

(51) Int. Cl.
C07K 16/28 (2006.01)
(52) U.S. Cl. ............ 530/387.9; 530/388.1; 530/388.15; 435/810
(58) Field of Classification Search .................. None
See application file for complete search history.

(56) References Cited

U.S. PATENT DOCUMENTS

| 6,831,151 B1 | 12/2004 | Goitsuka |
|---|---|---|
| 6,943,241 B2 | 9/2005 | Isogai et al. |

FOREIGN PATENT DOCUMENTS

| EP | 1033401 | 9/2000 |
|---|---|---|
| EP | 1308459 A2 | 5/2003 |
| JP | 3146204 | 6/1991 |
| JP | 2005257347 | 9/2005 |
| WO | WO 01/21788 A1 | 3/2001 |
| WO | 1 132 468 A1 | 9/2001 |

OTHER PUBLICATIONS

Bolton, et al., "The Labelling of Proteins to High Specific Radioactivities by Conjugation to a$^{125}$I-Containing Acylating Agent", Biochem. J., vol. 133, pp. 529-539 (1973).
Lowenstei, et al., The SH2 and SH3 Domain-Containing Protein GRB2 Links Receptor Tyrosine Kinases to ras Signaling, Cell, vol. 70, pp. 431-442 (1992).
Lupher, et al., "The Cbl protooncoprotein: a negative regulator of immune receptor signal transduction", Immunology Today, vol. 20(8), pp. 375-382 (1999).
Polayes, et al., "New Baculovirus Expression Vectors for the Purification of Recombinant Proteins from Insect Cells", Focus, vol. 18(1), pp. 10-13 (1996).
Zhang, et al., "LAT: The Zap-70 Tyrosine Kinase Substrate that Links T Cell Receptor to Cellular Activation", Cell, vol. 92, pp. 83-92 (1998).
Mikayama, et al., "Molecular cloning and functional expression of a cDNA encoding glycosylation-inhibiting factor", PNAS, vol. 90 (21), pp. 10056-10060 (1993).
Voet, et al., Biochemistry, John Wiley & Sons, Inc., pp. 126-128 and 228-234.
NCBI Entrez Accession No. AB032369 (gi:8099156), Goitsuka, et al., May 26, 2000.
NCBI Entrez Accession No. BAA96241 (gi:8099157), Goitsuka, et al., May 26, 2000.
Goitsuka, R., J. of Clin. and Exp. Med., 192:1027-1031 (2000).
NCBI Entrez Accession No. gi:8099157.
Goitsuka et al. Int. Immunol. 12(4):573-580 (2000).
Cao et al., J. Exp. Med. 190:1527-1534 (1999).
Bateman, et al., "The Pfam Protein Families Database", Nucl. Acids Res., vol. 28 (1), pp. 263-266 (2000).
Downward, Julian, "The GRB2/Sem-5 adaptor protein", FEBS Letters, vol. 338, pp. 113-117 (1994).
Gout, et al., "The GTPase Dynamin Binds to and Is Activated by a Subset of SH3 Domains", Cell, vol. 75, pp. 25-36 (1993).
Hochuli, et al., "New Metal Chelate Adsorbent Selective For Proteins And Peptides Containing Neighbouring Histidine Residues", J. Chromatography, vol. 411, pp. 177-184 (1987).
Jackman, et al., Molecular Cloning of SLP-76, a 76-kDa Tyrosine Phosphoprotein Associated with Grb2 In T Cells, J. Biol. Chem., vol. 270(13), pp. 7029-7032 (1995).
Gilliland, et al., "Lymphocyte Lineage-restricted Tyrosine-phosphorylated Proteins That Bind PLCγ1 SH2 Domains", J. Biol. Chem., vol. 267(19), pp. 13610-13616 (1992).
Luckow, et al., "Efficient Generation of Infectious Recombinant Baculoviruses by Site-Specific Transposon-Mediated Insertion of Foreign Genes into a Baculovirus Genome Propagated in *Escherichia coli*", J. Virology, vol. 67(8), pp. 4566-4579 (1993).
Motto, et al., "In Vivo Association of Grb2 with pp116, a Substrate of the T Cell Antigen Receptor-activated Protein Tyrosine Kinase", J. Biol. Chem., vol. 269(34), pp. 21608-21613 (1994).

(Continued)

Primary Examiner—Prema Mertz
(74) Attorney, Agent, or Firm—Stephen C. D'Amico

(57) ABSTRACT

The present invention describes a newly discovered full-length polynucleotide encoding an SH2 domain-containing adapter protein, called human MIST, cloned, isolated and identified from a human spleen cDNA library. Also described are the MIST polypeptide sequence, expression vectors, host cells, agonists, antagonists, antisense molecules, and antibodies related to the polynucleotide and/or polypeptide of the present invention. Novel splice variant forms of human MIST are provided. Methods for screening for modulators, particularly inhibitors, of the MIST protein and use of the human MIST polynucleotide and polypeptide for therapeutics and diagnostics are described.

25 Claims, 21 Drawing Sheets

OTHER PUBLICATIONS

Myung, et al., "Adapter proteins in lymphocyte artigen-receptor signaling", Curr. Opin. Immunol., vol. 12, pp. 256-266 (2000).
O'Shea, et al., "Activation of human peripheral blood T lymphocytes by pharmacological induction of protein-tyrosine phosphorylation", PNAS, vol. 89, pp. 10306-10310 (1992).
Reif, et al., "SH3 Domains of the Adapter Molecule Grb2 Complex with Two Proteins in T Cells: The Guanine Nucleotide Exchange Protein Sos and a 75-kDa Protein That Is a Substrate for T Cell Antigen Receptor-activated Tyrosine Kinases", J. Biol. Chem., vol. 269(19), pp. 14081-14087 (1994).
Ren, et. al., "Abl protein-tyrosine kinase selects the Crk adapter as a substrate using SH3-binding sites", Genes Develop., vol. 8, pp. 783-795 (1994).
Schrelber, S.L., "Immunophilin-Sensitive Protein Phosphatase Action in Cell Signaling Pathways", Cell, vol. 70, pp. 365-368 (1992).
Tagle, et al., "Magnetic bead capture of expressed sequences encoded within large genomic segments", Nature, vol. 361, pp. 751-753 (1993).
Tirona, et al., "Polymorphisms in OATP-C", J. Biol. Chem., vol. 276(38), pp. 35669-35675 (2001).
Tuosto, et al., "$p95^{vav}$ Associates with Tyosine-phosphorylated SLP-76 in Antigen-stimulated T Cells", J. Exp. Med., vol. 184, pp. 1161-1166 (1996).
Heeke, et al., "Expression of Human Asparagine Synthetase In *Escherichia coli*", J. Biol. Chem., vol. 264, (10), pp. 5503-5509 (1989).
Watanabe, et. al., "Four Tyrosine Residues in Phospholipase C-$\gamma$2, Identified as Btk-dependent Phosphorylation Sites, Are Required for B Cell Antigen Receptor-coupled Calcium Signaling", J. Biol. Chem., vol. 276(42), pp. 38595-38601 (2001).
Wu, et al., "Vav and SLP-76 Interact and Functionally Cooperate in IL-2 Gene Activation", Immunity, vol. 4, pp. 593-602 (1996).
Ye, et. al., "Binding of Vav to Grb2 through dimerization of Src homology 3 domains", PNAS, vol. 91, pp. 12629-12633 (1994).
NCBI Entrez Accession No. AA166259 (gi:1744240), Marra M/Mouse Est Project, Dec. 19, 1996.
NCBI Entrez Accession No. AAW20767 (gi:56674094), Goitsuka, R, Dec. 15, 2004.
NCBI Entrez Accession No. ABA67702 (gi:77369954), Isogai, et al., Oct. 7, 2005.
NCBI Entrez Accession No. AF187819 (gi:6492365), Cao, et al., Dec. 1, 1999.
NCBI Entrez Accession No. BAC76765 (gi:30984140), Goitsuka, R., May 22, 2003.
NCBI Entrez Accession No. NP_443196 (gi:42734366), Goitsuka, et al., Nov. 29, 2005.
NCBI Entrez Accession No. XM_093920 (gi:42657102), NCBI Annotation Process, Feb. 19, 2004.
NCBI Entrez Accession No. NM_052964 (gi:42734365), Goitsuka, et al., Nov. 29, 2005.
NCBI Entrez Accession No. NP_443196 (gi:42734366), Goitsuka, et al., Nov. 29, 2005.
NCBI Entrez Accession No. XP_093920 (gi:27477858), NCBI's Annotation Process, Feb. 19, 2004.
NCBI Entrez Accession No. XP_520687 (gi:55666927), NCBI's Annotation Process, Nov. 10, 2004.
NCBI Entrez Accession No. XM_093920 (gi:37540655), NCBI's Annotation Process, Oct. 17, 2003.
Swiss-Prot Accession No. Q9P2U9, Integrated Oct. 1, 2001, Annotations modified on May 30, 20064.

FIG. 1A

```
   1 CCTAGAGCCAGCAGAGTCCAGGCTGCTGTTAACAACTTCATGTCCCCGTGGGTAGCAGGC   60
  61 AGGTGCTTCTGTCTGATCTGGCTCTCCTTGACCACTGTACTCATCAAATAGACCAAGATC  120
 121 CCCAGAGTCCAAGATCCTTACAAGGGGCCAGAAAGGGATGAGCTTTCTGAAGAAGCACT  180
 181 GATGTAAAATACCAGGAATTTTGACATCGAAGAAGATTTTTGTGATGGCAGCTGGGATTT  240
 241 GGCCATAATCTAGAAGACACATGGTGAATACAGTTGCAAGTCATTTAGTCATATTTCTTG  300
 301 CTAAATTGCTGTGTCTTCAATGGCTGAATTGAAGATCCCTCTTACCCGCCAGGTGCCAAG  360
 361 AACTATGAACAGGCAGGGCAATAGAAAGACAACTAAAGAAGGATCCAACGATTTGAAATT  420
 421 CCAGAACTTCAGTCTGCCAAAAAACAGGTCATGGCCTCGCATCAATAGTGCCACAGGCCA  480
 481 GTACCAGAGGATGAACAAGCCTCTTCTAGACTGGGAAAGAAACTTTGCTGCAGTCCTGGA  540
 541 TGGAGCAAAAGGCCACAGTGATGATGACTATGATGACCCTGAGCTTCGGATGGAAGAGAC  600
 601 ATGGCAGTCGATTAAAATTTTACCAGCCCGGCCTATAAAGGAATCTGAATATGCAGATAC  660
 661 ACACTATTTCAAGGTTGCAATGGACACTCCCCTTCCGTTAGACACCAGGACCTCTATCTC  720
 721 CATTGGACAGCCGACCTGGAACACACAGACGAGGTTGGAAAGAGTGGACAAACCCATTTC  780
 781 CAAGGACGTCAGAAGCCAAAACATTAAAGGAGATGCATCCGTAAGAAAGAACAAGATTCC  840
 841 TTTACCACCTCCTCGGCCTCTCATAACACTTCCGAAGAAGTACCAACCCTTGCCCCCTGA  900
 901 GCCGGAGAGCAGCAGGCCACCTTTATCTCAGAGACACACCTTTCCAGAAGTCCAGAGAAT  960
 961 GCCCAGTCAGATAAGCTTAAGGGACTTAAGTGAGGTCCTTGAAGCAGAAAAAGTTCCTCA 1020
1021 TAACCAGAGGAAGCCTGAATCAACTCATCTGTTAGAAAACCAAAATACTCAAGAGATTCC 1080
1081 ACTTGCCATTAGCAGTTCTTCATTCACGACAAGCAACCACAGTGTGCAAAACAGAGATCA 1140
1141 TAGAGGAGGCATGCAGCCCTGTTCTCCTCAGAGATGCCAGCCTCCAGCCAGCTGCAGCCC 1200
1201 TCACGAAAATATACTGCCCTATAAATACACAAGCTGGAGACCACCTTTCCCCAAAAGGTC 1260
1261 TGATAGAAAGGATGTCCAGCACAATGAATGGTACATTGGAGAATACAGCCGCCAGGCAGT 1320
1321 GGAAGAGGCATTCATGAAGGAGAACAAGGATGGTAGTTTCTTGGTCCGAGATTGTTCCAC 1380
1381 AAAATCCAAGGAAGAGCCCTATGTTTTGGCTGTGTTTTATGAGAACAAAGTCTACAATGT 1440
1441 AAAAATCCGCTTCCTGGAGAGGAATCAGCAGTTTGCCCTGGGGACAGGACTCAGAGGAGA 1500
```

FIG. 1B

```
1501 TGAGAAGTTTGATTCAGTAGAAGACATCATCGAACACTACAAGAATTTTCCCATTATACT 1560
1561 AATTGATGGGAAAGATAAAACTGGGGTCCACAGGAAACAGTGTCACCTCACTCAGCCACT 1620
1621 CCCTCTCACCAGACACCTCTTGCCTCTGTAGCCTGGTCTTTGTGTTATCTTTGGTTTACT 1680
1681 GGATTCAGCGCTTCCATTGTTTTCATTGATTTCAAAAGTTTATTTTCTGTGCCTTCAAGG 1740
1741 GACAACTTTTTTAACTTTGGAGAAAAGAAAAACACTCTATAACAGAGAGTGGAAAATCAC 1800
1801 TCACGGTTTTGAAAGTTCAAACCACAGAGAAATATTTATAACATGCAAAA            1851
```

```
   1  CCTAGAGCCAGCAGAGTCCAGGCTGCTGTTAACAACTTCATGTCCCCGTGGGTAGCAGGC    60

61  AGGTGCTTCTGTCTGATCTGGCTCTCCTTGACCACTGTACTCATCAAATAGACCAAGATC   120

121  CCCAGAGTCCAAGATCCTTACAAGGGGGCCAGAAAGGGATGAGCTTTCTGAAGAAGCACT   180

181  GATGTAAAATACCAGGAATTTTGACATCGAAGAAGATTTTTGTGATGGCAGCTGGGATTT   240

241  GGCCATAATCTAGAAGACACATGGTGAATACAGTTGCAAGTCATTTAGTCATATTTCTTG   300

301  CTAAATTGCTGTGTCTTCAATGGCTGAATTGAAGATCCCTCTTACCCGCCAGGTGCCAAG   360
   1                    M  A  E  L  K  I  P  L  T  R  Q  V  P  R    14

361  AACTATGAACAGGCAGGGCAATAGAAAGACAACTAAAGAAGGATCCAACGATTTGAAATT   420
  15   T  M  N  R  Q  G  N  R  K  T  T  K  E  G  S  N  D  L  K  F   34

421  CCAGAACTTCAGTCTGCCAAAAAACAGGTCATGGCCTCGCATCAATAGTGCCACAGGCCA   480
  35   Q  N  F  S  L  P  K  N  R  S  W  P  R  I  N  S  A  T  G  Q   54

481  GTACCAGAGGATGAACAAGCCTCTTCTAGACTGGGAAAGAAACTTTGCTGCAGTCCTGGA   540
  55   Y  Q  R  M  N  K  P  L  L  D  W  E  R  N  F  A  A  V  L  D   74

541  TGGAGCAAAAGGCCACAGTGATGATGACTATGATGACCCTGAGCTTCGGATGGAAGAGAC   600
  75   G  A  K  G  H  S  D  D  D  Y  D  D  P  E  L  R  M  E  E  T   94
                                    ↑

601  ATGGCAGTCGATTAAAATTTTACCAGCCCGGCCTATAAAGGAATCTGAATATGCAGATAC   660
  95   W  Q  S  I  K  I  L  P  A  R  P  I  K  E  S  E  Y  A  D  T  114
                                                          ↑

661  ACACTATTTCAAGGTTGCAATGGACACTCCCCTTCCGTTAGACACCAGGACCTCTATCTC   720
 115   H  Y  F  K  V  A  M  D  T  P  L  P  L  D  T  R  T  S  I  S  134

721  CATTGGACAGCCGACCTGGAACACACAGACGAGGTTGGAAAGAGTGGACAAACCCATTTC   780
 135   I  G  Q  P  T  W  N  T  Q  T  R  L  E  R  V  D  K  P  I  S  154

781  CAAGGACGTCAGAAGCCAAAACATTAAAGGAGATGCATCCGTAAGAAAGAACAAGATTCC   840
 155   K  D  V  R  S  Q  N  I  K  G  D  A  S  V  R  K  N  K  I  *P*  174

841  TTTACCACCTCCTCGGCCTCTCATAACACTTCCGAAGAAGTACCAACCCTTGCCCCCTGA   900
 175  *L  P  P  P  R*  P  L  I  T  L  P  K  K  Y  Q  *P  L  P  P  E*  194

901  GCCGGAGAGCAGCAGGCCACCTTTATCTCAGAGACACACCTTTCCAGAAGTCCAGAGAAT   960
 195  *P  E  S  S  R  P  P  L  S  Q  R  H  T  F  P  E  V  Q  R*  M  214

961  GCCCAGTCAGATAAGCTTAAGGGACTTAAGTGAGGTCCTTGAAGCAGAAAAAGTTCCTCA  1020
 215   P  S  Q  I  S  L  R  D  L  S  E  V  L  E  A  E  K  V  P  H  234

1021  TAACCAGAGGAAGCCTGAATCAACTCATCTGTTAGAAAACCAAAATACTCAAGAGATTCC  1080
 235   N  Q  R  K  P  E  S  T  H  L  L  E  N  Q  N  T  Q  E  I  P  254

1081  ACTTGCCATTAGCAGTTCTTCATTCACGACAAGCAACCACAGTGTGCAAAACAGAGATCA  1140
 255   L  A  I  S  S  S  S  F  T  T  S  N  H  S  V  Q  N  R  D  H  274

1141  TAGAGGAGGCATGCAGCCCTGTTCTCCTCAGAGATGCCAGCCTCCAGCCAGCTGCAGCCC  1200
 275   R  G  G  M  Q  P  C  S  P  Q  R  C  Q  P  P  A  S  C  S  P  294
```

FIG. 3B

```
1201  TCACGAAAATATACTGCCCTATAAATACACAAGCTGGAGACCACCTTTCCCCAAAAGGTC  1260
 295   H   E   N   I   L   P   Y   K   Y   T   S   W   R   P   P   F   P   K   R   S    314

1261  TGATAGAAAGGATGTCCAGCACAATGAATGGTACATTGGAGAATACAGCCGCCAGGCAGT  1320
 315   D   R   K   D   V   Q   H   N   E   W   Y   I   G   E   Y   S   R   Q   A   V    334

1321  GGAAGAGGCATTCATGAAGGAGAACAAGGATGGTAGTTTCTTGGTCCGAGATTGTTCCAC  1380
 335   E   E   A   F   M   K   E   N   K   D   G   S   F   L   V   R   D   C   S   T    354

1381  AAAATCCAAGGAAGAGCCCTATGTTTTGGCTGTGTTTTATGAGAACAAAGTCTACAATGT  1440
 355   K   S   K   E   E   P   Y   V   L   A   V   F   Y   E   N   K   V   Y   N   V    374

1441  AAAAATCCGCTTCCTGGAGAGGAATCAGCAGTTTGCCCTGGGGACAGGACTCAGAGGAGA  1500
 375   K   I   R   F   L   E   R   N   Q   Q   F   A   L   G   T   G   L   R   G   D    394

1501  TGAGAAGTTTGATTCAGTAGAAGACATCATCGAACACTACAAGAATTTTCCCATTATACT  1560
 395   E   K   F   D   S   V   E   D   I   I   E   H   Y   K   N   F   P   I   I   L    414

1561  AATTGATGGGAAAGATAAAACTGGGGTCCACAGGAAACAGTGTCACCTCACTCAGCCACT  1620
 415   I   D   G   K   D   K   T   G   V   H   R   K   Q   C   H   L   T   Q   P   L    434

1621  CCCTCTCACCAGACACCTCTTGCCTCTGTAGCCTGGTCTTTGTGTTATCTTTGGTTTACT  1680
 435   P   L   T   R   H   L   L   P   L   *                                             444

1681  GGATTCAGCGCTTCCATTGTTTTCATTGATTTCAAAAGTTTATTTTCTGTGCCTTCAAGG  1740

1741  GACAACTTTTTTAACTTTGGAGAAAAGAAAAACACTCTATAACAGAGAGTGGAAAATCAC  1800

1801  TCACGGTTTTGAAAGTTCAAACCACAGAGAAAATATTTATAACATGCAAAA           1851
```

FIG. 4A

```
   1  GTCAGACCTCTCAGGTCTGTGGCTGCATTTCACAGGAAACCAAGTCTAAAACGGACCTAT    60
  61  CAGGAGGTTTTCTGCTGAAGGGCACTGCTTAGCATCGAGAAGAATTCAACCCACCGCCTT   120
 121  ACTAATTTCCAGTGCCCCAAGGTCTCTGCACTGCCGCCCCTCCTCACAGGAGACGGACAC   180
 181  CTCAGCCTAGATCCCTTGGTGCTCTCCACGCTGTTCAGGCTGAATTGAAGATCCCTCTTA   240
 241  CCCGCCAGGTGCCAAGAACTATGAACAGGCAGGGCAATAGAAAGACAACTAAAGAAGGAT   300
 301  CCAACGATTTGAAATTCCAGAACTTCAGTCTGCCAAAAAACAGGTCATGGCCTCGCATCA   360
 361  ATAGTGCCACAGGCCAGTACCAGAGGATGAACAAGCCTCTTCTAGACTGGGAAAGAAACT   420
 421  TTGCTGCAGTCCTGGATGGAGCAAAAGGCCACAGTGATGATGACTATGATGACCCTGAGC   480
 481  TTCGGATGGAAGAGACATGGCAGTCGATTAAAATTTTACCAGCCCGGCCTATAAAGGAAT   540
 541  CTGAATATGCAGATACACACTATTTCAAGGTTGCAATGGACACTCCCCTTCCGTTAGACA   600
 601  CCAGGACCTCTATCTCCATTGGACAGCCGACCTGGAACACACAGACGAGGTTGGAAAGAG   660
 661  TGGACAAACCCATTTCCAAGGACGTCAGAAGCCAAAACATTAAAGGAGATGCATCCGTAA   720
 721  GAAAGAACAAGATTCCTTTACCACCTCCTCGGCCTCTCATAACACTTCCGAAGAAGTACC   780
 781  AACCCTTGCCCCCTGAGCCGGAGAGCAGCAGGCCACCTTTATCTCAGAGACACACCTTTC   840
 841  CAGAAGTCCAGAGAATGCCCAGTCAGATAAGCTTAAGGGACTTAAGTGAGGTCCTTGAAG   900
 901  CAGAAAAGTTCCTCATAACCAGAGGAAGCCTGAATCAACTCATCTGTTAGAAAACCAAA   960
 961  ATACTCAAGAGATTCCACTTGCCATTAGCAGTTCTTCATTCACGACAAGCAACCACAGTG  1020
1021  TGCAAAACAGAGATCATAGAGGAGGCATGCAGCCCTGTTCTCCTCAGAGATGCCAGCCTC  1080
1081  CAGCCAGCTGCAGCCCTCACGAAAATATACTGCCCTATAAATACACAAGCTGGAGACCAC  1140
1141  CTTTCCCCAAAAGGTCTGATAGAAAGGATGTCCAGCACAATGAATGGTACATTGGAGAAT  1200
1201  ACAGCCGCCAGGCAGTGGAAGAGGCATTCATGAAGGAGAACAAGGATGGTAGTTTCTTGG  1260
1261  TCCGAGATTGTTCCACAAAATCCAAGGAAGAGCCCTATGTTTTGGCTGTGTTTTATGAGA  1320
1321  ACAAAGTCTACAATGTAAAAATCCGCTTCCTGGAGAGGAATCAGCAGTTTGCCCTGGGGA  1380
1381  CAGGACTCAGAGGAGATGAGAAGTTTGATTCAGTAGAAGACATCATCGAACACTACAAGA  1440
1441  ATTTTCCCATTATACTAATTGATGGGAAAGATAAAACTGGGGTCCACAGGAAACAGTGTC  1500
1501  ACCTCACTCAGCCACTCCCTCTCACCAGACACCTCTTGCCTCTGTAGCCTGGTCTTTGTG  1560
1561  TTATCTTTGGTTTACTGGATTCAGCGCTTCCATTGTTTTCATTGATTTCAAAAGTTTATT  1620
```

FIG. 4B

```
1621  TTCTGTGCCTTCAAGGGACAACTTTTTTAACTTTGGAGAAAAGAAAAACACTCTATAACA  1680
1681  GAGAGTGGAAAATCACTCACGGTTTTGAAAGTTCAAACCACAGAGAAAATATTTATAACA  1740
1741  TGCAAAAAATAAAAACATTCTAGTAACTGGCCACTGGAAAATAAATAAAAATAAAAACTA  1800
1801  GGGTTTTAAAAGTATCTTCTAAAAAACAACAACAAAAAATACTATAAACATAGCCATTAT  1860
1861  GCTCATGATACAGGCGAGCAGCAAAGGGCACCAGAAGCTGTTGCTTAAATGTTTGCAGTC  1920
1921  AGTGCAAGACAAGTCTATGGGAAATTCCCAAATCTGTGCTCTTTACAGGACACTGCGCTG  1980
1981  CCTTTATGTCAGTTGTTGGGCCTTACATATATACAATGTGTGGATGATTTCTTACACTAA  2040
2041  AGATGCTGGGCTGGGTGCGGTGCCTCATGCCTGTAATCCCAGCACTTTGGGAGGCTGAGG  2100
2101  TGGACAGATCACGAGGTCAGGAGATCAAGACCATCCTGGCTAACATGGTGAAACCCCATG  2160
2161  TCTACTAAAAATACAAAAAATCAGCTGGGCGTGGTGGTGGGTGCCTGTAGTCCCAGCTAC  2220
2221  TCGGGAGGCTGAGGCAGGAGAATGGTGTGAACCCGGGAGGCGGAGCTTGCAGTGAGCCGA  2280
2281  AATCGCGCCACTGCACTCCAATCCAGCCTGGGGACAGAGAGACTCCGTCTCAAAA       2335
```

```
   1 GTCAGACCTCTCAGGTCTGTGGCTGCATTTCACAGGAAACCAAGTCTAAAACGGACCTAT   60

61 CAGGAGGTTTTCTGCTGAAGGGCACTGCTTAGCATCGAGAAGAATTCAACCCACCGCCTT  120

121 ACTAATTTCCAGTGCCCCAAGGTCTCTGCACTGCCGCCCCTCCTCACAGGAGACGGACAC  180

181 CTCAGCCTAGATCCCTTGGTGCTCTCCACGCTGTTCAGGCTGAATTGAAGATCCCTCTTA  240

241 CCCGCCAGGTGCCAAGAACTATGAACAGGCAGGGCAATAGAAAGACAACTAAAGAAGGAT  300
   1                   M  N  R  Q  G  N  R  K  T  T  K  E  G  S    14

301 CCAACGATTTGAAATTCCAGAACTTCAGTCTGCCAAAAAACAGGTCATGGCCTCGCATCA  360
  15  N  D  L  K  F  Q  N  F  S  L  P  K  N  R  S  W  P  R  I  N   34

361 ATAGTGCCACAGGCCAGTACCAGAGGATGAACAAGCCTCTTCTAGACTGGGAAAGAAACT  420
  35  S  A  T  G  Q  Y  Q  R  M  N  K  P  L  L  D  W  E  R  N  F   54

421 TTGCTGCAGTCCTGGATGGAGCAAAAGGCCACAGTGATGATGACTATGATGACCCTGAGC  480
  55  A  A  V  L  D  G  A  K  G  H  S  D  D  D  Y  D  D  P  E  L   74

481 TTCGGATGGAAGAGACATGGCAGTCGATTAAAATTTTACCAGCCCGGCCTATAAAGGAAT  540
  75  R  M  E  E  T  W  Q  S  I  K  I  L  P  A  R  P  I  K  E  S   94

541 CTGAATATGCAGATACACACTATTTCAAGGTTGCAATGGACACTCCCCTTCCGTTAGACA  600
  95  E  Y  A  D  T  H  Y  F  K  V  A  M  D  T  P  L  P  L  D  T  114

601 CCAGGACCTCTATCTCCATTGGACAGCCGACCTGGAACACACAGACGAGGTTGGAAAGAG  660
 115  R  T  S  I  S  I  G  Q  P  T  W  N  T  Q  T  R  L  E  R  V  134

661 TGGACAAACCCATTTCCAAGGACGTCAGAAGCCAAAACATTAAAGGAGATGCATCCGTAA  720
 135  D  K  P  I  S  K  D  V  R  S  Q  N  I  K  G  D  A  S  V  R  154

721 GAAAGAACAAGATTCCTTTACCACCTCCTCGGCCTCTCATAACACTTCCGAAGAAGTACC  780
 155  K  N  K  I  P  L  P  P  P  R  P  L  I  T  L  P  K  K  Y  Q  174

781 AACCCTTGCCCCCTGAGCCGGAGAGCAGCAGGCCACCTTTATCTCAGAGACACACCTTTC  840
 175  P  L  P  P  E  P  E  S  S  R  P  P  L  S  Q  R  H  T  F  P  194

841 CAGAAGTCCAGAGAATGCCCAGTCAGATAAGCTTAAGGGACTTAAGTGAGGTCCTTGAAG  900
 195  E  V  Q  R  M  P  S  Q  I  S  L  R  D  L  S  E  V  L  E  A  214

901 CAGAAAAAGTTCCTCATAACCAGAGGAAGCCTGAATCAACTCATCTGTTAGAAAACCAAA  960
 215  E  K  V  P  H  N  Q  R  K  P  E  S  T  H  L  L  E  N  Q  N  234

961 ATACTCAAGAGATTCCACTTGCCATTAGCAGTTCTTCATTCACGACAAGCAACCACAGTG 1020
 235  T  Q  E  I  P  L  A  I  S  S  S  S  F  T  T  S  N  H  S  V  254

1021 TGCAAAACAGAGATCATAGAGGAGGCATGCAGCCCTGTTCTCCTCAGAGATGCCAGCCTC 1080
 255  Q  N  R  D  H  R  G  G  M  Q  P  C  S  P  Q  R  C  Q  P  P  274

1081 CAGCCAGCTGCAGCCCTCACGAAAATATACTGCCCTATAAATACACAAGCTGGAGACCAC 1140
 275  A  S  C  S  P  H  E  N  I  L  P  Y  K  Y  T  S  W  R  P  P  294

1141 CTTTTCCCCAAAAGGTCTGATAGAAAGGATGTCCAGCACAATGAATGGTACATTGGAGAAT 1200
 295  F  P  K  R  S  D  R  K  D  V  Q  H  N  E  W  Y  I  G  E  Y  314
```

FIG. 6B

```
1201  ACAGCCGCCAGGCAGTGGAAGAGGCATTCATGAAGGAGAACAAGGATGGTAGTTTCTTGG  1260
 315    S  R  Q  A  V  E  E  A  F  M  K  E  N  K  D  G  S  F  L  V   334

1261  TCCGAGATTGTTCCACAAAATCCAAGGAAGAGCCCTATGTTTTGGCTGTGTTTTATGAGA  1320
 335    R  D  C  S  T  K  S  E  E  P  Y  V  L  A  V  F  Y  E  N      354

1321  ACAAAGTCTACAATGTAAAAATCCGCTTCCTGGAGAGGAATCAGCAGTTTGCCCTGGGGA  1380
 355    K  V  Y  N  V  K  I  R  F  L  E  R  N  Q  Q  F  A  L  G  T   374

1381  CAGGACTCAGAGGAGATGAGAAGTTTGATTCAGTAGAAGACATCATCGAACACTACAAGA  1440
 375    G  L  R  G  D  E  K  F  D  S  V  E  D  I  I  E  H  Y  K  N   394

1441  ATTTTCCCATTATACTAATTGATGGGAAAGATAAAACTGGGGTCCACAGGAAACAGTGTC  1500
 395    F  P  I  I  L  I  D  G  K  D  K  T  G  V  H  R  K  Q  C      414

1501  ACCTCACTCAGCCACTCCCTCTCACCAGACACCTCTTGCCTCTGTAGCCTGGTCTTTGTG  1560
 415    L  T  Q  P  L  P  L  T  R  H  L  P  L                         429

1561  TTATCTTTGGTTTACTGGATTCAGCGCTTCCATTGTTTTCATTGATTTCAAAAGTTTATT  1620

1621  TTCTGTGCCTTCAAGGGACAACTTTTTTAACTTTGGAGAAAAGAAAAACACTCTATAACA  1680

1681  GAGAGTGGAAAATCACTCACGGTTTTGAAAGTTCAAACCACAGAGAAATATTTATAACA   1740

1741  TGCAAAAAATAAAAACATTCTAGTAACTGGCCACTGGAAAATAAATAAAAATAAAAACTA  1800

1801  GGGTTTTAAAAGTATCTTCTAAAAAACAACAACAAAAAATACTATAAACATAGCCATTAT  1860

1861  GCTCATGATACAGGCGAGCAGCAAAGGGCACCAGAAGCTGTTGCTTAAATGTTTGCAGTC  1920

1921  AGTGCAAGACAAGTCTATGGGAAATTCCCAAATCTGTGCTCTTTACAGGACACTGCGCTG  1980

1981  CCTTTATGTCAGTTGTTGGGCCTTACATATATACAATGTGTGGATGATTTCTTACACTAA  2040

2041  AGATGCTGGGCTGGGTGCGGTGCCTCATGCCTGTAATCCCAGCACTTTGGGAGGCTGAGG  2100

2101  TGGACAGATCACGAGGTCAGGAGATCAAGACCATCCTGGCTAACATGGTGAAACCCCATG  2160

2161  TCTACTAAAAATACAAAAAATCAGCTGGGCGTGGTGGTGGGTGCCTGTAGTCCCAGCTAC  2220

2221  TCGGGAGGCTGAGGCAGGAGAATGGTGTGAACCCGGGAGGCGGAGCTTGCAGTGAGCCGA  2280

2281  AATCGCGCCACTGCACTCCAATCCAGCCTGGGGACAGAGAGACTCCGTCTCAAAA       2335
```

FIG. 7A

```
   1 GGCTGCTGTTAACAACTTCATGTCCCCGTGGGTAGCAGGCAGGTGCTTCTGTCTGATCTG   60
  61 GCTCTCCTTGACCACTGTACTCATCAAATAGACCAAGATCCCCAGAGTCCAAGATCCTTA  120
 121 CAAGGGGCCAGAAAGGGATGAGCTTTCTGAAGAAGCACTGATGTAAAATACCAGGAATT  180
 181 TTGACATCGAAGAAGATTTTGTGATGGCAGCTGGGATTTGGCCATAATCTAGAAGACAC  240
 241 ATGGTGAATACAGTTGCAAGTCATTTAGTCATATTTCTTGCTAAATTGCTGTGTCTTCAA  300
 301 TGGGGCAATAGAAAGACAACTAAAGAAGGATCCAACGATTTGAAATTCCAGAACTTCAGT  360
 361 CTGCCAAAAACAGGTCATGGCCTCGCATCAATAGTGCCACAGGCCAGTACCAGAGGATG  420
 421 AACAAGCCTCTTCTAGACTGGATTTGGCAGCTTGACCATTTATTATCGCACAGTGGATGC  480
 481 AATCAGAAGTCTGGGCACAGCATGGCTCAACTAGTTCCCCTGTTCTGGGTCTCACAAGAC  540
 541 TGAAAGCAACATGCTGGCAGGGCTGCATTCTCCTCCAGGGGCTCTGAAGAGGAACTTGCT  600
 601 TCCAGATTCTTTCAGGAAAGAAACTTTGCTGCAGTCCTGGATGGAGCAAAAGGCCACAGT  660
 661 GATGATGACTATGATGACCCTGAGCTTCGGATGGAAGAGACATGGCAGTCGATTAAAATT  720
 721 TTACCAGCCCGGCCTATAAAGGAATCTGAATATGCAGATACACACTATTTCAAGGTTGCA  780
 781 ATGGACACTCCCCTTCCGTTAGACACCAGGACCTCTATCTCCATTGGACAGCCGACCTGG  840
 841 AACACACAGACGAGGTTGGAAAGAGTGGACAAACCCATTTCCAAGGACGTCAGAAGCCAA  900
 901 AACATTAAAGGAGATGCATCCGTAAGAAAGAACAAGATTCCTTTACCACCTCCTCGGCCT  960
 961 CTCATAACACTTCCGAAGAAGTACCAACCCTTGCCCCTGAGCCGGAGAGCAGCAGGCCA 1020
1021 CCTTTATCTCAGAGACACACCTTTCCAGAAGTCCAGAGAATGCCCAGTCAGATAAGCTTA 1080
1081 AGGGACTTAAGTGAGGTCCTTGAAGCAGAAAAAGTTCCTCATAACCAGAGGAAGCCTGAA 1140
1141 TCAACTCATCTGTTAGAAAACCAAAATACTCAAGAGATTCCACTTGCCATTAGCAGTTCT 1200
1201 TCATTCACGACAAGCAACCACAGTGTGCAAAACAGAGATCATAGAGGAGGCATGCAGCCC 1260
1261 TGTTCTCCTCAGAGATGCCAGCCTCCAGCCAGCTGCAGCCCTCACGAAAATATACTGCCC 1320
1321 TATAAATACACAAGCTGGAGACCACCTTTCCCCAAAAGGTCTGATAGAAAGGATGTCCAG 1380
1381 CACAATGAATGGTACATTGGAGAATACAGCCGCCAGGCAGTGGAAGAGGCATTCATGAAG 1440
1441 GAGAACAAGGATGGTAGTTTCTTGGTCCGAGATTGTTCCACAAAATCCAAGGAAGAGCCC 1500
1501 TATGTTTTGGCTGTGTTTATGAGAACAAAGTCTACAATGTAAAAATCCGCTTCCTGGAG 1560
1561 AGGAATCAGCAGTTTGCCCTGGGGACAGGACTCAGAGGAGATGAGAAGTTTGATTCAGTA 1620
```

FIG. 7B

```
1621 GAAGACATCATCGAACACTACAAGAATTTTCCCATTATACTAATTGATGGGAAAGATAAA 1680
1681 ACTGGGGTCCACAGGAAACAGTGTCACCTCACTCAGCCACTCCCTCTCACCAGACACCTC 1740
1741 TTGCCTCTGTAGCCTGGTCTTTGTGTTATCTTTGGTTTACTGGATTCAGCGCTTCCATTG 1800
1801 TTTTCATTGATTTCAAAAGTTTATTTTCTGTGCCTTCAAGGGACAACTTTTTTAACTTTG 1860
1861 GAGAAAAGAAAAACACTCTATAACAGAGAGTGGAAAATCACTCACGGTTTTGAAAGTTCA 1920
1921 AACCACAGAGAAATATTTATAACATGCAAAAATAAAAACATTCTAGTAACTGGCCACT 1980
1981 GGAAAATAAATAAAAATAAAAACTAGGGTTTTAAAAGTATCTTCTAAAAAACAACAACAA 2040
2041 AAAATACTATAAACATAGCCATTATGCTCATGATACAGGCGAGCAGCAAAGGGCACCAGA 2100
2101 AGCTGTTGCTTAAATGTTTGCAGTCAGTGCAAGACAAGTCTATGGGAAATTCCCAAATCT 2160
2161 GTGCTCTTTACAGGACACTGCGCTGCCTTTATGTCAGTTGTTGGGCCTTACATATATACA 2220
2221 ATGTGTGGATGATTTCTTACACTAAAGATGCTGGGCTGGGTGCGGTGCCTCATGCCTGTA 2280
2281 ATCCCAGCACTTTGGGAGGCTGAGGTGGACAGATCACGAGGTCAGGAGATCAAGACCATC 2340
2341 CTGGCTAACATGGTGAAACCCCATGTCTACTAAAAATACAAAAAATCAGCTGGGCGTGGT 2400
2401 GGTGGGTGCCTGTAGTCCCAGCTACTCGGGAGGCTGAGGCAGGAGAATGGTGTGAACCCG 2460
2461 GGAGGCGGAGCTTGCAGTGAGCCGAAATCGCGCCACTGCACTCCAATCCAGCCTGGGGAC 2520
2521 AGAGAGACTCCGTCTCAAAA 2540
```

FIG. 8

|  |  |  |  |  |  |  |  |  |  |  |  |  |  |  |  |  |  |  |  |  |  |
|---|---|---|---|---|---|---|---|---|---|---|---|---|---|---|---|---|---|---|---|---|---|
| 1 |  |  |  |  |  |  |  |  |  | M | E | E | T | W | Q | S | I | K | I | 10 |
| 11 | L | P | A | R | P | I | K | E | S | E | Y | A | D | T | H | Y | F | K | V | A | 30 |
| 31 | M | D | T | P | L | P | L | D | T | R | T | S | I | S | I | G | Q | P | T | W | 50 |
| 51 | N | T | Q | T | R | L | E | R | V | D | K | P | I | S | K | D | V | R | S | Q | 70 |
| 71 | N | I | K | G | D | A | S | V | R | K | N | K | I | P | L | P | P | P | R | P | 90 |
| 91 | L | I | T | L | P | K | K | Y | Q | P | L | P | P | E | P | E | S | S | R | P | 110 |
| 111 | P | L | S | Q | R | H | T | F | P | E | V | Q | R | M | P | S | Q | I | S | L | 130 |
| 131 | R | D | L | S | E | V | L | E | A | E | K | V | P | H | N | Q | R | K | P | E | 150 |
| 151 | S | T | H | L | L | E | N | Q | N | T | Q | E | I | P | L | A | I | S | S | S | 170 |
| 171 | S | F | T | T | S | N | H | S | V | Q | N | R | D | H | R | G | G | M | Q | P | 190 |
| 191 | C | S | P | Q | R | C | Q | P | P | A | S | C | S | P | H | E | N | I | L | P | 210 |
| 211 | Y | K | Y | T | S | W | R | P | P | F | P | K | R | S | D | R | K | D | V | Q | 230 |
| 231 | H | N | E | W | Y | I | G | E | Y | S | R | Q | A | V | E | E | A | F | M | K | 250 |
| 251 | E | N | K | D | G | S | F | L | V | R | D | C | S | T | K | S | K | E | E | P | 270 |
| 271 | Y | V | L | A | V | F | Y | E | N | K | V | Y | N | V | K | I | R | F | L | E | 290 |
| 291 | R | N | Q | Q | F | A | L | G | T | G | L | R | G | D | E | K | F | D | S | V | 310 |
| 311 | E | D | I | I | E | H | Y | K | N | F | P | I | I | L | I | D | G | K | D | K | 330 |
| 331 | T | G | V | H | R | K | Q | C | H | L | T | Q | P | L | P | L | T | R | H | L | 350 |
| 351 | L | P | L |  |  |  |  |  |  |  |  |  |  |  |  |  |  |  |  |  | 353 |

FIG. 9A

```
   1  GGCTGCTGTTAACAACTTCATGTCCCCGTGGGTAGCAGGCAGGTGCTTCTGTCTGATCTG    60
  61  GCTCTCCTTGACCACTGTACTCATCAAATAGACCAAGATCCCCAGAGTCCAAGATCCTTA   120
 121  CAAGGGGCCAGAAAGGGATGAGCTTTCTGAAGAAGCACTGATGTAAATACCAGGAATT    180
 181  TTGACATCGAAGAAGATTTTTGTGATGGCAGCTGGGATTTGGCCATAATCTAGAAGACAC   240
 241  ATGGTGAATACAGTTGCAAGTCATTTAGTCATATTTCTTGCTAAATTGCTGTGTCTTCAA   300
 301  TGGGGCAATAGAAAGACAACTAAAGAAGGATCCAACGATTTGAAATTCCAGAACTTCAGT   360
 361  CTGCCAAAAAACAGGTCATGGCCTCGCATCAATAGTGCCACAGGCCAGTACCAGAGGATG   420
 421  AACAAGCCTCTTCTAGACTGGATTTGGCAGCTTGACCATTTATTATCGCACAGTGGATGC   480
 481  AATCAGAAGTCTGGGCACAGCATGGCTCAACTAGTTCCCTGTTCTGGGTCTCACAAGAC    540
 541  TGAAAGCAACATGCTGGCAGGGCTGCATTCTCCTCCAGGGGCTCTGAAGAGGAACTTGCT   600
 601  TCCAGATTCTTTCAGGAAAGAAACTTTGCTGCAGTCCTGGATGGAGCAAAAGGCCACAGT   660
 661  GATGATGACTATGATGACCCTGAGCTTCGGATGGAAGAGACATGGCAGTCGATTAAAATT   720
   1                                       M  E  E  T  W  Q  S  I  K  I    10
 721  TTACCAGCCCGGCCTATAAAGGAATCTGAATATGCAGATACACACTATTTCAAGGTTGCA   780
  11   L  P  A  R  P  I  K  E  S  E  Y  A  D  T  H  Y  F  K  V  A    30
 781  ATGGACACTCCCCTTCCGTTAGACACCAGGACCTCTATCTCCATTGGACAGCCGACCTGG   840
  31   M  D  T  P  L  P  L  D  T  R  T  S  I  S  I  G  Q  P  T  W    50
 841  AACACACAGACGAGGTTGGAAAGAGTGGACAAACCCATTTCCAAGGACGTCAGAAGCCAA   900
  51   N  T  Q  T  R  L  E  R  V  D  K  P  I  S  K  D  V  R  S  Q    70
 901  AACATTAAAGGAGATGCATCCGTAAGAAAGAACAAGATTCCTTTACCACCTCCTCGGCCT   960
  71   N  I  K  G  D  A  S  V  R  K  N  K  I  P  L  P  P  P  R  P    90
 961  CTCATAACACTTCCGAAGAAGTACCAACCCTTGCCCCCTGAGCCGGAGAGCAGCAGGCCA  1020
  91   L  I  T  L  P  K  K  Y  Q  P  L  P  P  E  P  E  S  S  R  P   110
1021  CCTTTATCTCAGAGACACACCTTTCCAGAAGTCCAGAGAATGCCCAGTCAGATAAGCTTA  1080
 111   P  L  S  Q  R  H  T  F  P  E  V  Q  R  M  P  S  Q  I  S  L   130
1081  AGGGACTTAAGTGAGGTCCTTGAAGCAGAAAAAGTTCCTCATAACCAGAGGAAGCCTGAA  1140
 131   R  D  L  S  E  V  L  E  A  E  K  V  P  H  N  Q  R  K  P  E   150
1141  TCAACTCATCTGTTAGAAAACCAAAATACTCAAGAGATTCCACTTGCCATTAGCAGTTCT  1200
 151   S  T  H  L  L  E  N  Q  N  T  Q  E  I  P  L  A  I  S  S  S   170
1201  TCATTCACGACAAGCAACCACAGTGTGCAAAACAGAGATCATAGAGGAGGCATGCAGCCC  1260
 171   S  F  T  T  S  N  H  S  V  Q  N  R  D  H  R  G  G  M  Q  P   190
1261  TGTTCTCCTCAGAGATGCCAGCCTCCAGCCAGCTGCAGCCCTCACGAAAATATACTGCCC  1320
 191   C  S  P  Q  R  C  Q  P  P  A  S  C  S  P  H  E  N  I  L  P   210
```

FIG. 9B

```
1321  TATAAATACACAAGCTGGAGACCACCTTTCCCCAAAAGGTCTGATAGAAAGGATGTCCAG  1380
 211   Y   K   Y   T   S   W   R   P   P   F   P   K   R   S   D   R   K   D   V   Q    230

1381  CACAATGAATGGTACATTGGAGAATACAGCCGCCAGGCAGTGGAAGAGGCATTCATGAAG  1440
 231   H   N   E   W   Y   I   G   E   Y   S   R   Q   A   V   E   E   A   F   M   K    250

1441  GAGAACAAGGATGGTAGTTTCTTGGTCCGAGATTGTTCCACAAAATCCAAGGAAGAGCCC  1500
 251   E   N   K   D   G   S   F   L   V   R   D   C   S   T   K   S   E   E   P    270

1501  TATGTTTTGGCTGTGTTTTATGAGAACAAAGTCTACAATGTAAAAATCCGCTTCCTGGAG  1560
 271   Y   V   L   A   V   F   Y   E   N   K   V   Y   N   V   K   I   R   F   L   E    290

1561  AGGAATCAGCAGTTTGCCCTGGGGACAGGACTCAGAGGAGATGAGAAGTTTGATTCAGTA  1620
 291   R   N   Q   Q   F   A   L   G   T   G   L   R   G   D   E   K   F   D   S   V    310

1621  GAAGACATCATCGAACACTACAAGAATTTTCCCATTATACTAATTGATGGGAAAGATAAA  1680
 311   E   D   I   I   E   H   Y   K   N   F   P   I   I   L   I   D   G   K   D   K    330

1681  ACTGGGGTCCACAGGAAACAGTGTCACCTCACTCAGCCACTCCCTCTCACCAGACACCTC  1740
 331   T   G   V   H   R   K   Q   C   H   L   T   Q   P   L   P   L   T   R   H   L    350

1741  TTGCCTCTGTAGCCTGGTCTTTGTGTTATCTTTGGTTTACTGGATTCAGCGCTTCCATTG  1800
 351   L   P   L   *                                                                     354

1801  TTTTCATTGATTTCAAAAGTTTATTTTCTGTGCCTTCAAGGGACAACTTTTTTAACTTTG  1860

1861  GAGAAAAGAAAAACACTCTATAACAGAGAGTGGAAAATCACTCACGGTTTTGAAAGTTCA  1920

1921  AACCACAGAGAAATATTTATAACATGCAAAAAATAAAAACATTCTAGTAACTGGCCACT  1980

1981  GGAAAATAAATAAAAATAAAAACTAGGGTTTTAAAAGTATCTTCTAAAAAACAACAACAA  2040

2041  AAAATACTATAAACATAGCCATTATGCTCATGATACAGGCGAGCAGCAAAGGGCACCAGA  2100

2101  AGCTGTTGCTTAAATGTTTGCAGTCAGTGCAAGACAAGTCTATGGGAAATTCCCAAATCT  2160

2161  GTGCTCTTTACAGGACACTGCGCTGCCTTTATGTCAGTTGTTGGGCCTTACATATATACA  2220

2221  ATGTGTGGATGATTTCTTACACTAAAGATGCTGGGCTGGGTGCGGTGCCTCATGCCTGTA  2280

2281  ATCCCAGCACTTTGGGAGGCTGAGGTGGACAGATCACGAGGTCAGGAGATCAAGACCATC  2340

2341  CTGGCTAACATGGTGAAACCCCATGTCTACTAAAAATACAAAAAATCAGCTGGGCGTGGT  2400

2401  GGTGGGTGCCTGTAGTCCCAGCTACTCGGGAGGCTGAGGCAGGAGAATGGTGTGAACCCG  2460

2461  GGAGGCGGAGCTTGCAGTGAGCCGAAATCGCGCCACTGCACTCCAATCCAGCCTGGGGAC  2520

2521  AGAGAGACTCCGTCTCAAAA                                           2540
```

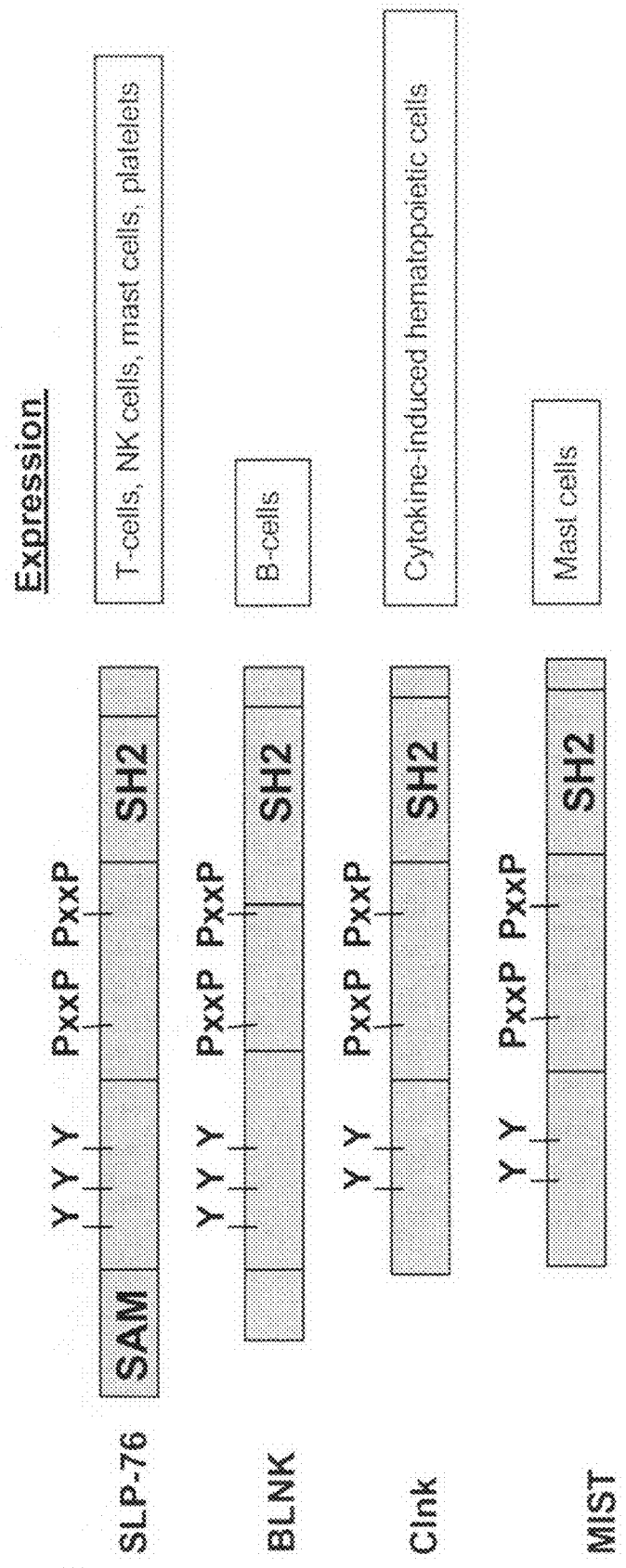

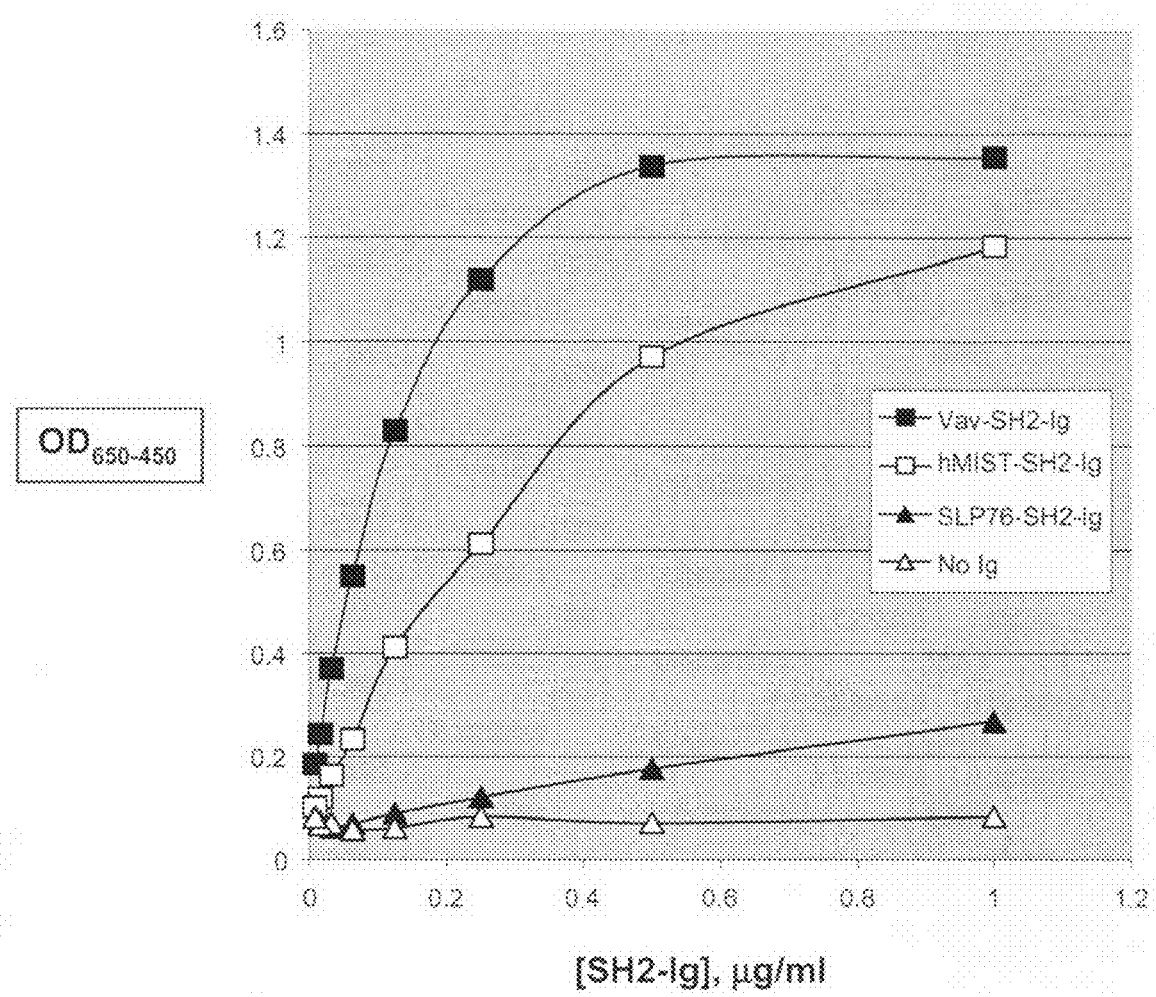

SEQUENCE LISTING

<160> NUMBER OF SEQ ID NOS: 52

<210> SEQ ID NO 1
<211> LENGTH: 1851
<212> TYPE: DNA
<213> ORGANISM: Homo sapiens

<400> SEQUENCE: 1

-continued

```
cctagagcca gcagagtcca ggctgctgtt aacaacttca tgtccccgtg ggtagcaggc      60
aggtgcttct gtctgatctg ctctccttg accactgtac tcatcaaata gaccaagatc      120
cccagagtcc aagatcctta caaggggggcc agaaagggat gagctttctg aagaagcact    180
gatgtaaaat accaggaatt ttgacatcga agaagatttt tgtgatggca gctgggattt    240
ggccataatc tagaagacac atggtgaata cagttgcaag tcatttagtc atatttcttg    300
ctaaattgct gtgtcttcaa tggctgaatt gaagatccct cttacccgcc aggtgccaag    360
aactatgaac aggcagggca atagaaagac aactaaagaa ggatccaacg atttgaaatt    420
ccagaacttc agtctgccaa aaacaggtc atggcctcgc atcaatagtg ccacaggcca     480
gtaccagagg atgaacaagc ctcttctaga ctgggaaaga aactttgctg cagtcctgga    540
tggagcaaaa ggccacagtg atgatgacta tgatgaccct gagcttcgga tggaagagac    600
atggcagtcg attaaaattt taccagcccg gcctataaag gaatctgaat atgcagatac    660
acactatttc aaggttgcaa tggacactcc ccttccgtta gacaccagga cctctatctc    720
cattggacag ccgacctgga acacacagac gaggttggaa agagtggaca aacccatttc    780
caaggacgtc agaagccaaa acattaaagg agatgcatcc gtaagaaaga caagattcc    840
tttaccacct cctcggcctc tcataacact tccgaagaag taccaaccct gccccctga     900
gccggagagc agcaggccac ctttatctca gagacacacc tttccagaag tccagagaat    960
gcccagtcag ataagcttaa gggacttaag tgaggtcctt gaagcagaaa aagttcctca    1020
taaccagagg aagcctgaat caactcatct gttagaaaac caaatactc aagagattcc     1080
acttgccatt agcagttctt cattcacgac aagcaaccac agtgtgcaaa acagagatca    1140
tagaggaggc atgcagccct gttctcctca gagatgccag cctccagcca gctgcagccc    1200
tcacgaaaat atactgccct ataaatacac aagctggaga ccacctttcc ccaaaaggtc    1260
tgatagaaag gatgtccagc acaatgaatg gtacattgga gaatacagcc gccaggcagt    1320
ggaagaggca ttcatgaagg agaacaagga tggtagtttc ttggtccgag attgttccac    1380
aaaatccaag gaagagccct atgttttggc tgtgttttat gagaacaaag tctacaatgt    1440
aaaaatccgc ttcctggaga ggaatcagca gtttgccctg gggacaggac tcagaggaga    1500
tgagaagttt gattcagtag aagacatcat cgaacactac aagaatttttc ccattatact    1560
aattgatggg aaagataaaa ctggggtcca caggaaacag tgtcacctca ctcagccact    1620
ccctctcacc agacacctct tgcctctgta gcctggtctt tgtgttatct ttggtttact    1680
ggattcagcg cttccattgt tttcattgat ttcaaaagtt tattttctgt gccttcaagg    1740
gacaacttttt ttaactttgg agaaagaaa aacactctat aacagagagt ggaaaatcac    1800
tcacggtttt gaaagttcaa accacagaga aaatatttat aacatgcaaa a            1851
```

<210> SEQ ID NO 2
<211> LENGTH: 443
<212> TYPE: PRT
<213> ORGANISM: Homo sapiens

<400> SEQUENCE: 2

Met Ala Glu Leu Lys Ile Pro Leu Thr Arg Gln Val Pro Arg Thr Met
1               5                   10                  15

Asn Arg Gln Gly Asn Arg Lys Thr Thr Lys Glu Gly Ser Asn Asp Leu
            20                  25                  30

Lys Phe Gln Asn Phe Ser Leu Pro Lys Asn Arg Ser Trp Pro Arg Ile
        35                  40                  45

Asn Ser Ala Thr Gly Gln Tyr Gln Arg Met Asn Lys Pro Leu Leu Asp
 50                  55                  60

Trp Glu Arg Asn Phe Ala Ala Val Leu Asp Gly Ala Lys Gly His Ser
 65                  70                  75                  80

Asp Asp Asp Tyr Asp Pro Glu Leu Arg Met Glu Glu Thr Trp Gln
                 85                  90                  95

Ser Ile Lys Ile Leu Pro Ala Arg Pro Ile Lys Glu Ser Glu Tyr Ala
                100                 105                 110

Asp Thr His Tyr Phe Lys Val Ala Met Asp Thr Pro Leu Pro Leu Asp
            115                 120                 125

Thr Arg Thr Ser Ile Ser Ile Gly Gln Pro Thr Trp Asn Thr Gln Thr
    130                 135                 140

Arg Leu Glu Arg Val Asp Lys Pro Ile Ser Lys Asp Val Arg Ser Gln
145                 150                 155                 160

Asn Ile Lys Gly Asp Ala Ser Val Arg Lys Asn Lys Ile Pro Leu Pro
                165                 170                 175

Pro Pro Arg Pro Leu Ile Thr Leu Pro Lys Lys Tyr Gln Pro Leu Pro
            180                 185                 190

Pro Glu Pro Glu Ser Ser Arg Pro Pro Leu Ser Gln Arg His Thr Phe
        195                 200                 205

Pro Glu Val Gln Arg Met Pro Ser Gln Ile Ser Leu Arg Asp Leu Ser
    210                 215                 220

Glu Val Leu Glu Ala Glu Lys Val Pro His Asn Gln Arg Lys Pro Glu
225                 230                 235                 240

Ser Thr His Leu Leu Glu Asn Gln Asn Thr Gln Glu Ile Pro Leu Ala
                245                 250                 255

Ile Ser Ser Ser Phe Thr Ser Asn His Ser Val Gln Asn Arg
            260                 265                 270

Asp His Arg Gly Gly Met Gln Pro Cys Ser Pro Gln Arg Cys Gln Pro
    275                 280                 285

Pro Ala Ser Cys Ser Pro His Glu Asn Ile Leu Pro Tyr Lys Tyr Thr
290                 295                 300

Ser Trp Arg Pro Pro Phe Pro Lys Arg Ser Asp Arg Lys Asp Val Gln
305                 310                 315                 320

His Asn Glu Trp Tyr Ile Gly Glu Tyr Ser Arg Gln Ala Val Glu Glu
                325                 330                 335

Ala Phe Met Lys Glu Asn Lys Asp Gly Ser Phe Leu Val Arg Asp Cys
            340                 345                 350

Ser Thr Lys Ser Lys Glu Glu Pro Tyr Val Leu Ala Val Phe Tyr Glu
    355                 360                 365

Asn Lys Val Tyr Asn Val Lys Ile Arg Phe Leu Glu Arg Asn Gln Gln
    370                 375                 380

Phe Ala Leu Gly Thr Gly Leu Arg Gly Asp Glu Lys Phe Asp Ser Val
385                 390                 395                 400

Glu Asp Ile Ile Glu His Tyr Lys Asn Phe Pro Ile Ile Leu Ile Asp
                405                 410                 415

Gly Lys Asp Lys Thr Gly Val His Arg Lys Gln Cys His Leu Thr Gln
            420                 425                 430

Pro Leu Pro Leu Thr Arg His Leu Leu Pro Leu
        435                 440

<210> SEQ ID NO 3
<211> LENGTH: 2335
<212> TYPE: DNA

<213> ORGANISM: Homo sapiens

<400> SEQUENCE: 3

```
gtcagacctc tcaggtctgt ggctgcattt cacaggaaac caagtctaaa acggacctat      60
caggaggttt tctgctgaag ggcactgctt agcatcgaga agaattcaac ccaccgcctt     120
actaatttcc agtgcccaa ggtctctgca ctgccgcccc tcctcacagg agacggacac      180
ctcagcctag atcccttggt gctctccacg ctgttcaggc tgaattgaag atccctctta     240
cccgccaggt gccaagaact atgaacaggc agggcaatag aaagacaact aaagaaggat     300
ccaacgattt gaaattccag aacttcagtc tgccaaaaaa caggtcatgg cctcgcatca     360
atagtgccac aggccagtac cagaggatga caagcctct tctagactgg gaaagaaact      420
ttgctgcagt cctggatgga gcaaaaggcc acagtgatga tgactatgat gaccctgagc     480
ttcggatgga agagacatgg cagtcgatta aaattttacc agcccggcct ataaaggaat     540
ctgaatatgc agatacacac tatttcaagg ttgcaatgga cactcccctt ccgttagaca     600
ccaggacctc tatctccatt ggacagccga cctggaacac acagacgagg ttggaaagag     660
tggacaaacc catttccaag gacgtcagaa gccaaaacat taaggagat gcatccgtaa      720
gaaagaacaa gattcctta ccacctcctc ggcctctcat aacacttccg aagaagtacc      780
aacccttgcc ccctgagccg gagagcagca ggccaccttt atctcagaga cacacctttc     840
cagaagtcca gagaatgccc agtcagataa gcttaaggga cttaagtgag gtccttgaag     900
cagaaaaagt tcctcataac cagaggaagc ctgaatcaac tcatctgtta gaaaaccaaa     960
atactcaaga gattccactt gccattagca gttcttcatt cacgacaagc aaccacagtg    1020
tgcaaaacag agatcataga ggaggcatgc agccctgttc tcctcagaga tgccagcctc    1080
cagccagctg cagccctcac gaaaatatac tgccctataa atacacaagc tggagaccac    1140
cttttcccca aaggtctgat agaaaggatg tccagcacaa tgaatggtac attggagaat    1200
acagccgcca ggcagtggaa gaggcattca tgaaggagaa caaggatggt agtttcttgg    1260
tccgagattt ttccacaaaa tccaaggaag agccctatgt tttggctgtg ttttatgaga    1320
acaaagtcta caatgtaaaa atccgcttcc tggagaggaa tcagcagttt gccctgggga    1380
caggactcag aggagatgag aagtttgatt cagtagaaga catcatcgaa cactacaaga    1440
attttcccat tatactaatt gatgggaaag ataaaactgg ggtccacagg aaacagtgtc    1500
acctcactca gccactccct ctcaccgac acctcttgcc tctgtagcct ggtctttgtg     1560
ttatctttgg tttactggat tcagcgcttc cattgttttc attgatttca aaagtttatt    1620
ttctgtgcct tcaagggaca acttttttaa cttttggagaa agaaaaaca ctctataaca    1680
gagagtggaa aatcactcac ggttttgaaa gttcaaacca cagagaaaat atttataaca    1740
tgcaaaaaat aaaaacattc tagtaactgg ccactggaaa ataaataaaa ataaaaacta    1800
gggttttaaa agtatcttct aaaaacaac aacaaaaaat actataaaca tagccattat     1860
gctcatgata caggcgagca gcaaagggca ccagaagctg ttgcttaaat gtttgcagtc    1920
agtgcaagac aagtctatgg gaaattccca aatctgtgct cttttacagga cactgcgctg    1980
cctttatgtc agttgttggg ccttacatat atacaatgtg tggatgattt cttacactaa    2040
agatgctggc tgggtgcgg tgcctcatgc ctgtaatccc agcactttgg gaggctgagg     2100
tggacagatc acgaggtcag gagatcaaga ccatcctggc taacatggtg aaaccccatg    2160
tctactaaaa atacaaaaaa tcagctgggc gtggtggtgg gtgcctgtag tcccagctac    2220
tcgggaggct gaggcaggag aatggtgtga acccgggagg cggagcttgc agtgagccga    2280
```

-continued aatcgcgcca ctgcactcca atccagcctg gggacagaga gactccgtct caaaa    2335

<210> SEQ ID NO 4
<211> LENGTH: 428
<212> TYPE: PRT
<213> ORGANISM: Homo sapiens

<400> SEQUENCE: 4

Met Asn Arg Gln Gly Asn Arg Lys Thr Thr Lys Glu Gly Ser Asn Asp
1               5                   10                  15

Leu Lys Phe Gln Asn Phe Ser Leu Pro Lys Asn Arg Ser Trp Pro Arg
            20                  25                  30

Ile Asn Ser Ala Thr Gly Gln Tyr Gln Arg Met Asn Lys Pro Leu Leu
        35                  40                  45

Asp Trp Glu Arg Asn Phe Ala Ala Val Leu Asp Gly Ala Lys Gly His
    50                  55                  60

Ser Asp Asp Tyr Asp Asp Pro Glu Leu Arg Met Glu Glu Thr Trp
65                  70                  75                  80

Gln Ser Ile Lys Ile Leu Pro Ala Arg Pro Ile Lys Glu Ser Glu Tyr
                85                  90                  95

Ala Asp Thr His Tyr Phe Lys Val Ala Met Asp Thr Pro Leu Pro Leu
            100                 105                 110

Asp Thr Arg Thr Ser Ile Ser Ile Gly Gln Pro Thr Trp Asn Thr Gln
        115                 120                 125

Thr Arg Leu Glu Arg Val Asp Lys Pro Ile Ser Lys Asp Val Arg Ser
    130                 135                 140

Gln Asn Ile Lys Gly Asp Ala Ser Val Arg Lys Asn Lys Ile Pro Leu
145                 150                 155                 160

Pro Pro Pro Arg Pro Leu Ile Thr Leu Pro Lys Lys Tyr Gln Pro Leu
                165                 170                 175

Pro Pro Glu Pro Glu Ser Ser Arg Pro Pro Leu Ser Gln Arg His Thr
            180                 185                 190

Phe Pro Glu Val Gln Arg Met Pro Ser Gln Ile Ser Leu Arg Asp Leu
        195                 200                 205

Ser Glu Val Leu Glu Ala Glu Lys Val Pro His Asn Gln Arg Lys Pro
    210                 215                 220

Glu Ser Thr His Leu Leu Glu Asn Gln Asn Thr Gln Glu Ile Pro Leu
225                 230                 235                 240

Ala Ile Ser Ser Ser Phe Thr Thr Ser Asn His Ser Val Gln Asn
                245                 250                 255

Arg Asp His Arg Gly Gly Met Gln Pro Cys Ser Pro Gln Arg Cys Gln
            260                 265                 270

Pro Pro Ala Ser Cys Ser Pro His Glu Asn Ile Leu Pro Tyr Lys Tyr
        275                 280                 285

Thr Ser Trp Arg Pro Pro Phe Pro Lys Arg Ser Arg Lys Asp Val
    290                 295                 300

Gln His Asn Glu Trp Tyr Ile Gly Glu Tyr Ser Arg Gln Ala Val Glu
305                 310                 315                 320

Glu Ala Phe Met Lys Glu Asn Lys Asp Gly Ser Phe Leu Val Arg Asp
                325                 330                 335

Cys Ser Thr Lys Ser Lys Glu Glu Pro Tyr Val Leu Ala Val Phe Tyr
            340                 345                 350

Glu Asn Lys Val Tyr Asn Val Lys Ile Arg Phe Leu Glu Arg Asn Gln
        355                 360                 365

```
Gln Phe Ala Leu Gly Thr Gly Leu Arg Gly Asp Glu Lys Phe Asp Ser
        370                 375                 380

Val Glu Asp Ile Ile Glu His Tyr Lys Asn Phe Pro Ile Ile Leu Ile
385                 390                 395                 400

Asp Gly Lys Asp Lys Thr Gly Val His Arg Lys Gln Cys His Leu Thr
                405                 410                 415

Gln Pro Leu Pro Leu Thr Arg His Leu Leu Pro Leu
            420                 425

<210> SEQ ID NO 5
<211> LENGTH: 2540
<212> TYPE: DNA
<213> ORGANISM: Homo sapiens

<400> SEQUENCE: 5
ggctgctgtt aacaacttca tgtccccgtg ggtagcaggc aggtgcttct gtctgatctg      60
gctctccttg accactgtac tcatcaaata gaccaagatc cccagagtcc aagatcctta    120
caagggggcc agaaagggat gagctttctg aagaagcact gatgtaaaat accaggaatt    180
ttgacatcga agaagatttt tgtgatggca gctgggattt ggccataatc tagaagacac    240
atggtgaata cagttgcaag tcatttagtc atatttcttg ctaaattgct gtgtcttcaa    300
tggggcaata gaaagacaac taagaaagga tccaacgatt gaaattccaa gaacttcagt    360
ctgccaaaaa acaggtcatg gcctcgcatc aatagtgcca caggccagta ccagaggatg    420
aacaagcctc ttctagactg gatttggcag cttgaccatt tattatcgca cagtggatgc    480
aatcagaagt ctgggcacag catggctcaa ctagttcccc tgttctgggt ctcacaagac    540
tgaaagcaac atgctggcag gctgcattc tcctccaggg gctctgaaga ggaacttgct    600
tccagattct ttcaggaaag aaactttgct gcagtcctgg atggagcaaa aggccacagt    660
gatgatgact atgatgaccc tgagcttcgg atggaagaga catggcagtc gattaaaatt    720
ttaccagccc ggcctataaa ggaatctgaa tatgcagata cacactattt caaggttgca    780
atggacactc cccttccgtt agacaccagg acctctatct ccattggaca gccgacctgg    840
aacacacaga cgaggttgga aagagtggac aaacccattt ccaaggacgt cagaagccaa    900
aacattaaag gagatgcatc cgtaagaaag aacaagattc ctttaccacc tcctcggcct    960
ctcataacac ttccgaagaa gtaccaaccc ttgccccctg agccggagag cagcaggcca   1020
cctttatctc agagacacac ctttccagaa gtccagagaa tgcccagtca gataagctta   1080
agggacttaa gtgaggtcct tgaagcagaa aaagttcctc ataaccagag gaagcctgaa   1140
tcaactcatc tgttagaaaa ccaaaatact caagagattc cacttgccat tagcagttct   1200
tcattcacga caagcaacca cagtgtgcaa aacagagatc atagaggagg catgcagccc   1260
tgttctcctc agagatgcca gcctccagcc agctgcagcc ctcacgaaaa tatactgccc   1320
tataaataca aagctggag accacctttc cccaaaaggt ctgatagaaa ggatgtccag   1380
cacaatgaat ggtacattgg agaatacagc cgccaggcag tggaagaggc attcatgaag   1440
gagaacaagg atggtagttt cttggtccga gattgttcca caaatccaa ggaagagccc   1500 tatgttttgg ctgtgtttta tgagaacaaa gtctacaatg taaaaatccg cttcctggag   1560
aggaatcagc agtttgccct ggggacagga ctcagaggag atgagaagtt tgattcagta   1620
gaagacatca tcgaacacta caagaatttt cccattatac taattgatgg aaaagataaa   1680
actggggtcc acaggaaaca gtgtcacctc actcagccac tccctctcac cagacacctc   1740
```

```
ttgcctctgt agcctggtct ttgtgttatc tttggtttac tggattcagc gcttccattg    1800 tttcattga tttcaaaagt ttattttctg tgccttcaag ggacaacttt tttaactttg    1860
gagaaaagaa aaacactcta taacagagag tggaaaatca ctcacggttt tgaaagttca    1920
aaccacagag aaaatattta taacatgcaa aaaataaaaa cattctagta actggccact    1980
ggaaaataaa taaaaataaa aactagggtt ttaaaagtat cttctaaaaa acaacaacaa    2040
aaaatactat aaacatagcc attatgctca tgatacaggc gagcagcaaa gggcaccaga    2100
agctgttgct taaatgtttg cagtcagtgc aagacaagtc tatgggaaat tcccaaatct    2160
gtgctcttta caggacactg cgctgccttt atgtcagttg ttgggcctta catatataca    2220
atgtgtggat gatttcttac actaaagatg ctgggctggg tgcggtgcct catgcctgta    2280
atcccagcac tttgggaggc tgaggtggac agatcacgag gtcaggagat caagaccatc    2340
ctggctaaca tggtgaaacc ccatgtctac taaaaataca aaaaatcagc tgggcgtggt    2400
ggtgggtgcc tgtagtccca gctactcggg aggctgaggc aggagaatgg tgtgaacccg    2460
ggaggcggag cttgcagtga gccgaaatcg cgccactgca ctccaatcca gcctggggac    2520
agagagactc cgtctcaaaa                                                2540
```

<210> SEQ ID NO 6
<211> LENGTH: 353
<212> TYPE: PRT
<213> ORGANISM: Homo sapiens

<400> SEQUENCE: 6

```
Met Glu Glu Thr Trp Gln Ser Ile Lys Ile Leu Pro Ala Arg Pro Ile
1               5                   10                  15

Lys Glu Ser Glu Tyr Ala Asp Thr His Tyr Phe Lys Val Ala Met Asp
            20                  25                  30

Thr Pro Leu Pro Leu Asp Thr Arg Thr Ser Ile Ser Ile Gly Gln Pro
        35                  40                  45

Thr Trp Asn Thr Gln Thr Arg Leu Glu Arg Val Asp Lys Pro Ile Ser
    50                  55                  60

Lys Asp Val Arg Ser Gln Asn Ile Lys Gly Asp Ala Ser Val Arg Lys
65                  70                  75                  80

Asn Lys Ile Pro Leu Pro Pro Arg Pro Leu Ile Thr Leu Pro Lys
                85                  90                  95

Lys Tyr Gln Pro Leu Pro Pro Glu Pro Glu Ser Ser Arg Pro Pro Leu
            100                 105                 110

Ser Gln Arg His Thr Phe Pro Glu Val Gln Arg Met Pro Ser Gln Ile
        115                 120                 125

Ser Leu Arg Asp Leu Ser Glu Val Leu Glu Ala Glu Lys Val Pro His
    130                 135                 140

Asn Gln Arg Lys Pro Glu Ser Thr His Leu Leu Glu Asn Gln Asn Thr
145                 150                 155                 160

Gln Glu Ile Pro Leu Ala Ile Ser Ser Ser Phe Thr Thr Ser Asn
                165                 170                 175

His Ser Val Gln Asn Arg Asp His Arg Gly Gly Met Gln Pro Cys Ser
            180                 185                 190

Pro Gln Arg Cys Gln Pro Pro Ala Ser Cys Ser Pro His Glu Asn Ile
        195                 200                 205

Leu Pro Tyr Lys Tyr Thr Ser Trp Arg Pro Pro Phe Pro Lys Arg Ser
    210                 215                 220

Asp Arg Lys Asp Val Gln His Asn Glu Trp Tyr Ile Gly Glu Tyr Ser
```

-continued

```
                225                 230                 235                 240
Arg Gln Ala Val Glu Ala Phe Met Lys Glu Asn Lys Asp Gly Ser
                245                 250                 255
Phe Leu Val Arg Asp Cys Ser Thr Lys Ser Lys Glu Glu Pro Tyr Val
                260                 265                 270
Leu Ala Val Phe Tyr Glu Asn Lys Val Tyr Asn Val Lys Ile Arg Phe
            275                 280                 285
Leu Glu Arg Asn Gln Gln Phe Ala Leu Gly Thr Gly Leu Arg Gly Asp
        290                 295                 300
Glu Lys Phe Asp Ser Val Glu Asp Ile Ile Glu His Tyr Lys Asn Phe
305                 310                 315                 320
Pro Ile Ile Leu Ile Asp Gly Lys Asp Lys Thr Gly Val His Arg Lys
                325                 330                 335
Gln Cys His Leu Thr Gln Pro Leu Pro Leu Thr Arg His Leu Leu Pro
            340                 345                 350
Leu
```

<210> SEQ ID NO 7
<211> LENGTH: 8
<212> TYPE: PRT
<213> ORGANISM: Homo sapiens

<400> SEQUENCE: 7

```
Asp Asp Tyr Glu Ser Pro Asn Asp
1               5
```

<210> SEQ ID NO 8
<211> LENGTH: 20
<212> TYPE: DNA
<213> ORGANISM: Homo sapiens

<400> SEQUENCE: 8
tggtacattg gagaatacag            20

<210> SEQ ID NO 9
<211> LENGTH: 19
<212> TYPE: DNA
<213> ORGANISM: Homo sapiens

<400> SEQUENCE: 9
gctgattcct ctccaggaa             19

<210> SEQ ID NO 10
<211> LENGTH: 30
<212> TYPE: DNA
<213> ORGANISM: Homo sapiens

<400> SEQUENCE: 10
gtggaagagg cattcatgaa ggagaacaag   30

<210> SEQ ID NO 11
<211> LENGTH: 20
<212> TYPE: DNA
<213> ORGANISM: Homo sapiens

<400> SEQUENCE: 11
gtaaggatct tggactctgg            20

<210> SEQ ID NO 12
<211> LENGTH: 20

<212> TYPE: DNA
<213> ORGANISM: Homo sapiens

<400> SEQUENCE: 12
ctccatccag gactgcagca                                           20

<210> SEQ ID NO 13
<211> LENGTH: 20
<212> TYPE: DNA
<213> ORGANISM: Homo sapiens

<400> SEQUENCE: 13
ggtgaataca gttgcaagtc                                           20

<210> SEQ ID NO 14
<211> LENGTH: 20
<212> TYPE: DNA
<213> ORGANISM: Homo sapiens

<400> SEQUENCE: 14
gagcttcgga tggaagagac                                           20

<210> SEQ ID NO 15
<211> LENGTH: 20
<212> TYPE: DNA
<213> ORGANISM: Homo sapiens

<400> SEQUENCE: 15
tacatgtgcc atgctggtgc                                           20

<210> SEQ ID NO 16
<211> LENGTH: 20
<212> TYPE: DNA
<213> ORGANISM: Homo sapiens

<400> SEQUENCE: 16
ctggaggctg gcatctctga                                           20

<210> SEQ ID NO 17
<211> LENGTH: 20
<212> TYPE: DNA
<213> ORGANISM: Homo sapiens

<400> SEQUENCE: 17
agtggctgag tgaggtgaca                                           20

<210> SEQ ID NO 18
<211> LENGTH: 20
<212> TYPE: DNA
<213> ORGANISM: Homo sapiens

<400> SEQUENCE: 18
acttgtcttg cactgactgc                                           20

<210> SEQ ID NO 19
<211> LENGTH: 20
<212> TYPE: DNA
<213> ORGANISM: Homo sapiens

<400> SEQUENCE: 19
cactgagtga gctgatatgg                                           20

<210> SEQ ID NO 20

```
<211> LENGTH: 21
<212> TYPE: DNA
<213> ORGANISM: Homo sapiens

<400> SEQUENCE: 20
aggcagtgga agaggcattc a                                              21

<210> SEQ ID NO 21
<211> LENGTH: 20
<212> TYPE: DNA
<213> ORGANISM: Homo sapiens

<400> SEQUENCE: 21
ttgcctctgt agcctggtct                                                20

<210> SEQ ID NO 22
<211> LENGTH: 20
<212> TYPE: DNA
<213> ORGANISM: Homo sapiens

<400> SEQUENCE: 22
tacaggacac tgcgctgcct                                                20

<210> SEQ ID NO 23
<211> LENGTH: 18
<212> TYPE: PRT
<213> ORGANISM: Homo sapiens

<400> SEQUENCE: 23

Val Leu Asp Gly Ala Lys Gly His Ser Asp Asp Tyr Asp Asp Pro
1               5                   10                  15
Glu Leu

<210> SEQ ID NO 24
<211> LENGTH: 18
<212> TYPE: PRT
<213> ORGANISM: Homo sapiens

<400> SEQUENCE: 24

Lys Ile Leu Pro Ala Arg Pro Ile Lys Glu Ser Glu Tyr Ala Asp Thr
1               5                   10                  15
His Tyr

<210> SEQ ID NO 25
<211> LENGTH: 17
<212> TYPE: PRT
<213> ORGANISM: Homo sapiens

<400> SEQUENCE: 25

Arg Asp Cys Ser Thr Lys Ser Lys Glu Glu Pro Tyr Val Leu Ala Val
1               5                   10                  15
Phe

<210> SEQ ID NO 26
<211> LENGTH: 13
<212> TYPE: PRT
<213> ORGANISM: Homo sapiens

<400> SEQUENCE: 26

Gln Gly Asn Arg Lys Thr Thr Lys Glu Gly Ser Asn Asp
1               5                   10
```

```
<210> SEQ ID NO 27
<211> LENGTH: 13
<212> TYPE: PRT
<213> ORGANISM: Homo sapiens

<400> SEQUENCE: 27

Glu Glu Thr Trp Gln Ser Ile Lys Ile Leu Pro Ala Arg
1               5                   10

<210> SEQ ID NO 28
<211> LENGTH: 13
<212> TYPE: PRT
<213> ORGANISM: Homo sapiens

<400> SEQUENCE: 28

Ile Lys Gly Asp Ala Ser Val Arg Lys Asn Lys Ile Pro
1               5                   10

<210> SEQ ID NO 29
<211> LENGTH: 13
<212> TYPE: PRT
<213> ORGANISM: Homo sapiens

<400> SEQUENCE: 29

Pro Pro Glu Pro Glu Ser Ser Arg Pro Pro Leu Ser Gln
1               5                   10

<210> SEQ ID NO 30
<211> LENGTH: 13
<212> TYPE: PRT
<213> ORGANISM: Homo sapiens

<400> SEQUENCE: 30

Ser Arg Pro Pro Leu Ser Gln Arg His Thr Phe Pro Glu
1               5                   10

<210> SEQ ID NO 31
<211> LENGTH: 13
<212> TYPE: PRT
<213> ORGANISM: Homo sapiens

<400> SEQUENCE: 31

Pro Tyr Lys Tyr Thr Ser Trp Arg Pro Pro Phe Pro Lys
1               5                   10

<210> SEQ ID NO 32
<211> LENGTH: 13
<212> TYPE: PRT
<213> ORGANISM: Homo sapiens

<400> SEQUENCE: 32

Pro Phe Pro Lys Arg Ser Asp Arg Lys Asp Val Gln His
1               5                   10

<210> SEQ ID NO 33
<211> LENGTH: 13
<212> TYPE: PRT
<213> ORGANISM: Homo sapiens

<400> SEQUENCE: 33

Leu Val Arg Asp Cys Ser Thr Lys Ser Lys Glu Glu Pro
1               5                   10

<210> SEQ ID NO 34
<211> LENGTH: 14
```

```
<212> TYPE: PRT
<213> ORGANISM: Homo sapiens

<400> SEQUENCE: 34

Gln Gly Asn Arg Lys Thr Thr Lys Glu Gly Ser Asn Asp Leu
1               5                   10

<210> SEQ ID NO 35
<211> LENGTH: 14
<212> TYPE: PRT
<213> ORGANISM: Homo sapiens

<400> SEQUENCE: 35

Gly Ala Lys Gly His Ser Asp Asp Tyr Asp Asp Pro Glu
1               5                   10

<210> SEQ ID NO 36
<211> LENGTH: 14
<212> TYPE: PRT
<213> ORGANISM: Homo sapiens

<400> SEQUENCE: 36

Thr Trp Asn Thr Gln Thr Arg Leu Glu Arg Val Asp Lys Pro
1               5                   10

<210> SEQ ID NO 37
<211> LENGTH: 14
<212> TYPE: PRT
<213> ORGANISM: Homo sapiens

<400> SEQUENCE: 37

Leu Ser Gln Arg His Thr Phe Pro Glu Val Gln Arg Met Pro
1               5                   10

<210> SEQ ID NO 38
<211> LENGTH: 14
<212> TYPE: PRT
<213> ORGANISM: Homo sapiens

<400> SEQUENCE: 38

Met Pro Ser Gln Ile Ser Leu Arg Asp Leu Ser Glu Val Leu
1               5                   10

<210> SEQ ID NO 39
<211> LENGTH: 14
<212> TYPE: PRT
<213> ORGANISM: Homo sapiens

<400> SEQUENCE: 39

Pro Pro Ala Ser Cys Ser Pro His Glu Asn Ile Leu Pro Tyr
1               5                   10

<210> SEQ ID NO 40
<211> LENGTH: 14
<212> TYPE: PRT
<213> ORGANISM: Homo sapiens

<400> SEQUENCE: 40

Asp Cys Ser Thr Lys Ser Lys Glu Glu Pro Tyr Val Leu Ala
1               5                   10

<210> SEQ ID NO 41
<211> LENGTH: 14
<212> TYPE: PRT
<213> ORGANISM: Homo sapiens
```

```
<400> SEQUENCE: 41

Asp Glu Lys Phe Asp Ser Val Glu Asp Ile Ile Glu His Tyr
1               5                   10

<210> SEQ ID NO 42
<211> LENGTH: 14
<212> TYPE: PRT
<213> ORGANISM: Homo sapiens

<400> SEQUENCE: 42

Asn Arg Gln Gly Asn Arg Lys Thr Thr Lys Glu Gly Ser Asn
1               5                   10

<210> SEQ ID NO 43
<211> LENGTH: 14
<212> TYPE: PRT
<213> ORGANISM: Homo sapiens

<400> SEQUENCE: 43

Asp Leu Lys Phe Gln Asn Phe Ser Leu Pro Lys Asn Arg Ser
1               5                   10

<210> SEQ ID NO 44
<211> LENGTH: 14
<212> TYPE: PRT
<213> ORGANISM: Homo sapiens

<400> SEQUENCE: 44

Phe Ser Leu Pro Lys Asn Arg Ser Trp Pro Arg Ile Asn Ser
1               5                   10

<210> SEQ ID NO 45
<211> LENGTH: 14
<212> TYPE: PRT
<213> ORGANISM: Homo sapiens

<400> SEQUENCE: 45

Ser Phe Thr Thr Ser Asn His Ser Val Gln Asn Arg Asp His
1               5                   10

<210> SEQ ID NO 46
<211> LENGTH: 16
<212> TYPE: PRT
<213> ORGANISM: Homo sapiens

<400> SEQUENCE: 46

Thr Met Asn Arg Gln Gly Asn Arg Lys Thr Thr Lys Glu Gly Ser Asn
1               5                   10                  15

<210> SEQ ID NO 47
<211> LENGTH: 16
<212> TYPE: PRT
<213> ORGANISM: Homo sapiens

<400> SEQUENCE: 47

Arg Asp His Arg Gly Gly Met Gln Pro Cys Ser Pro Gln Arg Cys Gln
1               5                   10                  15

<210> SEQ ID NO 48
<211> LENGTH: 13
<212> TYPE: PRT
<213> ORGANISM: Homo sapiens

<400> SEQUENCE: 48
```

```
Leu Gly Thr Gly Leu Arg Gly Asp Glu Lys Phe Asp Ser
1               5                   10

<210> SEQ ID NO 49
<211> LENGTH: 38
<212> TYPE: DNA
<213> ORGANISM: Homo sapiens

<400> SEQUENCE: 49
gcagcagcgg ccgcgactat gatgaccctg agcttcgg                              38

<210> SEQ ID NO 50
<211> LENGTH: 36
<212> TYPE: DNA
<213> ORGANISM: Homo sapiens

<400> SEQUENCE: 50
gcagcagtcg accagaggca agaggtgtct ggtgag                                36

<210> SEQ ID NO 51
<211> LENGTH: 36
<212> TYPE: DNA
<213> ORGANISM: Homo sapiens

<400> SEQUENCE: 51
gcagcagcgg ccgcatggct gaattgaaga tccctc                                36

<210> SEQ ID NO 52
<211> LENGTH: 36
<212> TYPE: DNA
<213> ORGANISM: Homo sapiens

<400> SEQUENCE: 52
gcagcagtcg acttcattgt gctggacatc ctttct                                36
```

ANTIBODY DIRECTED TO HUMAN MIST (MAST CELL IMMUNORECEPTOR SIGNAL TRANSDUCER)

This application is a divisional application of non-provisional application U.S. Ser. No. 11/640,775, filed Dec. 18, 2006, which is a divisional application of non-provisional application U.S. Ser. No. 09/966,955, filed Sep. 28, 2001, now U.S. Pat. No. 7,241,590, which claims benefit to provisional application U.S. Ser. No. 60/237,030 filed Sep. 29, 2000, under 35 U.S.C. 119(e).

FIELD OF THE INVENTION

The invention relates to the identification and cloning of a novel full-length human MIST gene and its encoded polypeptide product, MIST (Mast Cell Immunoreceptor Signal Transducer), which contains a SH2 (Src homology 2) domain. By homology analysis, MIST is a member of the SLP-76 family of adapter proteins w are expressed exclusively in cells of hematopoietic origin. The invention further relates to the use of the novel gene and encoded product as targets for therapeutic intervention in immune cell disorders and inflammatory indications.

BACKGROUND OF THE INVENTION

Receptor signaling pathways and intracellular signaling by receptor tyrosine kinases are intimately involved in cell growth and differentiation. The binding of a particular growth factor or cellular ligand to its receptor on a cell's plasma membrane can stimulate a wide variety of biochemical responses, including changes in ion fluxes, activation of various kinases, alteration of cell shape, transcription of various genes and modulation of enzymatic activities in cellular metabolism.

Many cell receptors are tyrosine kinases whose signaling is dependent upon tyrosine phosphorylation of both the receptor and other molecules. Specific phosphorylated tyrosine residues on these receptors recruit soluble intracellular signaling molecules to the receptor-ligand complex upon extracellular ligand stimulation, thus initiating the intracellular signaling cascade that involves secondary signal transducer molecules generated by the activated receptor. The signal can then proceed through a series of steps to the nucleus and other subcellular locations where the final effects of activation by the extracellular ligand are produced. Recruitment of other molecules in the signaling pathway is often accomplished by adapter molecules, which contain only protein-protein interaction domains (e.g., SH2 and SH3 domains) and have no associated enzymatic activity. By isolating and characterizing the adapter proteins and the molecules that interact with these adapters, important parts of the signaling mechanism can be discovered, monitored and controlled.

For example, one such adapter protein is Grb2, a 24-25 kDa cytosolic adapter protein containing two SH3 domains flanking an SH2 domain, which is known to be involved in linking many important molecules in receptor-ligand signal transduction (E. J. Lowenstein et al., 1992, Cell, 70:431-442 and J. Downward, 1994, FEBS Letters, 338:113-117). The central SH2 domain of Grb2 binds to an autophosphorylation site on the receptor and the two flanking SH3 domains link to intracellular effector target molecules. An example of one such target molecule is the mammalian homolog of the Drosophila 'son of sevenless' (SOS) protein, which is a guanine nucleotide exchange factor for ras; thus, Grb2 links receptors with the ras signal transduction pathway. It is now known that the SH3 domains also link to a number of other proteins involved in the signaling pathway, including Vav (R. Ren et al., 1994, Genes Dev., 8:783-795; J. Wu et al., 1996, Immunity, 4:593; and L. Tuosto et al., 1996, J. Exp. Med., 184:1161); c-abl (Z. S. Ye and D. Baltimore, 1994, Proc. Nat'l. Acad. Sci. USA, 91:12629-12633); dynamin (I. Gout et al., 1993, Cell, 75:25-36); and SLP-76 (J. K. Jackman et al., 1995, J. Biol. Chem., 270:7029-7032). In addition, several other binding proteins have been noted during B- and T-cell signaling (See, e.g., K. Reif et al., 1994, J. Biol. Chem., 269:14081-14087 and D. G. Motto et al., 1994, J. Biol. Chem., 269:21608-21613).

The SLP-76 family of adapter protein molecules includes the SLP-76, BLNK and Clnk proteins (P. S. Myung et al., 2000, "Adapter proteins in lymphocyte antigen-receptor signaling", Curr. Opin. Immunol., 12:256-266 and M. Y. Cao et al., 1999, "Clnk, a novel SLP-76-related adapter molecule expressed in cytokine-stimulated hemopoietic cells", J. Exp. Med., 190:1527-1534). Expressed exclusively in cells of hematopoietic origin, these adapter proteins are involved in intracellular signal transduction. SLP-76 is an SH2 domain-containing 76 kDa leukocyte protein that undergoes tyrosine phosphorylation following activation of the T-cell antigen receptor (TCR). SLP-76, upon tyrosine phosphorylation, interacts with Grb2 and phospholipase C-□ (PLC-□), (J. K. Jackman et al., supra). The phosphorylation of SLP-76 on tyrosine is required for TCR-mediated cytokine secretion.

SH2 domain-containing proteins bind phosphorylated tyrosine residues and transmit important intracellular signals in many cell types. In the immune system, SH2 domain-containing proteins, such as SLP-76 and BLNK, play crucial roles in T-cell and B-cell activation. Therefore, SH2 domain-containing proteins are likely to be important targets for therapeutic intervention in immunological disorders, including autoimmune disorders and inflammatory indications. In addition, a partial sequence containing only a middle portion of a MIST/Clnk protein isolated by R. Goitsuka et al. (2000, Int. Immunol., 12:573-580) was implicated as being involved in receptor-mediated mast cell degranulation, thus providing another type of hematopoietic cell in which such SH2-domain-containing proteins function to transmit intracellular signals.

With particular regard to B-cells, cell function is dependent on the ability of the membrane B-cell receptor (BCR) to bind to antigen and induce an efficient cascade of intracellular biochemical signaling events from the membrane to the nucleus. These events culminate in the cytosol to rearrange the morphology of the cell through cytoskeletal reorganization and in the nucleus to activate the transcription of new genes to promote cellular proliferation and differentiation. Such biochemical and cellular mechanisms are required for B-cells to mature and function to produce an efficient immune response to foreign pathogens. Conversely, the abnormal activation of B-cells can lead to unregulated cellular proliferation and uncontrolled clonal expansion, resulting in B-cell tumors, lymphomas and leukemias. In addition, unregulated activation of B-cells may also contribute to a variety of autoimmune diseases mediated by self-reactive antibodies.

Similarly, in the case of T-cells, unregulated activation of the TCR can lead to aberrant T-cell growth, resulting in, for example, T-cell tumors, lymphomas, leukemias and thymomas. Thus, the ability to modulate TCR- and BCR-mediated signaling events may provide a rational approach to the treatment of T- and B-cell mediated tumors, and the like, as well as provide therapies for autoimmune diseases in which aberrant B-cell activation may be the culprit for cell destruction by auto-reactive antibodies.

Because aberrant or uncontrolled regulation of the cellular processes involved in cell growth can have disastrous effects, it is important to elucidate and gain control over these processes. This requires identifying molecules that participate in the signaling events that lead to mitogenesis and dissecting their functions and mechanisms of action. The identification of these participants is important for a wide range of diagnostic, therapeutic and screening applications. More specifically, by knowing the structure of a particular participant in a receptor ligand activation cascade, one can rationally design compounds that affect that cascade, to either activate an otherwise inactive pathway, or inactivate an overly active pathway.

Similarly, having identified a particular molecule in a ligand receptor cascade, situations in which that cascade is defective can also be identified and intervention can be achieved by means of therapeutic compounds or drugs, to prevent the development of a particular pathological state. The identification of participants in particular receptor ligand activation cascades and intracellular signaling events is thus of critical importance for screening compounds that affect these cascades and events, and treating a variety of disorders resulting from anomalies in these cascades and events as therapeutic agents. The present invention meets these and many other needs.

In addition, the discovery of human MIST, a new member of the SLP-76 family of adapter proteins, and the polynucleotide encoding this protein provides the art with new compositions and methods of use and treatment for the diagnosis, screening, monitoring, therapy, and prevention of immune system related conditions or diseases, particularly those involving T-cell and B-cell neoplasms, and inflammation disorders, diseases and conditions, particularly those involving hyperactivity of B-cells and T-cells, or other immune cells, such as mast cells or eosinophils.

SUMMARY OF THE INVENTION

The present invention provides a newly discovered full-length human SH2-domain containing gene and its encoded product, called MIST (Mast Cell Immunoreceptor Signal Transducer), which has homology with the adapter proteins SLP-76 (SH2 domain-containing Leukocyte-specific Phosphoprotein of 76 kDa), Clnk (cytokine-dependent hematopoietic cell linker protein) and BLNK (B cell Linker Protein).

It is an object of the present invention to provide an isolated full-length MIST polynucleotide as depicted in SEQ ID NO:1. The present invention also provides a polynucleotide sequence comprising the complement of SEQ ID NO:1, or variants thereof. In addition, the present invention features polynucleotide sequences which hybridize under moderate or high stringency conditions to the polynucleotide sequence of SEQ ID NO:1.

It is another object of the present invention to provide the human MIST polypeptide, encoded by the polynucleotide of SEQ ID NO:1 and having the amino acid sequence of SEQ ID NO:2, or a functional or biologically active portion thereof. In accordance with the present invention, an isolated, substantially purified full-length human MIST protein is provided.

It is another object of the present invention to provide novel splice variants of the MIST protein. According to the invention, the full-length polynucleotide sequence of a first alternatively spliced form of the human MIST cDNA (SEQ ID NO:3) and its encoded polypeptide (SEQ ID NO:4) are provided. Also provided is the full-length polynucleotide sequence of a second alternatively spliced form of the human MIST cDNA (SEQ ID NO:5) and its encoded polypeptide (SEQ ID NO:6).

It is a further object of the present invention to provide compositions comprising the human MIST polynucleotide sequence, or a fragment thereof, or the encoded MIST polypeptide, or a fragment or portion thereof. Also in accordance with the present invention are provided pharmaceutical compositions comprising at least one MIST polypeptide, or a functional portion thereof, wherein the compositions further comprise a pharmaceutically acceptable carrier, excipient, or diluent.

It is yet another object of the present invention to provide an antisense of the human MIST nucleic acid sequence, as well as oligonucleotides, fragments, or portions of the MIST nucleic acid molecule or antisense molecule. Also provided are expression vectors and host cells comprising polynucleotides that encode the human MIST polypeptide, or portions or fragments thereof.

Yet another object of the present invention is to provide methods for producing a polypeptide comprising the amino acid sequence depicted in SEQ ID NO:2, or a fragment thereof, comprising the steps of a) cultivating a host cell containing an expression vector containing at least a functional fragment of the polynucleotide sequence encoding the human MIST polypeptide according to this invention under conditions suitable for the expression of the polynucleotide; and b) recovering the polypeptide from the host cell.

It is a further object of the present invention to provide antibodies, and binding fragments thereof, which bind specifically to the MIST polypeptide, or an epitope thereof, for use as therapeutics, for example, when linked to a cell-permeable peptide ligand, and diagnostic agents.

It is another object of the present invention to provide methods for screening for agents or molecules which bind to and/or modulate human MIST polypeptide, e.g., inhibitors, other intracellular signaling molecules and antagonists, as well as the modulators, particularly, inhibitors and antagonists, particularly those that are obtained from the screening methods described. Also provided are methods to screen for inhibitors of the interaction, e.g., a binding interaction, of the MIST protein with other signaling proteins, particularly those having SH2 and SH3 interaction domains.

It is a further object of the present invention to provide a substantially purified antagonist or inhibitor of the polypeptide of SEQ ID NO:2. In this regard, and by way of example, a purified antibody that binds to a polypeptide comprising the amino acid sequence of SEQ ID NO:2 is provided.

It is another object of the present invention to provide MIST nucleic acid sequences, polypeptide, peptides and antibodies for use in the diagnosis and/or screening of disorders or diseases associated with expression of the polynucleotide and its encoded polypeptide as described herein.

It is another object of the present invention to provide kits for screening and diagnosis of disorders associated with aberrant or uncontrolled cellular development and with the expression of the MIST polynucleotide and its encoded polypeptide as described herein.

It is a further object of the present invention to provide methods for the treatment or prevention of immune cell disorders or diseases, e.g., B- or T-cell tumors, lymphomas, leukemias, or autoimmune diseases, involving administering to an individual in need of treatment or prevention an effective amount of a purified antagonist of the MIST polypeptide.

It is yet another object of the present invention to provide a method for detecting a polynucleotide that encodes the MIST polypeptide in a biological sample comprising the steps of: a) hybridizing the complement of the polynucleotide sequence encoding SEQ ID NO:2 to a nucleic acid material of a biological sample, thereby forming a hybridization complex; and b) detecting the hybridization complex, wherein the presence of the complex correlates with the presence of a polynucleotide encoding the MIST polypeptide in the biological sample. The nucleic acid material may be further amplified by the polymerase chain reaction prior to hybridization.

Further objects, features and advantages of the present invention will be better understood upon a reading of the detailed description of the invention when considered in connection with the accompanying figures/drawings.

BRIEF DESCRIPTION OF THE FIGURES

FIGS. 1A-1B show the full-length polynucleotide sequence of human MIST cDNA (clone #8) of the present invention (SEQ ID NO:1). The coding sequence (CDS) of MIST clone #8 is 320 to 1648 of SEQ ID NO:1.

Figure 2:
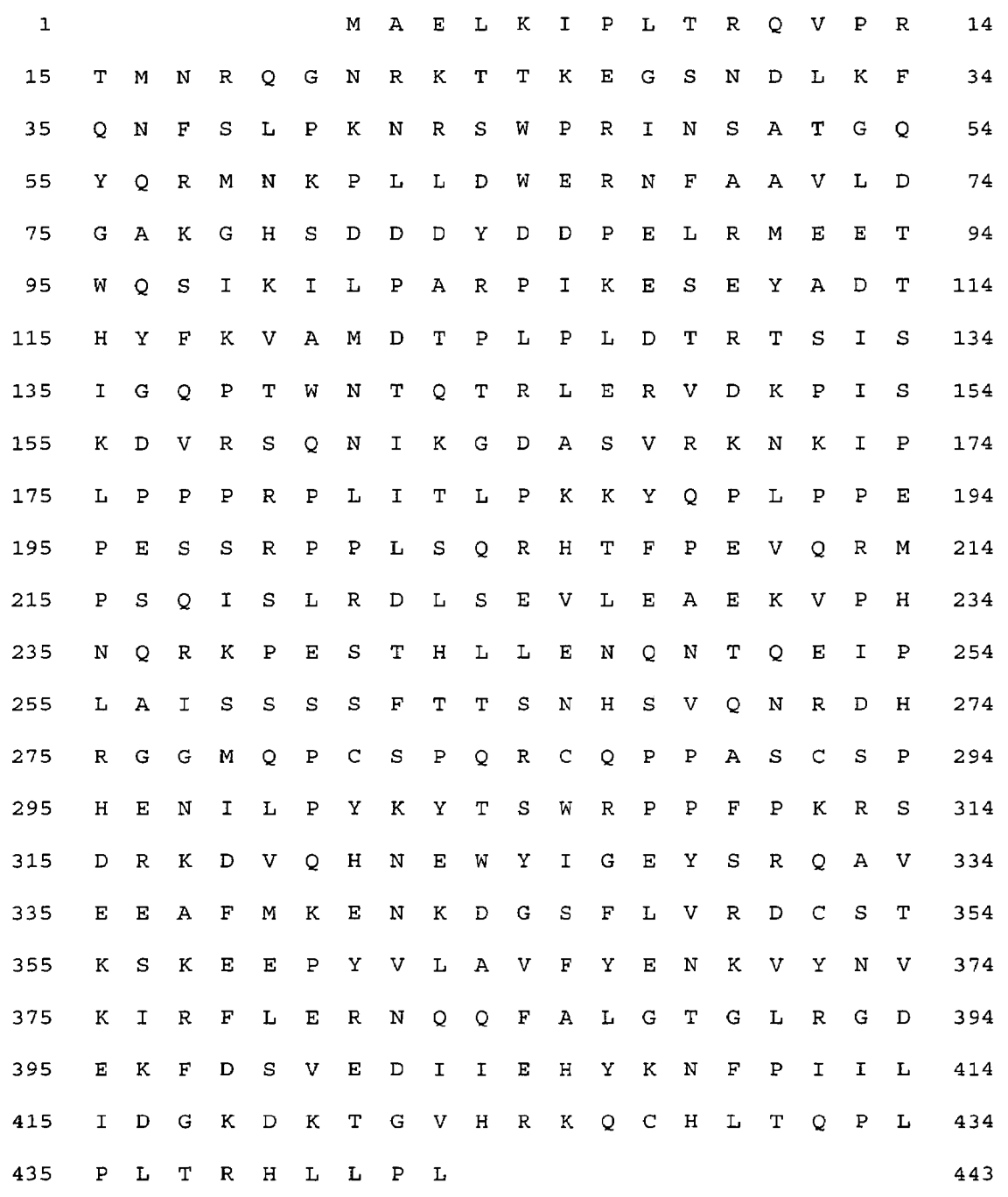

FIG. 2 shows the amino acid sequence comprising the MIST polypeptide (SEQ ID NO:2) encoded by the polynucleotide of SEQ ID NO:1. The predicted molecular weight of the MIST polypeptide encoded by the polynucleotide of clone #8 is MW=51.3 Kd.

FIGS. 3A-3B show the nucleic acid sequence of human MIST cDNA (SEQ ID NO:1), and the deduced, encoded amino acid sequence of the human MIST gene product (SEQ ID NO:2). Putative tyrosine phosphorylation sites are marked with arrows. Putative SH3 binding proline-rich motifs (PXXP) are in bold and italics. The SH2 domain is underlined.

FIGS. 4A-B show the full-length polynucleotide sequence of an alternatively spliced form of the human MIST cDNA (clone #7), i.e., the MIST clone #7 splice variant, of the present invention (SEQ ID NO:3). The coding sequence (CDS) of MIST clone #7 is 261 to 1544 of SEQ ID NO:3.

Figure 5:
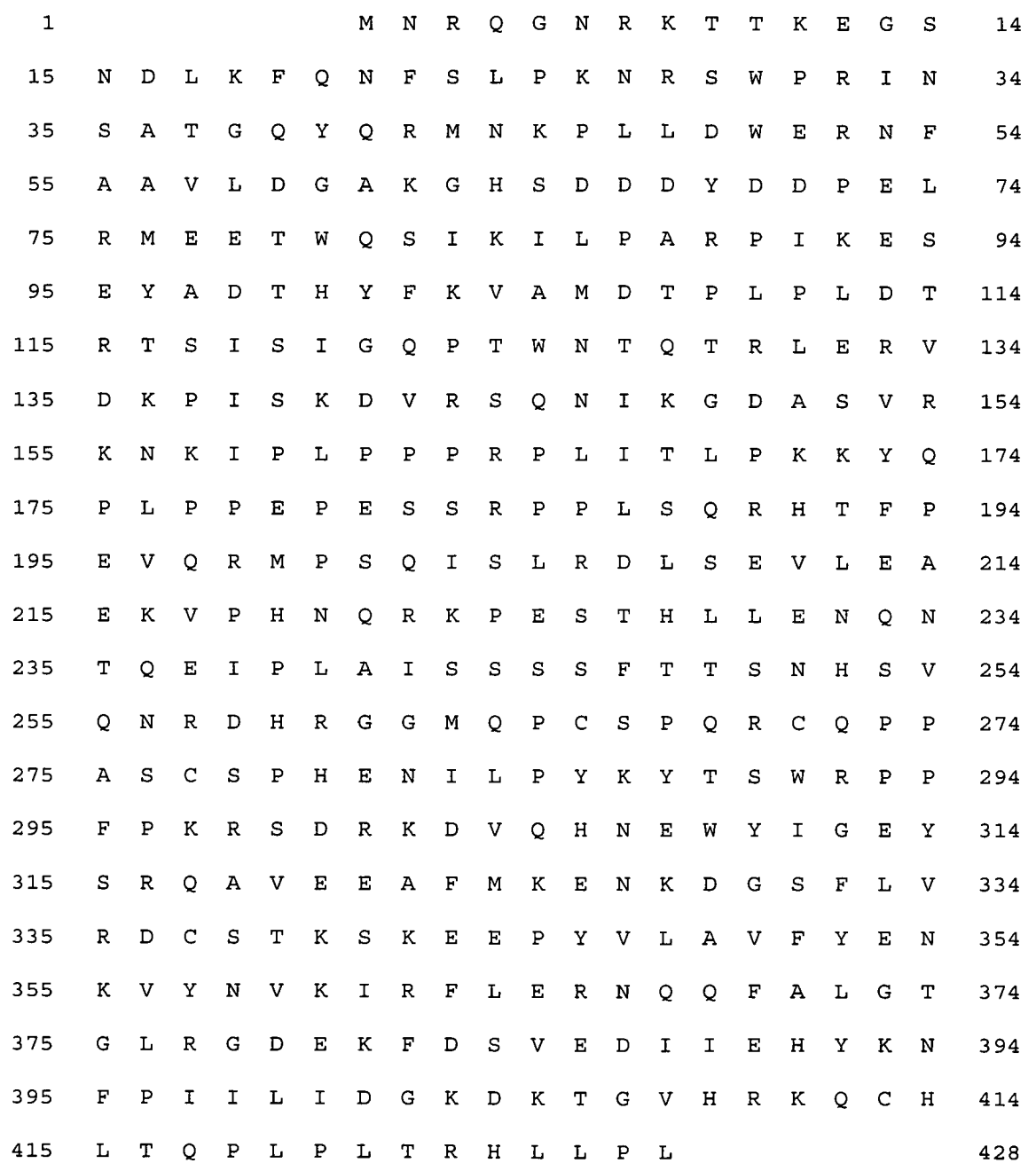

FIG. 5 shows the amino acid sequence comprising the MIST clone #7 splice variant polypeptide (SEQ ID NO:4) encoded by the polynucleotide of SEQ ID NO:3. The predicted molecular weight of the MIST polypeptide encoded by the polynucleotide of clone #7 is MW=49.6 Kd.

FIGS. 6A-6B show the nucleic acid sequence of the human MIST clone #7 splice variant cDNA (SEQ ID NO:3), and the deduced, encoded amino acid sequence of the human MIST clone #7 splice variant gene product (SEQ ID NO:4).

FIGS. 7A-7B show the full-length polynucleotide sequence of an alternatively spliced form of the human MIST cDNA (clone #12), i.e., the MIST clone #12 splice variant, of the present invention (SEQ ID NO:5). The coding sequence (CDS) of MIST clone #12 is 691 to 1749 of SEQ ID NO:5.

FIG. 8 shows the amino acid sequence comprising the MIST clone #12 splice variant polypeptide (SEQ ID NO:6) encoded by the polynucleotide of SEQ ID NO:5. The predicted molecular weight of the MIST polypeptide encoded by the polynucleotide of clone #12 is MW=40.8 Kd.

FIGS. 9A-9B show the nucleic acid sequence of the human MIST clone #12 splice variant cDNA (SEQ ID NO:5), and the deduced, encoded amino acid sequence of the human MIST clone #12 splice variant gene product (SEQ ID NO:6).

FIG. 10 presents the structural features of human MIST. Domain structures include the sterile alpha motif (SAM), putative tyrosine phosphorylation sites (Y), proline-rich motif (PXXP) and the Src homology 2 (SH2) domain.

FIG. 14 presents the results of binding assays showing the binding of MIST-SH2-1 g to a phosphopeptide derived from the sequence of human SLP-76 (DDpYESPND), (SEQ ID NO:7). SH2-Ig fusion proteins were added to plates preincubated with phosphopeptide (4 µg/ml) at descending concentrations starting at 1 µg/ml. Ig fusion proteins were detected with HRP-conjugated anti-Ig and were detected using an ELISA kit. (Example 2).

In FIG. 15A, equivalent amounts of whole cell lysates from the indicated cell lines were analyzed by SDS-PAGE gradient (4-20% gels) under reducing conditions and subsequently probed with the anti MIST mAb #45 at 1 g/ml and anti-mouse Ig-HRP (Example 11). In FIG. 15B $10^7$ RBL or HMC-1 cells were stimulated with pervanadate at 37° C. for the indicated time periods and lysed. MIST polypeptide was immunoprecipitated with the anti-MIST mAb #45 and probed with the anti-phosphotyrosine mAb 4G10-HRP (upper panels). The blots were subsequently stripped and reprobed with anti-MIST mAb #45 (bottom panels). In FIGS. 15A and 15B, "IP" denotes "immunoprecipitation" and "IB" denotes "immunoblot".

DETAILED DESCRIPTION OF THE INVENTION

Figure 11:
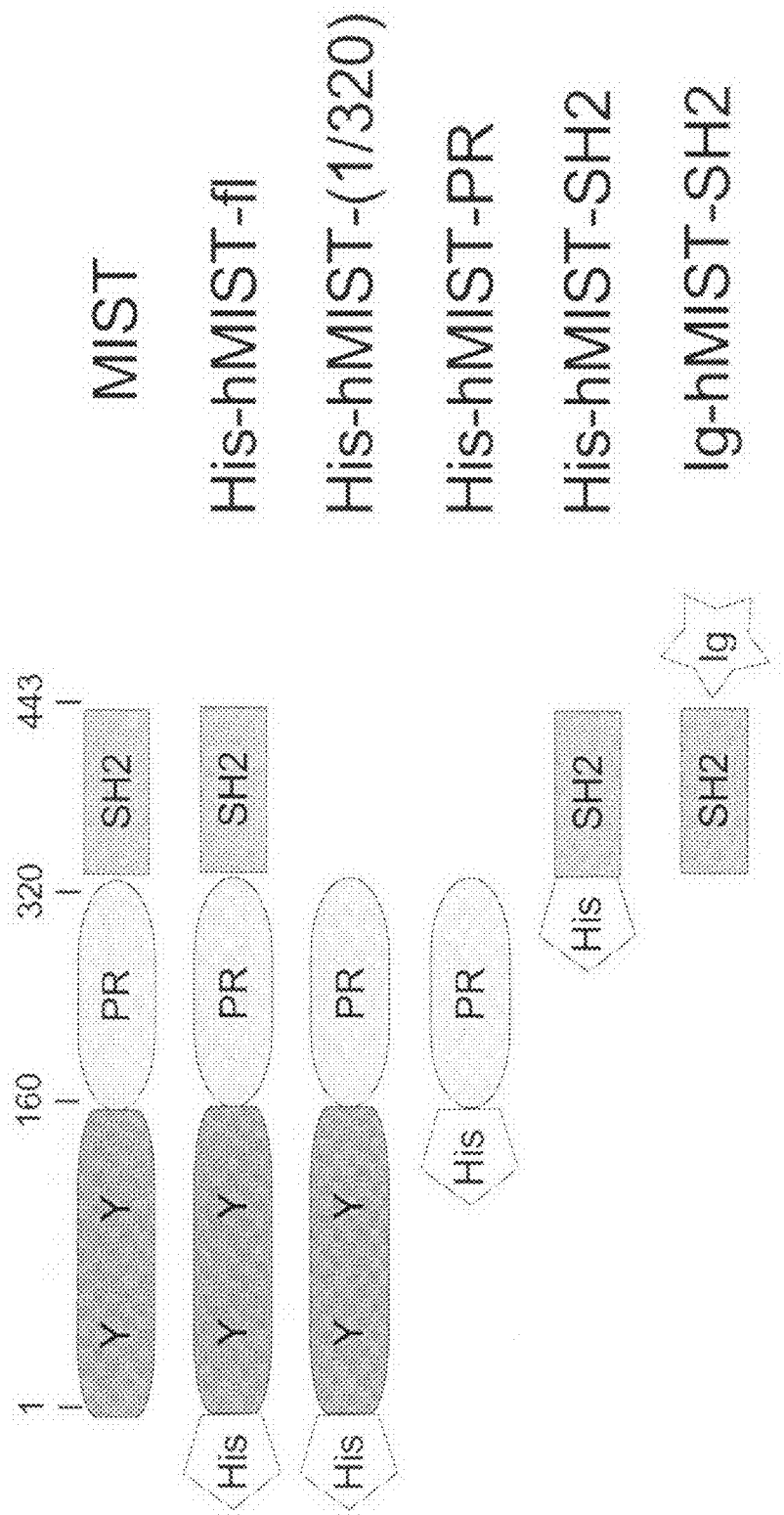
FIG. 11 presents a schematic representation of recombinant MIST proteins, produced from several poly-His-tagged MIST constructs and a MIST-SH2 fusion construct. The full-length (fl), proline-rich (PR), and SH2 domains from human MIST cDNA were cloned into an expression vector linked to a poly-His tag (His), or to the $C_H$ region of human immunoglobulin (Ig) IgG2a. Proteins were expressed in Sf9 cells or in COS cells, followed by purification on TALON® resin (His), or protein A SEPHAROSE® (Ig) according to established methods.

The present invention provides a novel isolated polynucleotide (SEQ ID NO:1) encoding the full-length MIST polypeptide (SEQ ID NO:2), a protein having similarity at the amino acid level to other SH2-domain containing adapter proteins which function in the receptor-ligand signal transduction pathway in cells of the hematopoietic lineage.

The following definitions are provided to more fully describe the present invention in its various aspects. The definitions are intended to be useful for guidance and elucidation, and are not intended to limit the disclosed invention and its embodiments.

DEFINITIONS

The MIST polypeptide (or protein) refers to the amino acid sequence of substantially purified MIST, which, although isolated from a human cDNA library source according to the present invention, may be obtained from any species, preferably mammalian, including mouse, rat, non-human primates, and more preferably, human; and from a variety of sources, including natural, synthetic, semi-synthetic, or recombinant. Fragments and portions of the MIST polypeptide, preferably functional fragments of the MIST polypeptide, are also embraced by the present invention.

An agonist (or activator) refers to a molecule which, when bound to the MIST polypeptide, or a functional fragment thereof, increases or prolongs the duration of the effect of the MIST polypeptide. Agonists may include proteins, nucleic acids, carbohydrates, or any other molecules that bind to and modulate the effect of MIST polypeptide. An antagonist (e.g., inhibitor or blocker) refers to a molecule which, when bound to the MIST polypeptide, or a functional fragment thereof, decreases or eliminates the amount or duration of the biological or immunological activity of MIST polypeptide. Antagonists may include proteins, nucleic acids, carbohydrates, antibodies, or any other molecules that decrease, reduce or eliminate the effect of the MIST polypeptide.

"Nucleic acid sequence", as used herein, refers to an oligonucleotide, nucleotide, or polynucleotide, and fragments or portions thereof, and to DNA or RNA of genomic or synthetic origin which may be single- or double-stranded, and represent the sense or antisense strand. By way of nonlimiting example, fragments include nucleic acid sequences that are greater than 20-60 nucleotides in length, and preferably include fragments that are at least 70-100 nucleotides, or which are at least 1000 nucleotides or greater in length. Nucleic acids for use as probes or primers may differ in length as described herein.

Similarly, "amino acid sequence" as used herein refers to an oligopeptide, peptide, polypeptide, or protein sequence, and fragments or portions thereof, and to naturally occurring or synthetic molecules. Amino acid sequence fragments are typically from about 4 or 5 to about 35, preferably from about 5 to about 15 or 20 amino acids in length and, optimally, retain the biological activity or function of the MIST polypeptide.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule. In addition, the terms MIST polypeptide and MIST protein are frequently used interchangeably herein to refer to the encoded product of the MIST nucleic acid sequence of the present invention.

A variant of the MIST polypeptide can refer to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Minor variations may also include amino acid deletions or insertions, or both. Guidance in determining which amino acid residues may be substituted, inserted, or deleted without abolishing functional biological or immunological activity may be found using computer programs well known in the art, for example, DNASTAR® software.

An allele or allelic sequence is an alternative form of the MIST nucleic acid sequence. Alleles may result from at least one mutation in the nucleic acid sequence and may yield altered mRNAs or polypeptides whose structure or function may or may not be altered. Any given gene, whether natural or recombinant, may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Altered nucleic acid sequences encoding the MIST polypeptide include nucleic acid sequences containing deletions, insertions and/or substitutions of different nucleotides resulting in a polynucleotide that encodes the same or a functionally equivalent MIST polypeptide. Altered nucleic acid sequences may further include polymorphisms of the polynucleotide encoding the MIST polypeptide; such polymorphisms may or may not be readily detectable using a particular oligonucleotide probe. The encoded protein may also contain deletions, insertions, or substitutions of amino acid residues which produce a silent change and result in a functionally equivalent MIST protein of the present invention. Deliberate amino acid substitutions may be made on the basis of similarity in polarity, charge, solubility, hydrophobicity, hydrophilicity, and/or the amphipathic nature of the residues, as long as the biological activity or function of MIST protein is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; and phenylalanine and tyrosine.

"Peptide nucleic acid" (PNA) represents an oligomer of modified nucleic acid base pairs covalently linked through an amide bond. PNAs have utility in a number of antisense and anti-gene applications. These small molecules typically act by inhibiting transcription. (e.g., P. E. Nielsen et al., 1993, Anticancer Drug Des., 8:53-63). PNA may be pegylated to extend their lifespan in the cell where they preferentially bind to complementary single stranded DNA and RNA.

Oligonucleotides or oligomers refer to a nucleic acid sequence, preferably comprising contiguous nucleotides, of at least about 6 nucleotides to about 60 nucleotides, preferably at least about 8 to 10 nucleotides in length, more preferably at least about 12 nucleotides in length, e.g., about 15 to 35 nucleotides, or about 15 to 25 nucleotides, or about 20 to 35 nucleotides, which can be typically used, for example, as probes or primers, in PCR amplification assays, hybridization assays, or in microarrays. It will be understood that the term oligonucleotide is substantially equivalent to the terms primer, probe, or amplimer, as commonly defined in the art. It will also be appreciated by those skilled in the pertinent art that a longer oligonucleotide probe, or mixtures of probes, e.g., degenerate probes, can be used to detect longer, or more complex, nucleic acid sequences, for example, genomic DNA. In such cases, the probe may comprise at least 20-200 nucleotides, preferably, at least 30-100 nucleotides, more preferably, 50-100 nucleotides.

Amplification refers to the production of additional copies of a nucleic acid sequence and is generally carried out using polymerase chain reaction (PCR) technologies, which are well known and practiced in the art (See, D. W. Dieffenbach and G. S. Dveksler, 1995, PCR Primer, a Laboratory Manual, Cold Spring Harbor Press, Plainview, N.Y.).

Microarray is an array of distinct polynucleotides or oligonucleotides synthesized on a substrate, such as paper, nylon, or other type of membrane; filter; chip; glass slide; or any other type of suitable solid support.

The term antisense refers to nucleotide sequences, and compositions containing nucleic acid sequences, which are complementary to a specific DNA or RNA sequence. The term "antisense strand" is typically used in reference to a nucleic acid strand that is complementary to the "sense" strand. Antisense (i.e., complementary) nucleic acid molecules include PNA and may be produced by any method, including synthesis or transcription. Once introduced into a cell, complementary nucleotides can combine with natural sequences produced by the cell to form duplexes which can block either transcription or translation. The designation "negative" is sometimes used in reference to the antisense strand, and "positive" is sometimes used in reference to the sense strand.

The term consensus typically refers to a nucleic acid sequence which has been re-sequenced to resolve uncalled bases, or which has been extended using XL-PCR (Perkin Elmer, Norwalk, Conn.) in the 5' and/or the 3' direction and resequenced, or which as been assembled from the overlapping sequences of more than one Incyte clone or publicly available clone using the GELVIEW® Fragment Assembly system (GCG, Madison, Wis.), or other assembly procedures, or which has been both extended and assembled.

A deletion refers to a change in either nucleotide or amino acid sequence and results in the absence of one or more nucleotides or amino acid residues. By contrast, an insertion (also termed "addition") refers to a change in a nucleotide or amino acid sequence that results in the addition of one or more nucleotides or amino acid residues, as compared with the naturally occurring molecule. A substitution refers to the replacement of one or more nucleotides or amino acids by different nucleotides or amino acids.

A derivative nucleic acid molecule refers to the chemical modification of a nucleic acid encoding, or complementary to, the encoded MIST polypeptide. Such modifications include, for example, replacement of hydrogen by an alkyl, acyl, or amino group. A nucleic acid derivative encodes a polypeptide which retains the essential biological and/or functional characteristics of the natural molecule. A derivative polypeptide is one which is modified by glycosylation, pegylation, or any similar process that retains the biological and/or functional or immunological activity of the polypeptide from which it is derived.

The term "biologically active", i.e., functional, refers to a protein or polypeptide or peptide fragment thereof having structural, regulatory, or biochemical functions of a naturally occurring molecule. Likewise, "immunologically active" refers to the capability of the natural, recombinant, or synthetic MIST, or any oligopeptide thereof, to induce a specific humoral and/or cellular immune response in appropriate animals or cells, for example, to generate antibodies, and to bind with specific antibodies.

The term hybridization refers to any process by which a strand of nucleic acid binds with a complementary strand through base pairing.

The term "hybridization complex" refers to a complex formed between two nucleic acid sequences by virtue of the formation of hydrogen bonds between complementary G and C bases and between complementary A and T bases. The hydrogen bonds may be further stabilized by base stacking interactions. The two complementary nucleic acid sequences hydrogen bond in an anti-parallel configuration. A hybridization complex may be formed in solution (e.g., $C_o t$ or $R_o t$ analysis), or between one nucleic acid sequence present in solution and another nucleic acid sequence immobilized on a solid support (e.g., membranes, filters, chips, pins, or glass slides, or any other appropriate substrate to which cells or their nucleic acids have been affixed).

The terms stringency or stringent conditions refer to the conditions for hybridization as defined by nucleic acid composition, salt and temperature. These conditions are well known in the art and may be altered to identify and/or detect identical or related polynucleotide sequences in a sample. A variety of equivalent conditions comprising either low, moderate, or high stringency depend on factors such as the length and nature of the sequence (DNA, RNA, base composition), reaction milieu (in solution or immobilized on a solid substrate), nature of the target nucleic acid (DNA, RNA, base composition), concentration of salts and the presence or absence of other reaction components (e.g., formamide, dextran sulfate and/or polyethylene glycol) and reaction temperature (within a range of from about 5° C. below the melting temperature of the probe to about 20° C. to 25° C. below the melting temperature). One or more factors may be varied to generate conditions, either low or high stringency, that are different from but equivalent to the aforementioned conditions.

As will be understood by those of skill in the art, the stringency of hybridization may be altered in order to identify or detect identical or related polynucleotide sequences. As will be further appreciated by the skilled practitioner, Tm can be approximated by the formulas as known in the art, depending on a number of parameters, such as the length of the hybrid or probe in number of nucleotides, or hybridization buffer ingredients and conditions (See, for example, T. Maniatis et al., *Molecular Cloning: A Laboratory Manual*, Cold Spring Harbor Laboratory, Cold Spring Harbor, N.Y., 1982 and J. Sambrook et al., *Molecular Cloning: A Laboratory Manual*, Cold Spring Harbor Laboratory, Cold Spring Harbor, N.Y., 1989; *Current Protocols in Molecular Biology*, Eds. F. M. Ausubel et al., Vol. 1, "Preparation and Analysis of DNA", John Wiley and Sons, Inc., 1994-1995, Suppls. 26, 29, 35 and 42; pp. 2.10.7-2.10.16; G. M. Wahl and S. L. Berger (1987; *Methods Enzymol.* 152:399-407); and A. R. Kimmel, 1987; *Methods of Enzymol.* 152:507-511). As a general guide, Tm decreases approximately 1° C.-1.5° C. with every 1% decrease in sequence homology. Also, in general, the stability of a hybrid is a function of sodium ion concentration and temperature. Typically, the hybridization reaction is initially performed under conditions of low stringency, followed by washes of varying, but higher stringency. Reference to hybridization stringency, e.g., high, moderate, or low stringency, typically relates to such washing conditions.

Thus, by way of nonlimiting example, high stringency refers to conditions that permit hybridization of those nucleic acid sequences that form stable hybrids in 0.018M NaCl at about 65° C. (i.e., if a hybrid is not stable in 0.018M NaCl at about 65° C., it will not be stable under high stringency conditions). High stringency conditions can be provided, for instance, by hybridization in 50% formamide, 5× Denhart's solution, 5×SSPE (saline sodium phosphate EDTA) (1×SSPE buffer comprises 0.15 M NaCl, 10 mM $Na_2HPO_4$, 1 mM EDTA), (or 1×SSC buffer containing 150 mM NaCl, 15 mM $Na_3$ citrate.$2H_2O$, pH 7.0), 0.2% SDS at about 42° C., followed by washing in 1×SSPE (or saline sodium citrate, SSC) and 0.1% SDS at a temperature of at least about 42° C., preferably about 55° C., more preferably about 65° C.

Moderate stringency refers, by nonlimiting example, to conditions that permit hybridization in 50% formamide, 5× Denhart's solution, 5×SSPE (or SSC), 0.2% SDS at 42° C. (to about 50° C.), followed by washing in 0.2×SSPE (or SSC) and 0.2% SDS at a temperature of at least about 42° C., preferably about 55° C., more preferably about 65° C.

Low stringency refers, by nonlimiting example, to conditions that permit hybridization in 10% formamide, 5× Denhart's solution, 6×SSPE (or SSC), 0.2% SDS at 42° C., followed by washing in 1×SSPE (or SSC) and 0.2% SDS at a temperature of about 45° C., preferably about 50° C.

For additional stringency conditions, see T. Maniatis et al., *Molecular Cloning: A Laboratory Manual*, Cold Spring Harbor Laboratory, Cold Spring Harbor, N.Y. (1982). It is to be understood that the low, moderate and high stringency hybridization/washing conditions may be varied using a variety of ingredients, buffers and temperatures well known to and practiced by the skilled practitioner.

The terms complementary or complementarity refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between single stranded molecules. The degree of complementarity between nucleic acid strands has significant effects on the efficiency and strength of hybridization between nucleic acid strands. This is of particular importance in amplification reactions, which depend upon binding between nucleic acids strands, as well as in the design and use of PNA molecules.

The term homology refers to a degree of complementarity. There may be partial sequence homology or complete homology, wherein complete homology is equivalent to identity, e.g., 100% identity. A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (e.g., Southern or Northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. Nonetheless, conditions of low stringency do not permit non-specific binding; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Those having skill in the art will know how to determine percent identity between/among sequences using, for example, algorithms such as those based on the CLUSTALW computer program (J. D. Thompson et al., 1994, *Nucleic Acids Research*, 2(22):4673-4680), or FASTDB, (Brutlag et al., 1990, *Comp. App. Biosci.*, 6:237-245), as known in the art. Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations.

A composition comprising a given polynucleotide sequence refers broadly to any composition containing the given polynucleotide sequence. The composition may comprise a dry formulation or an aqueous solution. Compositions comprising polynucleotide sequence (SEQ ID NO:1) encoding MIST polypeptide, or fragments thereof, may be employed as hybridization probes. The probes may be stored in freeze-dried form and may be in association with a stabilizing agent such as a carbohydrate. In hybridizations, the probe may be employed in an aqueous solution containing salts (e.g., NaCl), detergents or surfactants (e.g., SDS) and other components (e.g., Denhardt's solution, dry milk, salmon sperm DNA, and the like).

The term "substantially purified" refers to nucleic acid sequences or amino acid sequences that are removed from their natural environment, i.e., isolated or separated by a variety of means, and are at least 60% free, preferably 75% to 85% free, and most preferably 90% or greater free from other components with which they are naturally associated.

The term sample, or biological sample, is meant to be interpreted in its broadest sense. A biological sample suspected of containing nucleic acid encoding the MIST protein, or fragments thereof, or the MIST protein itself, may comprise a body fluid, an extract from cells or tissue, chromosomes isolated from a cell (e.g., a spread of metaphase chromosomes), organelle, or membrane isolated from a cell, a cell, nucleic acid such as genomic DNA (in solution or bound to a solid support such as for Southern analysis), RNA (in solution or bound to a solid support such as for Northern analysis), cDNA (in solution or bound to a solid support), a tissue, a tissue print and the like.

Transformation refers to a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and partial bombardment. Such "transformed" cells include stably transformed cells in which the inserted DNA is capable of replication either as an autonomously replicating plasmid or as part of the host chromosome. Transformed cells also include those cells which transiently express the inserted DNA or RNA for limited periods of time.

The term "mimetic" refers to a molecule, the structure of which is developed from knowledge of the structure of the MIST protein, or portions thereof, and as such, is able to effect some or all of the actions of the MIST protein.

The term "portion" with regard to a protein (as in "a portion of a given protein") refers to fragments or segments, for example, peptides, of that protein. The fragments may range in size from four or five amino acid residues to the entire amino acid sequence minus one amino acid. Thus, a protein "comprising at least a portion of the amino acid sequence of SEQ ID NO: 2" encompasses the full-length human MIST polypeptide, and fragments thereof.

The term antibody refers to intact molecules as well as fragments thereof, such as Fab, $F(ab')_2$, Fv, which are capable of binding an epitopic or antigenic determinant. Antibodies that bind to MIST polypeptides can be prepared using intact polypeptides or fragments containing small peptides of interest or prepared recombinantly for use as the immunizing antigen. The polypeptide or oligopeptide used to immunize an animal can be derived from the transition of RNA or synthesized chemically, and can be conjugated to a carrier protein, if desired. Commonly used carriers that are chemically coupled to peptides include bovine serum albumin (BSA), keyhole limpet hemocyanin (KLH), and thyroglobulin. The coupled peptide is then used to immunize the animal (e.g., a mouse, a rat, or a rabbit).

The term "humanized" antibody refers to antibody molecules in which amino acids have been replaced in the non-antigen binding regions in order to more closely resemble a human antibody, while still retaining the original binding capability, e.g., as described in U.S. Pat. No. 5,585,089 to C. L. Queen et al.

The term "antigenic determinant" refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to an antigenic determinants. An antigenic determinant may compete with the intact antigen (i.e., the immunogen used to elicit the immune response) for binding to an antibody.

The terms "specific binding" or "specifically binding" refer to the interaction between a protein or peptide and a binding molecule, such as an agonist, an antagonist, or an antibody. The interaction is dependent upon the presence of a particular structure (e.g., an antigenic determinant or epitope, or a structural determinant) of the protein that is recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody. In addition, the MIST protein of the present invention contains an SH2 domain that serves as an interacting region of MIST with other cellular proteins, putative tyrosine residues that may become phosphorylated and could bind to SH2 domains on other cellular proteins and an SH3 binding motif that may serve as a binding domain for other cellular proteins having an SH3 domain. (FIGS. 3A-3B).

The term "correlates with expression of a polynucleotide" indicates that the detection of the presence of ribonucleic acid that is similar to SEQ ID NO:1 by Northern analysis is indicative of the presence of mRNA encoding the MIST polypeptide in a sample and thereby correlates with expression of the transcript from the polynucleotide encoding the protein.

An alteration in the polynucleotide of SEQ ID NO:1 comprises any alteration in the sequence of the polynucleotides encoding the MIST polypeptide, including deletions, insertions, and point mutations that may be detected using hybridization assays. Included within this definition is the detection of alterations to the genomic DNA sequence which encodes the MIST polypeptide (e.g., by alterations in the pattern of restriction fragment length polymorphisms capable of hybridizing to SEQ ID NO:1), the inability of a selected fragment of SEQ ID NO:1 to hybridize to a sample of genomic DNA (e.g., using allele-specific oligonucleotide probes), and improper or unexpected hybridization, such as hybridization to a locus other than the normal chromosomal locus for the polynucleotide sequence encoding the MIST polypeptide (e.g., using fluorescent in situ hybridization (FISH) to metaphase chromosome spreads).

DESCRIPTION OF THE PRESENT INVENTION

The present invention is based on the discovery of a novel full-length human Src homology 2 (SH2) domain-containing gene and its encoded protein, called MIST, which was determined by homology analysis to be a member of the SLP-76 family of adapter proteins. The gene and encoded product according to the present invention are called MIST (Mast cell Immunoreceptor Signal Transducer) due to its similarity to a partial MIST sequence expressed in mast cells as reported by R. Goitsuka et al., supra.

MIST Polynucleotides and Polypeptides

The present invention encompasses the nucleic acid sequence (SEQ ID NO:1) encoding the full-length MIST polypeptide (SEQ ID NO:2) and the use of compositions comprising the MIST polynucleotide or polypeptide in methods for screening for antagonists or inhibitors of the interaction of MIST with cellular signaling components. Also encompassed by the invention is the use of the MIST nucleic acid sequence and the MIST polypeptide in methods for diagnosing, treating or preventing disorders or diseases associated with aberrant or uncontrolled cellular signal transduction or with hyperactive cells, particularly in cells of hematopoietic origin, including B- and T-lymphocytes, monocytes, mast cells and the like. Immune related diseases such as B- and T-lymphocyte tumors, lymphomas, and leukemias are particular targets for treatment by the present invention, including inhibitors of MIST polynucleotide and polypeptide function. In addition, the MIST gene and polypeptide are useful for determining those cellular signaling molecules which associate with MIST and which provide critical signals for cell activation, preferably, T-cell activation.

According to the present invention, nucleic acid encoding human MIST protein was first identified as a PCR product in a human spleen cDNA library and the full-length MIST gene was isolated, as described in Example 1.

In one of its embodiments, the present invention encompasses a polypeptide comprising the amino acid sequence of SEQ ID NO:2 as shown in FIG. 2. The human MIST polypeptide is 443 amino acids in length and shares amino acid sequence similarity to the SH2-domain-containing adapter proteins SLP-76, Clnk and BLINK as presented in Table 1.

TABLE 1

| Amino Acid Level | |
|---|---|
| Homology | Similarity/Identity |
| Hu MIST × Mu Clnk | 66.8%/62.5% |
| Hu MIST × Hu SLP-76 | 38.2%/32.6% |
| Hu MIST × Hu BLNK | 34.6%/26.0% |
| Hu SLP-76 × Hu BLNK | 39.0%/31.6% |

Table 1 shows the percent similarity/identity at the amino acid level between Human (Hu) MIST and Mouse (Mu)-derived CLNK protein; between Human MIST and Human SLP-76; between Human MIST and Human Clnk; and between Human SLP-76 and Human BLNK. The percent similarity and identity values were determined using the GAP® algorithm using default parameters (Genetics Computer Group suite of programs; Needleman and Wunsch, 1970, *J. Mol. Biol.*, 48:443-453). Gap parameters: Gap creation penalty: 8 and Gap extension penalty: 2. Based on the Table 1 data, human MIST is unlikely to be the human homologue of murine Clnk, but rather is determined to be a novel sequence from this family of adapter proteins.

The nucleotide and predicted amino acid sequences of the Clnk-related gene, MIST, of the present invention are similar to those of the published murine sequence of Clnk (M. Y. Cao et al., 1999, supra; EMBL/GENBANK®/DDBJ accession no. AF187819). MIST is also identical to a partial sequence of a related human homologue reported by R. Goitsuka et al., 2000, supra; EMBL/GENBANK®/DDBJ accession no. AB032369).

FIG. 10 portrays the structural similarities among MIST and SLP-76/BLNK proteins and their expression patterns. Clearly, the relatedness of the proteins is based more on their overall structure as compared with homology. Interestingly, MIST lacks the amino-terminal sterile alpha motif (SAM) domain, but contains the amino-terminal tyrosine residues (putative phosphorylation sites) as well as the two PXXP sites (putative SH3 binding sites). Most prominently, the carboxy-terminal SH2 domain is observed in all family members.

Variants of the MIST polypeptide are also encompassed by the present invention. A preferred MIST variant has at least 75 to 80%, more preferably at least 85 to 90%, and even more preferably at least 90% amino acid sequence identity to the amino acid sequence (SEQ ID NO:2) disclosed herein, and which retains at least one biological, immunological, or other functional characteristic or activity of the MIST polypeptide. Most preferred is a variant having at least 95% amino acid sequence identity to the amino acid sequence set forth in SEQ ID NO:2. An amino acid sequence variant of the MIST protein can be categorized into one or more of three classes:

substitutional, insertional, or deletional variants. Such variants are typically prepared by site-specific mutagenesis of nucleotides in the DNA encoding the MIST protein, using cassette or PCR mutagenesis, or other techniques that are well known and practiced in the art, to produce DNA encoding the variant. Thereafter, the DNA is expressed in recombinant cell culture as described herein. Variant MIST protein fragments having up to about 100-150 residues may be prepared by in vitro synthesis using conventional techniques.

Amino acid sequence variants are characterized by the predetermined nature of the variation, a feature that sets them apart from naturally occurring allelic or interspecies variations of the MIST protein amino acid sequence. The variants typically exhibit the same qualitative biological activity as that of the naturally occurring analogue, although variants can also be selected having modified characteristics. While the site or region for introducing an amino acid sequence variation is predetermined, the mutation per se need not be predetermined. For example, in order to optimize the performance of a mutation at a given site, random mutagenesis may be performed at the target codon or region, and the expressed MIST variants screened for the optimal combination of desired activity. Techniques for making substitution mutations at predetermined sites in DNA having a known sequence are well known, for example, M13 primer mutagenesis and PCR mutagenesis. Screening of the mutants is accomplished using assays of MIST protein activities, for example, for binding domain mutations, competitive binding studies may be carried out.

Amino acid substitutions are typically of single residues; insertions usually are on the order of from one to twenty amino acids, although considerably larger insertions may be tolerated. Deletions range from about one to about 20 residues, although in some cases, deletions may be much larger. For example, preferred deletion variants include the deletion of one or more of the characteristic domains, i.e., the proline-rich region, or the SH2 domain.

Substitutions, deletions, insertions, or any combination thereof, may be used to arrive at a final MIST derivative. Generally, these changes affect only a few amino acids to minimize the alteration of the molecule. However, larger changes may be tolerated in certain circumstances. When small alterations in the characteristics of the MIST protein are desired or warranted, substitutions are generally made in accordance with the following Table 2:

TABLE 2

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Table 2. For example, substitutions may be made which more significantly affect the structure of the polypeptide backbone in the area of the alteration, for example, the alpha-helical, or beta-sheet structure; the charge or hydrophobicity of the molecule at the target site; or the bulk of the side chain. The substitutions which generally are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl, or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) a residue that does not have a side chain, e.g., glycine.

While MIST variants ordinarily exhibit the same qualitative biological activity or function, and elicit the same immune response, as the naturally occurring analogue, the variants are also selected to modify the characteristics of the MIST protein as needed. Alternatively, the variant may be designed such the that biological activity of the MIST protein is altered. For example, any or all of the domains may be altered, i.e., the proline-rich region or the SH2 region. For example, one or more of the tyrosine phosphorylation sites may be altered.

In another embodiment, the present invention encompasses polynucleotides which encode the MIST polypeptides. Accordingly, any nucleic acid sequence which encodes the amino acid sequence of the MIST polypeptide can be used to produce recombinant molecules that express MIST protein. In a particular embodiment, the present invention encompasses the MIST polynucleotide comprising the nucleic acid sequence of SEQ ID NO:1 and as shown in FIGS. 1A-1B. More particularly, the present invention provides the cloned full-length MIST cDNA (i.e., clone #8), and splice variants thereof, (i.e., clone #7 and #12) as deposited at the American Type Culture Collection (ATCC®), 10801 University Boulevard, Manassas, Va. 20110-2209 on Jan. 26, 2001, under ATCC® Accession No. PTA-2981 according to the terms of the Budapest Treaty. ATCC® Deposit No. PTA-2981 contains three the human MIST clones #7, #8 and #12 in the PCMV-SPORT2 vector according to the present invention.

As will be appreciated by the skilled practitioner in the art, the degeneracy of the genetic code results in the production of numerous nucleotide sequences encoding the MIST polypeptide of the present invention. Some of the sequences bear minimal homology to the nucleotide sequences of any known and naturally occurring gene. Accordingly, the present invention contemplates each and every possible variation of nucleotide sequence that could be made by selecting combinations based on possible codon choices. These combinations are made in accordance with the standard triplet genetic code as applied to the nucleotide sequence of naturally occurring MIST, and all such variations are to be considered as being specifically disclosed.

Although nucleotide sequences which encode the MIST polypeptide and its variants are preferably capable of hybridizing to the nucleotide sequence of the naturally occurring MIST polypeptide under appropriately selected conditions of stringency, it may be advantageous to produce nucleotide sequences encoding the MIST polypeptide, or its derivatives, which possess a substantially different codon usage. Codons may be selected to increase the rate at which expression of the peptide/polypeptide occurs in a particular prokaryotic or eukaryotic host in accordance with the frequency with which particular codons are utilized by the host, for example, in plant cells or yeast cells or amphibian cells. Other reasons for substantially altering the nucleotide sequence encoding the MIST polypeptide, and its derivatives, without altering the encoded amino acid sequences include the production of mRNA transcripts having more desirable properties, such as a greater half-life, than transcripts produced from the naturally occurring sequence.

The present invention also encompasses production of DNA sequences, or portions thereof, which encode the MIST polypeptide, and its derivatives, entirely by synthetic chemistry. After production, the synthetic sequence may be inserted into any of the many available expression vectors and cell systems using reagents that are well known and practiced by those in the art. Moreover, synthetic chemistry may be used to introduce mutations into a sequence encoding MIST polypeptide, or any fragment thereof.

Another embodiment of the present invention includes alternatively spliced forms of the human MIST polynucleotide sequence yielding the two MIST splice variants as depicted in FIGS. 6A and 6B and 9A and 9B. Such forms of the MIST protein afforded by this invention provide variant smaller versions of the MIST protein that can be employed, for example, following expression in recombinant systems. Accordingly, the present invention provides cloned and isolated splice variant forms of human MIST, the cDNA of which is deposited at the American Type Culture Collection (ATCC®), 10801 University Boulevard, Manassas, Va. 20110-2209 on Jan. 26, 2001 and under ATCC® Accession No. PTA-2981 according to the terms of the Budapest Treaty. Specifically, ATCC® Deposit No. PTA-2981 contains the human MIST clones #7, #8 and #12 in the PCMV-SPORT2 vector as described in the Examples.

Also encompassed by the present invention are polynucleotide sequences that are capable of hybridizing to the claimed nucleotide sequence of MIST, such as that shown in SEQ ID NO:1, under various conditions of stringency. Hybridization conditions are typically based on the melting temperature (Tm) of the nucleic acid binding complex or probe (See, G. M. Wahl and S. L. Berger, 1987; *Methods Enzymol.,* 152:399-407 and A. R. Kimmel, 1987; *Methods of Enzymol.,* 152:507-511), and may be used at a defined stringency. For example, included in the present invention are sequences capable of hybridizing under moderately stringent conditions to the MIST nucleic acid sequence of SEQ ID NO:1 and other sequences which are degenerate to those which encode the MIST polypeptide (e.g., as a nonlimiting example: prewashing solution of 2×SSC, 0.5% SDS, 1.0 mM EDTA, pH 8.0, and hybridization conditions of 50° C., 5×SSC, overnight).

In another embodiment of the present invention, polynucleotide sequences or fragments (peptides) thereof which encode the MIST polypeptide may be used in recombinant DNA molecules to direct the expression of the MIST polypeptide product, or fragments or functional equivalents thereof, in appropriate host cells. Because of the inherent degeneracy of the genetic code, other DNA sequences, which encode substantially the same or a functionally equivalent amino acid sequence, may be produced and these sequences may be used to express MIST protein.

As will be appreciated by those having skill in the art, it may be advantageous to produce MIST polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequence of the present invention can be engineered using methods generally known in the art in order to alter MIST polypeptide-encoding sequences for a variety of reasons, including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and the like.

In another embodiment of the present invention, natural, modified, or recombinant nucleic acid sequences, or a fragment thereof, encoding MIST polypeptide may be ligated to a heterologous sequence to encode a fusion protein. For example, for screening peptide libraries for inhibitors or modulators of MIST activity or binding, it may be useful to encode a chimeric MIST protein that can be recognized by a commercially available antibody. A fusion protein may also be engineered to contain a cleavage site located between the MIST protein-encoding sequence and the heterologous protein sequence, so that the MIST protein may be cleaved and purified away from the heterologous moiety.

In another embodiment, sequences encoding the MIST polypeptide may be synthesized in whole, or in part, using chemical methods well known in the art (See, for example, M. H. Caruthers et al., 1980, *Nucl. Acids Res. Symp. Ser.,* 215-223 and T. Horn, T et al., 1980, *Nucl. Acids Res. Symp. Ser.,* 225-232). Alternatively, the protein itself may be produced using chemical methods to synthesize the amino acid sequence of the MIST polypeptide, or a fragment or portion thereof. For example, peptide synthesis can be performed using various solid-phase techniques (J. Y. Roberge et al., 1995, *Science,* 269:202-204) and automated synthesis may be achieved, for example, using the ABI 431A Peptide Synthesizer (PE Biosystems).

The newly synthesized peptide can be substantially purified by preparative high performance liquid chromatography (e.g., T. Creighton, 1983, *Proteins, Structures and Molecular Principles,* WH Freeman and Co., New York, N.Y.), by reversed-phase high performance liquid chromatography, or other purification methods as are known in the art. The composition of the synthetic peptides may be confirmed by amino acid analysis or sequencing (e.g., the Edman degradation procedure; Creighton, supra). In addition, the amino acid sequence of the MIST polypeptide or any portion thereof, may be altered during direct synthesis and/or combined using chemical methods with sequences from other proteins, or any part thereof, to produce a variant polypeptide.

Polypeptide Lacking a Start Methionine

In a preferred embodiment, the present invention encompasses a polynucleotide lacking the initiating start codon, in addition to the resulting encoded polypeptide of MIST. Specifically, the present invention encompasses the polynucleotide corresponding to nucleotides 323 through 1648 of SEQ ID NO:1, and the polypeptide corresponding to amino acids 2 through 443 of SEQ ID NO:2. Also encompassed by this invention are recombinant vectors comprising the polynucleotide sequence encoding MIST, and host cells comprising the vector.

Also preferably, the present invention encompasses a polynucleotide lacking the initiating start codon, in addition to the resulting encoded polypeptide of the MIST splice variant clone #7. Specifically, the present invention encompasses the polynucleotide corresponding to nucleotides 264 through 2139 of SEQ ID NO:3, and the polypeptide corresponding to amino acids 2 through 428 of SEQ ID NO:4.

The present invention further embraces recombinant vectors comprising the sequence (i.e., SEQ ID NO:3) encoding the clone #7 MIST variant and host cells comprising the vector.

In addition, the present invention preferably encompasses a polynucleotide lacking the initiating start codon, in addition to, the resulting encoded polypeptide of the MIST splice variant clone #12. Specifically, the present invention encompasses the polynucleotide corresponding to nucleotides 694 through 2139 of SEQ ID NO:5, and the polypeptide corresponding to amino acids 2 through 353 of SEQ ID NO:6. The present invention further embraces recombinant vectors comprising the sequence encoding the MIST variant of clone #12 and host cells comprising the vector.

Such polynucleotides and polypeptides (i.e., those lacking a start codon and start methionine, respectively) are useful in the production of fusion proteins, as described herein, or as otherwise known in the art.

Expression of Human MIST Protein

To express a biologically active/functional MIST polypeptide or peptide, the nucleotide sequences encoding the MIST polypeptide, or functional equivalents, may be inserted into an appropriate expression vector, i.e., a vector which contains the necessary elements for the transcription and translation of the inserted coding sequence. Methods which are well known to those skilled in the art may be used to construct expression vectors containing sequences encoding the MIST polypeptide and appropriate transcriptional and translational control elements. These methods include in vitro recombinant DNA techniques, synthetic techniques, and in vivo genetic recombination. Such techniques are described in J. Sambrook et al., 1989, *Molecular Cloning, A Laboratory Manual*, Cold Spring Harbor Press, Plainview, N.Y. and in F. M. Ausubel et al., 1989, *Current Protocols in Molecular Biology*, John Wiley & Sons, New York, N.Y.

A variety of expression vector/host systems may be utilized to contain and express sequences encoding the MIST polypeptide. Such expression vector/host systems include, but are not limited to, microorganisms such as bacteria transformed with recombinant bacteriophage, plasmid, or cosmid DNA expression vectors; yeast or fungi transformed with yeast or fungal expression vectors; insect cell systems infected with virus expression vectors (e.g., baculovirus); plant cell systems transformed with virus expression vectors (e.g., cauliflower mosaic virus (CaMV) and tobacco mosaic virus (TMV)), or with bacterial expression vectors (e.g., Ti or pBR322 plasmids); or animal cell systems. The host cell employed is not limiting to the present invention.

"Control elements" or "regulatory sequences" are those non-translated regions of the vector, e.g., enhancers, promoters, 5' and 3' untranslated regions, which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene, La Jolla, Calif.) or PSPORT1 plasmid (Life Technologies, MD), and the like, may be used. The baculovirus polyhedrin promoter may be used in insect cells. Promoters or enhancers derived from the genomes of plant cells (e.g., heat shock, RUBISCO; and storage protein genes), or from plant viruses (e.g., viral promoters or leader sequences), may be cloned into the vector. In mammalian cell systems, promoters from mammalian genes or from mammalian viruses are preferred. If it is necessary to generate a cell line that contains multiple copies of the sequence encoding MIST, vectors based on SV40 or EBV may be used with an appropriate selectable marker.

In bacterial systems, a number of expression vectors may be selected, depending upon the use intended for the expressed MIST product. For example, when large quantities of expressed protein are needed for the induction of antibodies, vectors which direct high level expression of fusion proteins that are readily purified may be used. Such vectors include, but are not limited to, the multifunctional *E. coli* cloning and expression vectors such as BLUESCRIPT® (Stratagene), in which the sequence encoding the MIST polypeptide, or a peptide thereof, may be ligated into the vector in-frame with sequences for the amino-terminal Met and the subsequent 7 residues of β-galactosidase, so that a hybrid protein is produced; pIN vectors (See, G. Van Heeke and S. M. Schuster, 1989, *J. Biol. Chem.*, 264:5503-5509); and the like. pGEX vectors (Promega, Madison, Wis.) may also be used to express foreign polypeptides, as fusion proteins with glutathione S-transferase (GST). As another type of fusion construct, immunoglobulin (Ig) fusions can be used, such as the MIST-Ig fusion proteins shown in FIG. 11. Methods for producing such proteins are practiced in the art. (See, e.g., Gilliland et al., 1992, *J. Biol. Chem.*, 267:13610-13616).

In addition, MIST fusion proteins expressing a His tag are preferred, in which SH2 domains from human MIST cDNA are cloned into an expression vector linked to a poly-His tag (His) as shown in FIG. 11 and as described in Example 9.

In general, fusion proteins are soluble and can be easily purified from lysed cells. For GST-fusion proteins purification is performed by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. (For reviews, see F. M. Ausubel et al., supra, and Grant et al., 1987, *Methods Enzymol.*, 153:516-544).

Should plant expression vectors be desired and used, the expression of sequences encoding the MIST polypeptide may be driven by any of a number of promoters. For example, viral promoters such as the 35S and 19S promoters of CaMV may be used alone or in combination with the omega leader sequence from TMV (N. Takamatsu, 1987, *EMBO J.*, 6:307-311). Alternatively, plant promoters such as the small subunit of RUBISCO, or heat shock promoters, may be used (G. Coruzzi et al., 1984, *EMBO J.*, 3:1671-1680; R. Broglie et al., 1984, *Science*, 224:838-843; and J. Winter et al., 1991, *Results Probl. Cell Differ.* 17:85-105). These constructs can be introduced into plant cells by direct DNA transformation or pathogen-mediated transfection. Such techniques are described in a number of generally available reviews (See, for example, S. Hobbs or L. E. Murry, In: McGraw Hill *Yearbook of Science and Technology* (1992) McGraw Hill, New York, N.Y.; pp. 191-196).

An insect system may also be used to express the MIST polypeptide For example, in one such system, *Autographa californica* nuclear polyhedrosis virus (AcNPV) is used as a vector to express foreign genes in *Spodoptera frugiperda* cells or in *Trichoplusia larvae*. The sequences encoding the MIST polypeptide may be cloned into a non-essential region of the virus such as the polyhedrin gene and placed under control of the polyhedrin promoter. Successful insertion of the MIST polypeptide will render the polyhedrin gene inactive and produce recombinant virus lacking coat protein. The recombinant viruses may then be used to infect, for example, *S. frugiperda* cells or *Trichoplusia larvae* in which the MIST polypeptide product may be expressed (E. K. Engelhard et al., 1994, *Proc. Nat. Acad. Sci.,* 91:3224-3227).

In mammalian host cells, a number of viral-based expression systems may be utilized. In cases where an adenovirus is used as an expression vector, sequences encoding the MIST polypeptide may be ligated into an adenovirus transcription/translation complex containing the late promoter and tripartite leader sequence. Insertion in a non-essential E1 or E3 region of the viral genome may be used to obtain a viable virus which is capable of expressing the MIST polypeptide in infected host cells (J. Logan and T. Shenk, 1984, *Proc. Natl. Acad. Sci.,* 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding the MIST polypeptide. Such signals include the ATG initiation codon and adjacent sequences. In cases where sequences encoding the MIST polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals, including the ATG initiation codon, should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system that is used, such as those described in the literature (D. Scharf et al., 1994, *Results Probl. Cell Differ.,* 20:125-162).

Moreover, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells having specific cellular machinery and characteristic mechanisms for such post-translational activities (e.g., COS, CHO, HeLa, MDCK, HEK293, and W138) are available from the American Type Culture Collection (ATCC®), American Type Culture Collection (ATCC®), 10801 University Boulevard, Manassas, Va. 20110-2209, and may be chosen to ensure the correct modification and processing of the foreign protein.

For long-term, high-yield production of recombinant proteins, stable expression is preferred. For example, cell lines which stably express the MIST protein may be transformed using expression vectors which may contain viral origins of replication and/or endogenous expression elements and a selectable marker gene on the same, or on a separate, vector. Following the introduction of the vector, cells may be allowed to grow for 1-2 days in an enriched cell culture medium before they are switched to selective medium. The purpose of the selectable marker is to confer resistance to selection, and its presence allows the growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the Herpes Simplex Virus thymidine kinase (HSV TK), (M. Wigler et al., 1977, *Cell,* 11:223-32) and adenine phosphoribosyltransferase (I. Lowy et al., 1980, *Cell,* 22:817-23) genes which can be employed in $tk^-$ or $aprt^-$ cells, respectively. Also, anti-metabolite, antibiotic or herbicide resistance can be used as the basis for selection; for example, dhfr, which confers resistance to methotrexate (M. Wigler et al., 1980, *Proc. Natl. Acad. Sci.,* 77:3567-70); npt, which confers resistance to the aminoglycosides neomycin and G-418 (F. Colbere-Garapin et al., 1981, *J. Mol. Biol.,* 150:1-14); and als or pat, which confer resistance to chlorsulfuron and phosphinothricin acetyltransferase, respectively (Murry, supra). Additional selectable genes have been described, for example, trpB, which allows cells to utilize indole in place of tryptophan, or hisD, which allows cells to utilize histinol in place of histidine (S. C. Hartman and R. C. Mulligan, 1988, *Proc. Natl. Acad. Sci.,* 85:8047-51). Recently, the use of visible markers has gained popularity with such markers as the anthocyanins, β-glucuronidase and its substrate GUS, and luciferase and its substrate luciferin, which are widely used not only to identify transformants, but also to quantify the amount of transient or stable protein expression that is attributable to a specific vector system (C. A. Rhodes et al., 1995, *Methods Mol. Biol.,* 55:121-131).

Although the presence/absence of marker gene expression suggests that the gene of interest is also present, the presence and expression of the desired gene of interest may need to be confirmed. For example, if the MIST nucleic acid sequence polypeptide is inserted within a marker gene sequence, recombinant cells containing sequences encoding the MIST polypeptide can be identified by the absence of marker gene function. Alternatively, a marker gene can be placed in tandem with a sequence encoding the MIST polypeptide under the control of a single promoter. Expression of the marker gene in response to induction or selection usually indicates co-expression of the tandem gene.

Alternatively, host cells which contain the nucleic acid sequence encoding the MIST polypeptide and which express the MIST polypeptide product may be identified by a variety of procedures known to those having skill in the art. These procedures include, but are not limited to, DNA-DNA or DNA-RNA hybridizations and protein bioassay or immunoassay techniques, including membrane, solution, or chip based technologies, for the detection and/or quantification of nucleic acid or protein.

Preferably, the MIST polypeptide is substantially purified after expression. MIST proteins can be isolated or purified in a variety of ways known to and practiced by those having skill in the art, depending on what other components may be present in the sample. Standard purification methods include electrophoretic, molecular, immunological and chromatographic techniques, including, but not limited to, ion exchange, hydrophobic affinity and reverse phase HPLC chromatography, and chromatofocusing. For example, the MIST protein can be purified using a standard anti-MIST antibody column. Ultrafiltration and diafiltration techniques, in conjunction with protein concentration, are also useful. For general guidance in suitable purification techniques, see R. Scopes, 1982, *Protein Purification*, Springer-Verlag, NY. As will be understood by the skilled practitioner, the degree of purification necessary will vary depending on the intended use of the MIST protein; in some instances, no purification will be necessary.

In addition to recombinant production, fragments of the MIST polypeptide may be produced by direct peptide synthesis using solid-phase techniques (J. Merrifield, 1963, *J. Am. Chem. Soc.*, 85:2149-2154). Protein synthesis may be performed using manual techniques or by automation. Automated synthesis may be achieved, for example, using ABI 431A Peptide Synthesizer (PE Biosystems). Various fragments of the MIST polypeptide can be chemically synthesized separately and then combined using chemical methods to produce the full length molecule.

Detection of Human MIST Polynucleotide

The presence of polynucleotide sequences encoding the MIST polypeptide can be detected by DNA-DNA or DNA-RNA hybridization, or by amplification using probes or portions or fragments of polynucleotides encoding the MIST polypeptide. Nucleic acid amplification based assays involve the use of oligonucleotides or oligomers, based on the sequences encoding the MIST polypeptide, to detect transformants containing DNA or RNA encoding the MIST polypeptide.

A wide variety of labels and conjugation techniques are known and employed by those skilled in the art and may be used in various nucleic acid and amino acid assays. Means for producing labeled hybridization or PCR probes for detecting sequences related to polynucleotides encoding the MIST polypeptide include oligo-labeling, nick translation, end-labeling, or PCR amplification using a labeled nucleotide. Alternatively, the sequences encoding the MIST polypeptide, or any portions or fragments thereof, may be cloned into a vector for the production of an mRNA probe. Such vectors are known in the art, are commercially available, and may be used to synthesize RNA probes in vitro by addition of an appropriate RNA polymerase, such as T7, T3, or SP(6) and labeled nucleotides. These procedures may be conducted using a variety of commercially available kits (e.g., Amersham Pharmacia Biotech, Promega and U.S. Biochemical Corp.). Suitable reporter molecules or labels which may be used include radionuclides, enzymes, fluorescent, chemiluminescent, or chromogenic agents, as well as substrates, cofactors, inhibitors, magnetic particles, and the like.

In another of its aspects, this invention relates to a diagnostic kit for detecting MIST polynucleotide or polypeptide as it relates to a disease or susceptibility to a disease, particularly autoimmune diseases which may be caused by hyperactivated B cells, as well as diseases which may be caused by hyperactivated T cells (e.g., rheumatoid arthritis; asthma; psoriasis; multiple sclerosis; rejection of organ or tissue transplants; chronic obstructive pulmonary disease; inflammatory bowel diseases, including Crohn's Disease and ulcerative colitis; acute respiratory distress syndrome; and systemic lupus erythematosis), or disorders associated with other types of hematopoietic cells, such as allergies involving mast cells. Such a kit comprises one or more of the following: (a) a MIST polynucleotide, preferably the nucleotide sequence of SEQ ID NO:1, or a fragment thereof; or (b) a nucleotide sequence complementary to that of (a); or (c) a MIST polypeptide, preferably the polypeptide of SEQ ID NO: 2, or a fragment thereof; or (d) an antibody to a MIST polypeptide, preferably to the polypeptide of SEQ ID NO: 2, or an antibody bindable portion thereof. It will be appreciated that in any such kit, (a), (b), (c) or (d) may comprise a substantial component and that instructions for use can be included.

Human MIST Polypeptides—Production, Detection, Isolation

Host cells transformed with nucleotide sequences encoding the MIST protein, or fragments thereof, may be cultured under conditions suitable for the expression and recovery of the protein from cell culture. The protein produced by a recombinant cell may be secreted or contained intracellularly depending on the sequence and/or the vector used. As will be understood by those having skill in the art, expression vectors containing polynucleotides which encode the MIST protein may be designed to contain signal sequences which direct secretion of the MIST protein through a prokaryotic or eukaryotic cell membrane.

Other constructions may be used to join nucleic acid sequences encoding the MIST protein to nucleotide sequence encoding a polypeptide domain which will facilitate purification of soluble proteins. Such purification facilitating domains include, but are not limited to, metal chelating peptides such as histidine-tryptophan modules that allow purification on immobilized metals; protein A domains that allow purification on immobilized immunoglobulin; and the domain utilized in the FLAGS® extension/affinity purification system (Immunex Corp., Seattle, Wash.). The inclusion of cleavable linker sequences such as those specific for Factor XA or enterokinase (Invitrogen, San Diego, Calif.) between the purification domain and the MIST protein may be used to facilitate purification.

One such expression vector provides for expression of a fusion protein containing MIST-encoding sequence and a nucleic acid encoding 6 histidine residues preceding a thioredoxin or an enterokinase cleavage site. The histidine residues facilitate purification on IMAC (immobilized metal ion affinity chromatography) as described by J. Porath et al., 1992, *Prot. Exp. Purif.*, 3:263-281, while the enterokinase cleavage site provides a means for purifying from the fusion protein. For a discussion of suitable vectors for fusion protein production, see D. J. Kroll et al., 1993; *DNA Cell Biol.*, 12:441-453.

Human artificial chromosomes (HACs) may be used to deliver larger fragments of DNA than can be contained and expressed in a plasmid vector. HACs are linear microchromosomes which may contain DNA sequences of 10K to 10M in size, and contain all of the elements that are required for stable mitotic chromosome segregation and maintenance (See, J. J. Harrington et al., 1997, *Nature Genet.*, 15:345-355). HACs of 6 to 10M are constructed and delivered via conventional delivery methods (e.g., liposomes, polycationic amino polymers, or vesicles) for therapeutic purposes.

A variety of protocols for detecting and measuring the expression of the MIST polypeptide using either polyclonal or monoclonal antibodies specific for the protein are known and practiced in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive with two non-interfering epitopes on the MIST polypeptide is preferred, but a competitive binding assay may also be employed. These and other assays are described in the art as represented by the publication of R. Hampton et al., 1990; *Serological Methods, a Laboratory Manual*, APS Press, St Paul, Minn. and D. E. Maddox et al., 1983; *J. Exp. Med.*, 158:1211-1216).

Anti-Human Mist Antibodies and Uses Thereof

Antagonists or inhibitors of the MIST polypeptide of the present invention may be produced using methods which are generally known in the art. In particular, purified MIST protein, or fragments thereof, can be used to produce antibodies, or to screen libraries of pharmaceutical agents or other compounds, particularly, small molecules, to identify those which specifically bind MIST. (e.g., libraries commercially available from Sigma or Aldrich).

Antibodies specific for the MIST polypeptide, or immunogenic peptide fragments thereof, can be generated using methods that have long been known and conventionally practiced in the art. Such antibodies may include, but are not limited to, polyclonal, monoclonal, chimeric, single chain, Fab fragments, and fragments produced by an Fab expression library. Neutralizing antibodies, (i.e., those which inhibit dimer formation) are especially preferred for therapeutic use. For the production of antibodies, various hosts including goats, rabbits, sheep, rats, mice, humans, and others, can be immunized by injection with MIST polypeptide, or any peptide fragment or oligopeptide thereof, which has immunogenic properties. Depending on the host species, various adjuvants may be used to increase the immunological response. Nonlimiting examples of suitable adjuvants include Freund's (incomplete), mineral gels such as aluminum hydroxide or silica, and surface active substances such as lysolecithin, pluronic polyols, polyanions, peptides, oil emulsions, KLH, and dinitrophenol. Adjuvants typically used in humans include BCG (bacilli Calmette Guérin) and *Corynebacterium parvum*.

Preferably, the peptides, fragments, or oligopeptides used to induce antibodies to MIST polypeptide (i.e., immunogens) have an amino acid sequence having at least five amino acids, and more preferably, at least 7-10 amino acids. It is also preferable that the immunogens are identical to a portion of the amino acid sequence of the natural protein; they may also contain the entire amino acid sequence of a small, naturally occurring molecule. The peptides, fragments or oligopeptides may comprise a single epitope or antigenic determinant or multiple epitopes. Short stretches of MIST amino acids may be fused with those of another protein, such as KLH, and antibodies are produced against the chimeric molecule.

Monoclonal antibodies to MIST polypeptide, or immunogenic fragments thereof, may be prepared using any technique which provides for the production of antibody molecules by continuous cell lines in culture. These include, but are not limited to, the hybridoma technique, the human B-cell hybridoma technique, and the EBV-hybridoma technique (G. Kohler et al., 1975, *Nature,* 256:495-497; D. Kozbor et al., 1985, *J. Immunol. Methods,* 81:3142; R. J. Cote et al., 1983, *Proc. Natl. Acad. Sci. USA,* 80:2026-2030; and S. P. Cole et al., 1984, *Mol. Cell Biol.,* 62:109-120). The production of monoclonal antibodies is well known and routinely used in the art.

According to the present invention, antibodies can be generated from various regions of the MIST polypeptide. In particular, the His-MIST-PR expression product, which comprises amino acids 160-320 of the MIST sequence, (FIG. 11), has been used to produce monoclonal antibodies using well-known techniques as described herein (See Example 11). Three monoclonal antibodies have been found to immunoreact with native human MIST protein in human mast cell lysates. In addition, the other human MIST constructs shown and described in FIG. 11, which contain discrete domains of the MIST protein (e.g., the proline-rich domain, or a portion thereof, the residues of which are depicted in FIGS. 3A-3B and the SH2 domain, or a portion thereof, the residues of which are also depicted in FIGS. 3A-3B), are also suitable for use as immunogens to produce antibodies to human MIST.

In addition, techniques developed for the production of "chimeric antibodies," the splicing of mouse antibody genes to human antibody genes to obtain a molecule with appropriate antigen specificity and biological activity can be used (S. L. Morrison et al., 1984, *Proc. Natl. Acad. Sci. USA,* 81:6851-6855; M. S, Neuberger et al., 1984, *Nature,* 312:604-608; and S. Takeda et al., 1985, *Nature,* 314:452-454). Alternatively, techniques described for the production of single chain antibodies may be adapted, using methods known in the art, to produce MIST polypeptide-specific single chain antibodies. Antibodies with related specificity, but of distinct idiotypic composition, may be generated by chain shuffling from random combinatorial immunoglobulin libraries (D. R. Burton, 1991, *Proc. Natl. Acad. Sci. USA,* 88:11120-3). Antibodies may also be produced by inducing in vivo production in the lymphocyte population or by screening recombinant immunoglobulin libraries or panels of highly specific binding reagents as disclosed in the literature (R. Orlandi et al., 1989, *Proc. Natl. Acad. Sci. USA,* 86:3833-3837 and G. Winter et al., 1991, *Nature,* 349:293-299).

Antibody fragments which contain specific binding sites for the MIST polypeptide may also be generated. For example, such fragments include, but are not limited to, F(ab')$_2$ fragments which can be produced by pepsin digestion of the antibody molecule and Fab fragments which can be generated by reducing the disulfide bridges of the F(ab')$_2$ fragments. Alternatively, Fab expression libraries may be constructed to allow rapid and easy identification of monoclonal Fab fragments with the desired specificity (W. D. Huse et al., 1989, *Science,* 254.1275-1281).

Various immunoassays can be used for screening to identify antibodies having the desired specificity. Numerous protocols for competitive binding or immunoradiometric assays using either polyclonal or monoclonal antibodies with established specificities are well known in the art. Such immunoassays typically involve measuring the formation of complexes between the MIST polypeptide and its specific antibody. A two-site, monoclonal-based immunoassay utilizing monoclonal antibodies reactive with two non-interfering MIST polypeptide epitopes is preferred, but a competitive binding assay may also be employed (Maddox, supra).

Therapeutics/Treatments

In an embodiment of the present invention, the polynucleotide encoding the MIST polypeptide, or any fragment or complement thereof, may be used for therapeutic purposes. In one aspect, antisense to the polynucleotide encoding the MIST polypeptide may be used in situations in which it would be desirable to block the transcription of the mRNA. In particular, cells may be transformed with sequences complementary to polynucleotides encoding the MIST polypeptide. Thus, complementary molecules may be used to modulate human MIST polynucleotide and polypeptide activity, or to achieve regulation of gene function. Such technology is now well known in the art, and sense or antisense oligomers or oligonucleotides, or larger fragments, can be designed from various locations along the coding or control regions of polynucleotide sequences encoding the MIST polypeptide.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express nucleic acid sequence that is complementary to the nucleic acid sequence encoding the MIST polypeptide. These techniques are described both in J. Sambrook et al., supra and in F. M. Ausubel et al., supra.

The gene encoding the MIST polypeptide can be turned off by transforming a cell or tissue with an expression vector that expresses high levels of a MIST polypeptide-encoding polynucleotide, or a fragment thereof. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and even longer if appropriate replication elements are designed to be part of the vector system.

Modifications of gene expression can be obtained by designing antisense molecules or complementary nucleic acid sequences (DNA, RNA, or PNA), to the control, 5', or regulatory regions of the gene encoding the MIST polypeptide, (e.g., signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described (See, for example, J. E. Gee et al., 1994, In: B. E. Huber and B. I. Carr, *Molecular and Immunologic Approaches*, Futura Publishing Co., Mt. Kisco, N.Y.). The antisense molecule or complementary sequence may also be designed to block translation of mRNA by preventing the transcript from binding to ribosomes.

Ribozymes, i.e., enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Suitable examples include engineered hammerhead motif ribozyme molecules that can specifically and efficiently catalyze endonucleolytic cleavage of sequences encoding the MIST polypeptide.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes according to the invention may be prepared by any method known in the art for the synthesis of nucleic acid molecules. Such methods include techniques for chemically synthesizing oligonucleotides, for example, solid phase phosphoramidite chemical synthesis. Alternatively, RNA molecules may be generated by in vitro and in vivo transcription of DNA sequences encoding human MIST. Such DNA sequences may be incorporated into a wide variety of vectors with suitable RNA polymerase promoters such as T7 or SP. Alternatively, the cDNA constructs that constitutively or inducibly synthesize complementary MIST RNA can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl, rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and are equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Based on reports that both SLP-76 and BLNK serve as docking molecules for numerous proteins involved in signal transduction (P. S. Myung et al., 2000, supra), the MIST protein provided by the present invention could also interact with signaling molecules through its SH2 domain, proline-rich motifs or its phosphotyrosine residues. To test whether different domains from MIST could associate with other proteins involved in cell activation, several poly-histidine (His) tagged MIST fusion proteins were designed and created, including: MIST full length (His-MIST-fl, residues 1-443), the proline-rich domain (His-MIST-PR, residues 160-320), the SH2 domain (His-MIST-SH2, residues 320-443), and an Ig fusion protein including the MIST SH2 domain and the heavy chain of a human IgG2a molecule (FIG. 11). (See also Example 3).

The results of the binding analyses using the MIST fusion constructs of FIG. 11 demonstrated that the adapter protein Grb2 was associated with MIST, as well as other important intracellular signaling proteins, namely, Vav, a ras nucleotide exchange activator protein; LAT (Linker for Activation of T-cells, W. Zhang et al., 1998, *Cell*, 92:83) and c-Cbl, an 110-kDa protein that has been reported to have ubiquitin ligase activity and to be involved in trafficking molecules from the plasma membrane to other parts of the cell. (M. L. Lupher, Jr. et al., 1999, *Immunol. Today*, 20:375-382).

In another embodiment of the present invention, an expression vector containing the complement of the polynucleotide encoding the MIST polypeptide or an antisense oligonucleotide, may be administered to an individual to treat or prevent an immune disorder or neoplastic disease of T- or B-lymphocytes, e.g., tumors, thymomas, lymphomas, and leukemias, or an autoimmune diseases associated with activated T- or B-lymphocytes. A variety of specialized oligonucleotide delivery techniques may be employed, for example, encapsulation in unilamellar liposomes and reconstituted Sendai virus envelopes for RNA and DNA delivery (Arad et al., 1986, *Biochem. Biophys. Acta.*, 859:88-94).

In another embodiment, the proteins, antagonists, antibodies, agonists, complementary sequences, or vectors of the present invention can be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Any of the therapeutic methods described above may be applied to any individual in need of such therapy, including, for example, mammals such as dogs, cats, cows, horses, rabbits, monkeys, and most preferably, humans.

Screening Methods

The MIST protein and nucleic acid can be used in screening assays of candidate bioactive agents that modulate MIST bioactivity, for potential use to treat T- and B-cell disorders, such as tumors, lymphomas, and leukemias, or to treat inflammation disorders, such as those involving mast cells and eosinophils, especially hyperactive cells. In addition, MIST protein and encoding nucleic acid can be used as effectors in methods to affect T-cell activation. By "modulate" herein is meant that the bioactivity of MIST is altered, i.e., either increased or decreased. In a preferred embodiment, MIST bioactivity is inhibited. MIST is a member of the class of adapter proteins involved in T-cell activation and T-cell responses; thus, it can play a role in T- (or B-) cell function. Accordingly, MIST can be used as a target to screen for inhibitors of its function or expression.

Inhibitors of human MIST may be identified by screening compounds to ascertain their effect on MIST activity. As described herein, in some embodiments of the present invention, compounds are screened to identify inhibitors by contacting human MIST with a molecule with which it binds or associates, e.g., Grb2, in the presence or absence of a test compound. Under conditions of the assay, the inhibitors will prevent or reduce binding of human MIST to Grb2, for example. Antibodies or synthetic peptides which inhibit MIST/Grb2 binding are useful as inhibitors and, therefore as positive controls in the assay.

In a similar fashion, activators of human MIST may be identified by screening compounds to ascertain their effect on MIST/Grb2 binding, for example. In some embodiments of the present invention, compounds are screened to identify activators by contacting human MIST with Grb2 in the presence or absence of a test compound. Under conditions of the assay, the activators will enhance, accelerate or increase binding of human MIST to Grb2. Antibodies which inhibit MIST/Grb2 binding are useful as negative controls in such assays.

In another embodiment, an assay is provided to identify compounds that inhibit the phosphorylation of MIST by tyrosine kinases such as, for example but not limited to, certain cellular receptors. In one aspect, MIST is bound to solid substrate and the reaction buffer contains $^{32}$P-gamma-ATP. Tyrosine kinase is added in the presence or absence of a test compound. Test compounds are identified that result in a decrease in the amount of $^{32}$P label that is incorporated into MIST, compared with the level of phosphorylation observed in their absence. Kits are provided which comprise a container with MIST fixed to a solid phase, a container with the reaction buffer, optionally containing $^{32}$P-gamma-ATP, and a container with tyrosine kinase. Kits may optionally have positive and/or negative controls. Such kits typically also have instructions for performing such assays.

In another embodiment of the present invention, MIST proteins and nucleic acids are used in screening assays to identify and detect candidate bioactive agents that modulate MIST bioactivity, for potential use to treat autoimmune diseases which may be caused by hyperactivated B cells, as well as to treat diseases which may be caused by hyperactivated T cells (e.g., rheumatoid arthritis; asthma; psoriasis; multiple sclerosis; rejection of organ or tissue transplants; chronic obstructive pulmonary disease; inflammatory bowel diseases, including Crohn's Disease and ulcerative colitis; acute respiratory distress syndrome; and systemic lupus erythematosis), or disorders associated with other types of hematopoietic cells, such as allergies involving mast cells.

In a related embodiment, the methods comprise screening for a bioactive agent capable of inhibiting the bioactivity of a MIST protein. By "bioactivity" herein is meant the binding of the MIST to any of its targets, including Grb2, or VAV, or LAT or c-Cbl. Thus, bioactive agents that prevent MIST binding, i.e., interrupt or block or inhibit the interaction of MIST and its target molecule, may be found. The method comprises combining the MIST protein and a candidate bioactive agent, and determining the binding of the candidate agent to MIST protein.

Generally, in performing such methods, a MIST polypeptide is non-diffusably bound to an insoluble support having isolated sample receiving areas (e.g. a microtiter plate, an array, etc.). The criteria for suitable insoluble supports are that they can be made of any composition to which polypeptides can be bound, they are readily separated from soluble material, and they are otherwise compatible with the overall method of screening. The surface of such supports may be solid or porous and of any convenient size or shape. Examples of suitable insoluble supports include microtiter plates, arrays, membranes and beads. These are typically made of glass, plastic (e.g., polystyrene), polysaccharides, nylon or nitrocellulose. Microtiter plates and arrays are especially convenient, because a large number of assays can be carried out simultaneously, using small amounts of reagents and samples. The particular manner of binding the polypeptide is not crucial, so long as it is compatible with the reagents and overall methods of the invention, maintains the activity of the peptide and is nondiffusable. Preferred methods of binding include the use of antibodies (which should not hinder the binding of MIST to its associated proteins), direct binding to "sticky" or ionic supports, chemical crosslinking, etc. Following binding of the polypeptide, excess unbound material is removed by washing. The sample receiving areas may then be blocked as needed through incubation with bovine serum albumin (BSA), casein or other innocuous/nonreactive protein.

A candidate bioactive agent is added to the assay. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The term "agent" as used herein describes any molecule, e.g., protein, oligopeptide, small organic molecule, polysaccharide, polynucleotide, etc., having the capability of directly or indirectly altering the bioactivity of MIST proteins. Generally a plurality of assay mixtures are run in parallel with different agent concentrations to obtain a differential response to the various concentrations. Typically, one of these concentrations serves as a negative control, i.e., at zero concentration, or below the level of detection.

Candidate agents encompass numerous chemical classes, though typically they are organic molecules, preferably small organic compounds having a molecular weight of more than 100 and less than about 10,000 daltons, preferably less than about 2000 to 5000 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. In addition, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

The determination of the binding of the candidate bioactive agent to the MIST polypeptide may be accomplished in a number of ways practiced in the art. In one aspect, the candidate bioactive agent is labeled, and binding is determined directly. Where the screening assay is a binding assay, one or more of the molecules may be joined to a label, where the label can directly or indirectly provide a detectable signal. Various labels include radioisotopes, fluorescent and chemiluminescent compounds, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule which allows detection, in accordance with known procedures. In some embodiments, only one of the components is labeled. Alternatively, more than one component may be labeled with different labels; for example, the MIST polypeptide may be labeled with one fluorophor and the candidate agent labeled with another In one embodiment, the candidate bioactive agent is labeled. Labeled candidate bioactive agents are incubated with the MIST polypeptide for a time sufficient to allow binding, if present. Incubations may be performed at any temperature which facilitates optimal activity, typically between 4° C. and 40° C. Incubation periods are selected for optimum activity, but may also be optimized to facilitate rapid high throughput screening. Typically between 0.1 and 1 hour is sufficient. Excess reagent is generally removed or washed away. The presence or absence of the labeled component is detected to determine and indicate binding.

In a preferred embodiment, the screening method comprises combining a MIST protein, a candidate bioactive agent, and either Grb2 or another of the signaling proteins that associate with MIST (e.g., Vav, LAT, c-Cbl), and determining the binding of MIST to either Grb2 or other signaling protein to determine the effect of the candidate bioactive agent on the MIST-signaling protein interaction.

In a differential screening method to identity bioactive agents that are capable of modulating the bioactivity of the MIST protein, MIST polypeptide is combined with either Grb2 or another signaling molecule which interacts with MIST in a first sample. A second sample comprises a candidate bioactive agent, MIST polypeptide and either Grb2 or other MIST interacting signaling molecule. The binding of MIST to either Grb2 or other signaling molecule is determined for both samples, and a change, or difference in binding, between the two samples indicates the presence of an agent capable of modulating the bioactivity of MIST. Alternatively, a differential screening method is utilized to identify drug candidates that bind to the native MIST, but cannot bind to modified MIST proteins, or variant MIST proteins, for example, those that have modifications which eliminate or decrease bioactivity of a MIST protein.

Preferably in such methods, all control and test samples are performed in at least triplicate to obtain statistically significant results. Incubation of all samples is for a time sufficient for the binding of the MIST proteins and the Grb2 and/or other signaling protein. Following incubation, all samples are washed free of non-specifically bound material and the amount of bound, labeled material determined. For example, where a radiolabel is employed as a label, the samples may be counted in a scintillation counter to determine the amount of labeled compound.

A variety of other reagents may be included in the screening assay. Such reagents include, but are not limited to, salts, neutral proteins, e.g. albumin, detergents, etc., which may be used to facilitate optimal protein-protein binding and/or reduce non-specific or background interactions. In addition, reagents that otherwise improve the efficiency of the assay, such as protease inhibitors, nuclease inhibitors, anti-microbial agents, etc. may be used. Further, the mixture of components in the method may be added in any order that provides for the requisite binding.

Kits are included as an embodiment of the present invention which comprise containers with reagents necessary to screen test compounds. Such kits include human MIST and instructions for performing the assay. For example, kits may include means to detect and/or measure human MIST binding using antibodies that bind to human MIST/Grb2 complex, but not to uncomplexed proteins, or antibodies that bind to uncomplexed proteins but not the human MIST/Grb2 complex. Optionally anti-human MIST antibodies are provided as a control.

Pharmaceutical Compositions

A further embodiment of the present invention embraces the administration of a pharmaceutical composition, in conjunction with a pharmaceutically acceptable carrier, diluent, or excipient, for any of the above-described therapeutic uses and effects. Such pharmaceutical compositions may comprise MIST nucleic acid, polypeptide, or peptides, antibodies to MIST polypeptide, or fragments thereof, mimetics, agonists (e.g., activators), antagonists (e.g., inhibitors) of the MIST polypeptide or polynucleotide. The compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents, drugs, hormones, or biological response modifiers.

The pharmaceutical compositions for use in the present invention can be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, vaginal, or rectal means.

In addition to the active ingredients (i.e., the MIST nucleic acid or polypeptide, or functional fragments thereof), the pharmaceutical compositions may contain suitable pharmaceutically acceptable carriers or excipients comprising auxiliaries which facilitate processing of the active compounds into preparations which can be used pharmaceutically. Further details on techniques for formulation and administration are provided in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained by the combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropyl-methylcellulose, or sodium carboxymethylcellulose; gums, including arabic and tragacanth, and proteins such as gelatin and collagen. If desired, disintegrating or solubilizing agents may be added, such as cross-linked polyvinyl pyrrolidone, agar, alginic acid, or a physiologically acceptable salt thereof, such as sodium alginate.

Dragee cores may be used in conjunction with physiologically suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification, or to characterize the quantity of active compound, i.e., dosage.

Pharmaceutical preparations which can be used orally include push-fit capsules made of gelatin, as well as soft, scaled capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. In addition, suspensions of the active compounds may be prepared as appropriate oily injection suspensions. Suitable lipophilic solvents or vehicles include fatty oils such as sesame oil, or synthetic fatty acid esters, such as ethyloleate or triglycerides, or liposomes. Optionally, the suspension may also contain suitable stabilizers or agents which increase the solubility of the compounds to allow for the preparation of highly concentrated solutions.

For topical or nasal administration, penetrants or permeation agents that are appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, and the like. Salts tend to be more soluble in aqueous solvents, or other protonic solvents, than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, combined with a buffer prior to use. After the pharmaceutical compositions have been prepared, they can be placed in an appropriate container and labeled for treatment of an indicated condition. For administration of the MIST product, such labeling would include amount, frequency, and method of administration.

Pharmaceutical compositions suitable for use in the present invention include compositions wherein the active ingredients are contained in an effective amount to achieve the intended purpose. The determination of an effective dose or amount is well within the capability of those skilled in the art. For any compound, the therapeutically effective dose can be estimated initially either in cell culture assays, e.g., using neoplastic cells, or in animal models, usually mice, rabbits, dogs, or pigs. The animal model may also be used to determine the appropriate concentration range and route of administration. Such information can then be used and extrapolated to determine useful doses and routes for administration in humans.

A therapeutically effective dose refers to that amount of active ingredient, for example, the MIST polypeptide, or active fragments thereof, antibodies to the MIST polypeptide, agonists or antagonists of the MIST polypeptide, which ameliorates, reduces, or eliminates the symptoms or condition. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio of toxic to therapeutic effects is the therapeutic index, which can be expressed as the ratio, $ED_{50}/LD_{50}$. The data obtained from cell culture assays and animal studies are used in determining a range of dosages for human use. Preferred dosage contained in a pharmaceutical composition is within a range of circulating concentrations that include the $ED_{50}$ with little or no toxicity. The dosage varies within this range depending upon the dosage form employed, sensitivity of the patient, and the route of administration.

The exact dosage will be determined by the practitioner, who will consider the factors related to the individual requiring treatment. Dosage and administration are adjusted to provide sufficient levels of the active moiety or to maintain the desired effect. Factors which may be taken into account include the severity of the individual's disease state, general health of the patient, age, weight, and gender of the patient, diet, time and frequency of administration, drug combination(s), reaction sensitivities, and tolerance/response to therapy. As a general guide, long-acting pharmaceutical compositions may be administered every 3 to 4 days, every week, or once every two weeks, depending on half-life and clearance rate of the particular formulation.

Normal dosage amounts may vary from 0.1 to 100,000 micrograms (□g), up to a total dose of about 1 gram (g), depending upon the route of administration. Guidance as to particular dosages and methods of delivery is provided in the literature and is generally available to practitioners in the art. Those skilled in the art will employ different formulations for nucleotides than for proteins or their inhibitors. Similarly, delivery of polynucleotides or polypeptides will be specific to particular cells, conditions, locations, and the like.

Assays and Diagnostics

In another embodiment of the present invention, antibodies which specifically bind to the MIST polypeptide may be used for the diagnosis of conditions or diseases characterized by expression (or overexpression) of the MIST polynucleotide or polypeptide, or in assays to monitor patients being treated with MIST polypeptide, or its agonists, antagonists, or inhibitors. The antibodies useful for diagnostic purposes may be prepared in the same manner as those described above for use in therapeutic methods. Diagnostic assays for the MIST polypeptide include methods which utilize the antibody and a label to detect the protein in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

Several assay protocols including ELISA, RIA, and FACS for measuring the MIST polypeptide are known in the art and provide a basis for diagnosing altered or abnormal levels of MIST polypeptide expression. Normal or standard values for MIST polypeptide expression are established by combining body fluids or cell extracts taken from normal mammalian subjects, preferably human, with antibody to the MIST polypeptide under conditions suitable for complex formation. The amount of standard complex formation may be quantified by various methods; photometric means are preferred. Quantities of the MIST polypeptide expressed in subject sample, control sample, and disease samples from biopsied tissues are compared with the standard values. Deviation between standard and subject values establishes the parameters for diagnosing disease.

According to another embodiment of the present invention, the polynucleotides encoding MIST polypeptide may be used for diagnostic purposes. The polynucleotides which may be used include oligonucleotide sequences, complementary RNA and DNA molecules, and PNAs. The polynucleotides may be used to detect and quantify MIST-encoding nucleic acid expression in biopsied tissues in which expression (or under- or overexpression) of MIST polynucleotide may be correlated with disease. The diagnostic assay may be used to distinguish between the absence, presence, and excess expression of MIST, and to monitor regulation of MIST polynucleotide levels during therapeutic treatment or intervention.

In a related aspect, hybridization with PCR probes which are capable of detecting polynucleotide sequences, including genomic sequences, encoding MIST polypeptide, or closely related molecules, may be used to identify nucleic acid sequences which encode the MIST polypeptide. The specificity of the probe, whether it is made from a highly specific region, e.g., about 8 to 10 or 12 or 15 contiguous nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding the MIST polypeptide, alleles thereof, or related sequences.

Probes may also be used for the detection of related sequences, and should preferably contain at least 50%, preferably greater than 80%, of the nucleotides encoding MIST polypeptide. The hybridization probes of this invention may be DNA or RNA and may be derived from the nucleotide sequence of SEQ ID NO:1, or from genomic sequence including promoter, enhancer elements, and introns of the naturally occurring MIST protein.

Methods for producing specific hybridization probes for DNA encoding the MIST polypeptide include the cloning of nucleic acid sequence that encodes the MIST polypeptide, or MIST derivatives, into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of detector/reporter groups, e.g., radionuclides such as $^{32}P$ or $^{35}S$, or enzymatic labels, such as alkaline phosphatase coupled to the probe via avidin/biotin coupling systems, and the like.

The polynucleotide sequence encoding the MIST polypeptide may be used in Southern or Northern analysis, dot blot, or other membrane-based technologies; in PCR technologies; or in dip stick, pin, ELISA or chip assays utilizing fluids or tissues from patient biopsies to detect the status of, e.g., levels or overexpression of MIST, or to detect altered MIST expression. Such qualitative or quantitative methods are well known in the art.

In a particular aspect, the nucleotide sequence encoding the MIST polypeptide may be useful in assays that detect activation or induction of various B- and T-cell-related neoplasms or cancers, particularly those mentioned supra. The nucleotide sequence encoding the MIST polypeptide may be labeled by standard methods, and added to a fluid or tissue sample from a patient under conditions suitable for the formation of hybridization complexes. After a suitable incubation period, the sample is washed and the signal is quantified and compared with a standard value. If the amount of signal in the biopsied or extracted sample is significantly altered from that of a comparable control sample, the nucleotide sequence has hybridized with nucleotide sequence present in the sample, and the presence of altered levels of nucleotide sequence encoding the MIST polypeptide in the sample indicates the presence of the associated disease. Such assays may also be used to evaluate the efficacy of a particular therapeutic treatment regimen in animal studies, in clinical trials, or in monitoring the treatment of an individual patient.

To provide a basis for the diagnosis of disease associated with expression of MIST, a normal or standard profile for expression is established. This may be accomplished by combining body fluids or cell extracts taken from normal subjects, either animal or human, with a sequence, or a fragment thereof, which encodes the MIST polypeptide, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject (patient) values is used to establish the presence of disease.

Once disease is established and a treatment protocol is initiated, hybridization assays may be repeated on a regular basis to evaluate whether the level of expression in the patient begins to approximate that which is observed in a normal individual. The results obtained from successive assays may be used to show the efficacy of treatment over a period ranging from several days to months.

With respect to cancer, the presence of an abnormal amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier, thereby preventing the development or further progression of the cancer.

Additional diagnostic uses for oligonucleotides designed from the nucleic acid sequence encoding the MIST polypeptide may involve the use of PCR. Such oligomers may be chemically synthesized, generated enzymatically, or produced from a recombinant source. Oligomers will preferably comprise two nucleotide sequences, one with sense orientation (5'→3') and another with antisense (3'→5'), employed under optimized conditions for identification of a specific gene or condition. The same two oligomers, nested sets of oligomers, or even a degenerate pool of oligomers may be employed under less stringent conditions for detection and/or quantification of closely related DNA or RNA sequences.

Methods suitable for quantifying the expression of MIST include radiolabeling or biotinylating nucleotides, co-amplification of a control nucleic acid, and standard curves onto which the experimental results are interpolated (P. C. Melby et al., 1993, *J. Immunol. Methods,* 159:235-244; and C. Duplaa et al., 1993, *Anal Biochem.,* 229-236). The speed of quantifying multiple samples may be accelerated by running the assay in an ELISA format where the oligomer of interest is presented in various dilutions and a spectrophotometric or calorimetric response gives rapid quantification.

In another embodiment of the present invention, oligonucleotides, or longer fragments derived from the MIST polynucleotide sequence described herein may be used as targets in a microarray. The microarray can be used to monitor the expression level of large numbers of genes simultaneously (to produce a transcript image), and to identify genetic variants, mutations and polymorphisms. This information may be used to determine gene function, to understand the genetic basis of a disease, to diagnose disease, and to develop and monitor the activities of therapeutic agents. In a particular aspect, the microarray is prepared and used according to the methods described in WO 95/11995 (Chee et al.); D. J. Lockhart et al., 1996, *Nature Biotechnology,* 14:1675-1680; and M. Schena et al., 1996, *Proc. Natl. Acad. Sci. USA,* 93:10614-10619). Microarrays are further described in U.S. Pat. No. 6,015,702 to P. Lal et al.

In another embodiment of this invention, the nucleic acid sequence which encodes the MIST polypeptide may also be used to generate hybridization probes which are useful for mapping the naturally occurring genomic sequence. The sequences may be mapped to a particular chromosome, to a specific region of a chromosome, or to artificial chromosome constructions (HACs), yeast artificial chromosomes (YACs), bacterial artificial chromosomes (BACs), bacterial P1 constructions, or single chromosome cDNA libraries, as reviewed by C. M. Price, 1993, *Blood Rev.,* 7:127-134 and by B. J. Trask, 1991, *Trends Genet.,* 7:149-154.

In another embodiment of the present invention, the MIST polypeptide, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between the MIST polypeptide, or portion thereof, and the agent being tested, may be measured utilizing techniques commonly practiced in the art and as described above.

Another technique for drug screening which may be used provides for high throughput screening of compounds having suitable binding affinity to the protein of interest as described in WO 84/03564. In this method, as applied to the MIST protein, large numbers of different small test compounds are synthesized on a solid substrate, such as plastic pins or some other surface. The test compounds are reacted with the MIST polypeptide, or fragments thereof, and washed. Bound polypeptide is then detected by methods well known in the art. Purified MIST polypeptide can also be coated directly onto plates for use in the aforementioned drug screening techniques. Alternatively, non-neutralizing antibodies can be used to capture the peptide and immobilize it on a solid support.

In a further embodiment of this invention, competitive drug screening assays can be used in which neutralizing antibodies capable of binding MIST polypeptide specifically compete with a test compound for binding to MIST polypeptide. In this manner, the antibodies can be used to detect the presence of any peptide which shares one or more antigenic determinants with the MIST polypeptide.

Transgenics and Knock Outs

The present invention further encompasses transgenic non-human mammals, preferably mice, that comprise a recombinant expression vector harboring a nucleic acid sequence that encodes human MIST comprising the amino acid sequence of SEQ ID NO:2. The invention also relates to transgenic non-human mammals that comprise a recombinant expression vector harboring a nucleic acid sequence that encodes human MIST comprising the amino acid sequence of SEQ ID NO:3. In addition, the invention also relates to transgenic non-human mammals that comprise a recombinant expression vector harboring a nucleic acid sequence that encodes human MIST comprising the amino acid sequence of SEQ ID NO:5.

Transgenic non-human mammals useful to produce recombinant proteins are well known to the skilled practitioner, as are the expression vectors necessary and the techniques for generating transgenic animals. Generally, the transgenic animal comprises a recombinant expression vector in which the nucleotide sequence that encodes human MIST is operably linked to a tissue specific promoter whereby the coding sequence is only expressed in that specific tissue. For example, the tissue specific promoter can be a mammary cell specific promoter and the recombinant protein so expressed is recovered from the animal's milk.

The transgenic animals, particularly transgenic mice, containing a nucleic acid molecule which encodes human MIST may be used as animal models for studying in vivo the overexpression of MIST and for use in drug evaluation and discovery efforts to find compounds effective to inhibit or modulate the activity of MIST, such as for example compounds for treating B- and T-cell neoplasms. One having ordinary skill in the art using standard techniques, such as those taught in U.S. Pat. No. 4,873,191, issued Oct. 10, 1989 to Wagner and in U.S. Pat. No. 4,736,866, issued Apr. 12, 1988 to Leder, can produce transgenic animals which produce the human MIST, or splice variants thereof, and use the animals in drug evaluation and discovery projects.

Another aspect of the present invention relates to knockout mice and methods of using the same. In particular, transgenic mice may be generated which are homozygous for a mutated, non-functional MIST gene which is introduced into the animals using well known techniques. The knock-out mice produce no functional MIST and thus are useful to study the function of MIST. Furthermore, the mice may be used in assays to study the effect of test compounds in MIST deficient animals. For instance, MIST-deficient mice can be used to determine if, how and to what extent MIST inhibitors will effect the animal and thus address concerns associated with inhibiting the activity of the molecule.

Methods of generating genetically deficient "knock out" mice are well known and are disclosed in M. R. Capecchi, 1989, *Science,* 244:1288-1292 and P. Li et al., 1995, *Cell,* 80:401-411. The human MIST cDNA clone can be used to isolate a murine MIST genomic clone. The genomic clone can be used to prepare a MIST targeting construct which can disrupt the MIST gene in the mouse by homologous recombination. The targeting construct contains a non-functioning portion of the MIST gene which inserts in place of the functioning portion of the native mouse gene. The non-functioning insert generally contains an insertion in the exon that encodes the active region of MIST. The targeting construct can contain markers for both positive and negative selection. The positive selection marker allows for the selective elimination of cells which do not carry the marker, while the negative selection marker allows for the elimination of cells that carry the marker.

For example, a first selectable marker is a positive marker that will allow for the survival of cells carrying it. In some instances, the first selectable marker is an antibiotic resistance gene, such as the neomycin resistance gene, which can be placed within the coding sequence of the MIST gene to render it non-functional, while at the same time rendering the construct selectable. The antibiotic resistance gene is within the homologous region which can recombine with native sequences. Thus, upon homologous recombination, the non-functional and antibiotic resistance selectable gene sequences will be taken up. Knock-out mice may be used as models for studying B- and T-cell related disorder and hyperactivity and screening compounds for treating these disorders.

The targeting construct also contains a second selectable marker which is a negative selectable marker. Cells with the negative selectable marker will be eliminated. The second selectable marker is outside the recombination region. Thus, if the entire construct is present in the cell, both markers will be present. If the construct has recombined with native sequences, the first selectable marker will be incorporated into the genome and the second will be lost. The herpes simplex virus thymidine kinase (HSV tk) gene is an example of a negative selectable marker which can be used as a second marker to eliminate cells that carry it. Cells with the HSV tk gene are selectively killed in the presence of gangcyclovir.

Cells are transfected with targeting constructs and then selected for the presence of the first selection marker and the absence of the second. Constructs/DNA are then injected into the blastocyst stage and implanted into pseudopregnant females. Chimeric offspring which are capable of transferring the recombinant genes in their germline are selected, mated and their offspring examined for heterozygous carriers of the recombined genes. Mating of the heterozygous offspring can then be used to generate fully homozygous offspring which constitute MIST-deficient knock-out mice.

Motifs and Descriptions

The MIST polypeptides of the present invention were determined to comprise several phosphorylation sites based upon the Motif algorithm (Genetics Computer Group, Inc.). The phosphorylation of such sites may regulate biological activity of the MIST polypeptide. For example, phosphorylation at specific sites may be involved in regulating the ability of the protein to associate or bind to other molecules (e.g., proteins, ligands, substrates, DNA, etc.). In the present case, phosphorylation may modulate the ability of the MIST polypeptide to associate with other polypeptides, particularly cognate ligands for MIST, or its ability to modulate certain cellular signal pathways.

Specifically, the MIST polypeptide was predicted to comprise three tyrosine phosphorylation sites using the Motif algorithm (Genetics Computer Group, Inc.). Such sites are phosphorylated at the tyrosine amino acid residue. The consensus pattern for tyrosine phosphorylation sites is as follows: [RK]-x(2)-[DE]-x(3)-Y, or [RK]-x(3)-[DE]-x(2)-Y, where Y represents the phosphorylation site and 'x' represents an intervening amino acid residue. Additional information specific to tyrosine phosphorylation sites can be found in Patschinsky T. et al., *Proc. Natl. Acad. Sci. U.S.A.*, 79:973-977 (1982); Hunter T., *J. Biol. Chem.*, 257:4843-4848 (1982), and Cooper J. A. et al., *J. Biol. Chem.*, 259:7835-7841 (1984), which are hereby incorporated herein by reference.

The following tyrosine phosphorylation site polypeptides are preferably encompassed by the present invention: VLD-GAKGHSDDDYDDPEL (SEQ ID NO:23); KILPARPIKE-SEYADTHY (SEQ ID NO:24), and/or RDCSTKSKEEPYV-LAVF (SEQ ID NO:25). Polynucleotides encoding these polypeptides are also provided. The present invention also encompasses the use of these MIST tyrosine phosphorylation site polypeptides as immunogenic and/or antigenic epitopes as described elsewhere herein.

The MIST polypeptide was predicted to comprise nine protein kinase C (PKC) phosphorylation sites using the Motif algorithm (Genetics Computer Group, Inc.). In vivo, PKC exhibits a preference for the phosphorylation of serine or threonine residues. The PKC phosphorylation sites have the following consensus pattern: [ST]-x-[RK], where S or T represents the site of phosphorylation and 'x' is an intervening amino acid residue. Additional information regarding PKC phosphorylation sites can be found in Woodget J. R. et al., *Eur. J. Biochem.*, 161:177-184 (1986), and Kishimoto A. et al., *J. Biol. Chem.*, 260:12492-12499 (1985); which are hereby incorporated by reference herein.

Preferably, the following PKC phosphorylation site polypeptides are encompassed by the present invention: QGNRKTTKEGSND (SEQ ID NO:26); EETWQSIKILPAR (SEQ ID NO:27); IKGDASVRKNKIP (SEQ ID NO:28); PPEPESSRPPLSQ (SEQ ID NO:29); SRPPLSQRHTFPE (SEQ ID NO:30); PYKYTSWRPPFPK (SEQ ID NO:31); PFPKRSDRKDVQH (SEQ ID NO:32); and/or LVRDCSTK-SKEEP (SEQ ID NO:33). Polynucleotides encoding these polypeptides are also provided. The present invention also encompasses the use of the MIST PKC phosphorylation site polypeptides as immunogenic and/or antigenic epitopes as described elsewhere herein.

The MIST polypeptide was predicted to comprise eight casein kinase II phosphorylation sites using the Motif algorithm (Genetics Computer Group, Inc.). Casein kinase II (CK-2) is a protein serine/threonine kinase whose activity is independent of cyclic nucleotides and calcium. CK-2 has the ability to phosphorylate many different proteins. The substrate specificity of this enzyme can be summarized as follows: (1) Under comparable conditions Ser is favored over Thr.; (2) An acidic residue (either Asp or Glu) must be present three residues from the C-terminus of the phosphate acceptor site; (3) Additional acidic residues in positions +1, +2, +4 and +5 increase the phosphorylation rate. Most physiological substrates have at least one acidic residue in these positions; (4) Asp is preferred over Glu as the provider of acidic determinants; and (5) A basic residue at the N-terminus of the acceptor site decreases the phosphorylation rate, while an acidic residue will increase it.

A consensus pattern for a typical casein kinase II phosphorylation site is as follows: [ST]-x(2)-[DE], wherein 'x' represents any amino acid, and S or T is the phosphorylation site. Additional information specific to aminoacyl-transfer RNA synthetase class-II domains can be found in the following publication: Pinna L. A., *Biochim. Biophys. Acta*, 1054:267-284 (1990); which is hereby incorporated by reference herein in its entirety.

The following casein kinase II phosphorylation site polypeptides are preferably encompassed by the present invention: QGNRKTTKEGSNDL (SEQ ID NO:34); GAKGHSDDDYDDPE (SEQ ID NO:35); TWNTQTRL- ERVDKP (SEQ ID NO:36); LSQRHTFPEVQRMP (SEQ ID NO:37); MPSQISLRDLSEVL (SEQ ID NO:38); PPASCSPHENILPY (SEQ ID NO:39); DCSTKSKEEPYVLA (SEQ ID NO:40); and/or DEKFDSVEDIIEHY (SEQ ID NO:41). Polynucleotides encoding these polypeptides are also provided. The present invention also encompasses the use of the casein kinase II phosphorylation site polypeptides as an immunogenic and/or antigenic epitope as described elsewhere herein.

The MIST polypeptide was further predicted to comprise two cAMP- and cGMP-dependent protein kinase phosphorylation sites using the Motif algorithm (Genetics Computer Group, Inc.). There have been a number of studies relating to the specificity of cAMP- and cGMP-dependent protein kinases. Both types of kinases appear to share a preference for the phosphorylation of serine or threonine residues found close to at least two consecutive N-terminal basic residues.

A consensus pattern for cAMP- and cGMP-dependent protein kinase phosphorylation sites is as follows: [RK](2)-x-[ST], where "x" represents any amino acid, and S or T is the phosphorylation site. Additional information specific to cAMP- and cGMP-dependent protein kinase phosphorylation sites can be found in the following publications: Fremisco J. R. et al., *J. Biol. Chem.*, 255:4240-4245 (1980); Glass D. B. and Smith S. B., *J. Biol. Chem.*, 258:14797-14803 (1983); and Glass D. B., et al., *J. Biol. Chem.*, 261:2987-2993 (1986); which are hereby incorporated by reference herein in their entirety.

In preferred embodiments, the following cAMP- and cGMP-dependent protein kinase phosphorylation site polypeptide is encompassed by the present invention: NRQGNRKTTKEGSN (SEQ ID NO:42). Polynucleotides encoding this polypeptide are also provided. The present invention also encompasses the use of this cAMP- and cGMP-dependent protein kinase phosphorylation site polypeptide as an immunogenic and/or antigenic epitope as described elsewhere herein.

The MIST polypeptide has been shown to comprise three glycosylation sites according to the Motif algorithm (Genetics Computer Group, Inc.). As discussed more specifically herein, protein glycosylation is thought to serve a variety of functions, including augmentation of protein folding, inhibition of protein aggregation, regulation of intracellular trafficking to organelles, increasing resistance to proteolysis, modulation of protein antigenicity, and mediation of intercellular adhesion.

Asparagine glycosylation sites have the following consensus pattern, N-{P}-[ST]-{P}, where N represents the glycosylation site. However, it is well known that potential N-glycosylation sites are specific to the consensus sequence Asn-Xaa-Ser/Thr. However, the presence of the consensus tripeptide is not sufficient to conclude that an asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to asparagine glycosylation can be found in the following publications, which are hereby incorporated by reference herein: Marshall R. D., *Annu. Rev. Biochem.*, 41:673-702 (1972); Pless D. D. and Lennarz W. J., *Proc. Natl. Acad. Sci. U.S.A.*, 74:134-138 (1977); Bause E., *Biochem. J.*, 209:331-336 (1983); Gavel Y. and von Heijne G., *Protein Eng.*, 3:433-442 (1990); and Miletich J. P. and Broze G. J. Jr., *J. Biol. Chem.*, 265:11397-11404 (1990).

In preferred embodiments, the following glycosylation site polypeptides are encompassed by the present invention: DLKFQNFSLPKNRS (SEQ ID NO:43), FSLPKNRSWPRINS (SEQ ID NO:44), and/or SFTTSNHSVQNRDH (SEQ ID NO:45). Polynucleotides encoding these polypeptides are also provided. The present invention also encompasses the use of these MIST asparagine glycosylation site polypeptides as immunogenic and/or antigenic epitopes as described elsewhere herein.

The MIST polypeptide was predicted to comprise two N-myristylation sites using the Motif algorithm (Genetics Computer Group, Inc.). An appreciable number of eukaryotic proteins are acylated by the covalent addition of myristate (a $C_{14}$-saturated fatty acid) to their N-terminal residue via an amide linkage. The sequence specificity of the enzyme responsible for this modification, myristyl CoA:protein N-myristyl transferase (NMT), has been derived from the sequence of known N-myristylated proteins and from studies using synthetic peptides. The specificity seems to be the following: i) The N-terminal residue must be glycine; ii) In position 2, uncharged residues are allowed; iii) Charged residues, proline and large hydrophobic residues are not allowed; iv) In positions 3 and 4, most, if not all, residues are allowed; v) In position 5, small uncharged residues are allowed (Ala, Ser, Thr, Cys, Asn and Gly). Serine is favored; and vi) In position 6, proline is not allowed.

A consensus pattern for N-myristylation is as follows: G-{EDRKHPFYW}-x(2)-[STAGCN]-{P}, wherein 'x' represents any amino acid, and G is the N-myristylation site. Additional information specific to N-myristylation sites may be found in the following publications: Towler D. A. et al., *Annu. Rev. Biochem.*, 57:69-99 (1988); and Grand R. J. A., *Biochem. J.*, 258:625-638 (1989); which are hereby incorporated by reference herein in their entirety.

The following N-myristylation site polypeptides are preferably encompassed by the present invention: TMNRQGNRKTTKEGSN (SEQ ID NO:46), and/or RDHRGGMQPCSPQRCQ (SEQ ID NO:47). Polynucleotides encoding these polypeptides are also provided. The present invention further encompasses the use of these MIST N-myristylation site polypeptides as immunogenic and/or antigenic epitopes as described elsewhere herein.

The MIST polypeptide has been shown to comprise one RGD cell attachment site domain according to the Motif algorithm (Genetics Computer Group, Inc.). The sequence Arg-Gly-Asp, found in fibronectin, is crucial for its interaction with its cell surface receptor, an integrin. What has been called the 'RGD' tripeptide is also found in the sequences of a number of other proteins, where it has been shown to play a role in cell adhesion. Non-limiting examples of these proteins are the following: some collagen forms, fibrinogen, vitronectin, von Willebrand factor (VWF), snake disintegrins, and slime mold discoidins. The 'RGD' tripeptide is also found in other proteins where it may serve the same purpose. A consensus pattern for RGD cell attachment sites is the following: R-G-D. Additional information relating to RGD cell attachment site domains may be found in the following publications, which are hereby incorporated by reference herein: Ruoslahti E. and Pierschbacher M. D., *Cell*, 44:517-518 (1986); and d'Souza S. E. et al., *Trends Biochem. Sci.*, 16:246-250 (1991).

In a preferred embodiment, the following RGD cell attachment site domain polypeptide is encompassed by the present invention: LGTGLRGDEKFDS (SEQ ID NO:48). Polynucleotides encoding this polypeptide are also provided. The present invention also encompasses the use of this RGD cell attachment site domain polypeptide as an immunogenic and/or antigenic epitope as described elsewhere herein.

Method of Enhancing the Biological Activity/Functional Characteristics of the Present Invention Through Molecular Evolution Although many of the most biologically active proteins known are highly effective for their specified function in an organism, they often possess characteristics that make them undesirable for transgenic, therapeutic, pharmaceutical and/or industrial applications. Among these traits, a short physiological half-life is the most prominent problem, and is present either at the level of the protein, or at the level of the mRNA. The ability to extend the half-life of a protein would be particularly important for its use, for example, in gene therapy, transgenic animal production, the bioprocess production and purification of the protein and the use of the protein as a chemical modulator, among others. Therefore, there is a need to identify novel variants of isolated proteins possessing characteristics which enhance their application as a therapeutic for treating diseases of animal origin, in addition to the protein's applicability to common industrial and pharmaceutical applications.

Thus, one aspect of the present invention relates to the ability to enhance specific characteristics of the polypeptides of the present invention through directed molecular evolution. Such an enhancement may, in a non-limiting example, benefit the utility of the newly described protein products as an essential component in a kit; the physical attributes of a protein of the invention, such as its solubility, structure, or codon optimization; the specific biological activity of a protein of the invention, including any associated enzymatic activity; the enzyme kinetics of the proteins of the invention (if applicable); the Ki, Kcat, Km, Vmax, Kd, protein-protein activity, protein-DNA binding activity, antagonist/inhibitory activity (including direct or indirect interaction), agonist activity (including direct or indirect interaction) of the proteins of the invention; the antigenicity of the proteins of the invention (e.g., where it would be desirable to either increase or decrease the antigenic potential of the protein); the immunogenicity of the proteins of the invention; the ability of a protein of the invention to form dimers, trimers, or multimers with either itself or other proteins; the antigenic efficacy of a protein of the invention, including its subsequent use a preventative treatment for disease or disease states, or as an effector for targeting diseased genes.

Moreover, the ability to enhance specific characteristics of a protein may also be applicable to changing the characterized activity of an enzyme to an activity completely unrelated to its initially characterized activity. Other desirable enhancements of a protein of the present invention would be specific to each individual protein, and would thus be well known in the art and contemplated by the present invention.

For example, an engineered MIST SH2 adapter protein may alter the adapter's binding specificity or affinity relative to its downstream, and/or upstream effectors; and/or may affect the adapter protein's ability to become phosphorylated, and/or affect the ability of the adapter protein to become activated, and/or affect its ability to transduce a signal, and/or affect its ability to bind with GrB2 and/or PLC-gamma, and/or affect its ability to participate in ras signaling cascade, and/or affect its ability to become activated through a TCR-dependent mechanism and signaling pathways, and/or affect its ability to participate in receptor-mediated mast cell degranulation, and/or affect its ability to participate in BCR-dependent mechanisms and signaling pathways. Alternatively, an engineered adapter protein can be constitutively active upon binding of its cognate ligand. Also, alternatively, an engineered adapter protein may be constitutively active in the absence of ligand binding.

In yet another example, an engineered adapter protein may be capable of being activated with less than all of the regulatory factors and/or conditions typically required for adapter protein activation (e.g., phosphorylation, conformational changes, etc.). Such adapters would be useful in screens to identify adapter protein modulators, among other uses described herein.

Directed evolution is comprised of several steps. The first step involves establishing a library of variants for the gene or protein of interest. The most important step is then selecting for those variants which possess the activity to be identified. The design of the screen is essential, since the screen should be selective enough to eliminate non-useful variants, but not so stringent as to eliminate all variants. The last step is repeating the above steps using the best variant from the previous screen. Each successive cycle can then be tailored as necessary, such as by increasing the stringency of the screen, for example.

Over the years, there have been a number of methods developed to introduce mutations into macromolecules. Some of these methods include, random mutagenesis, "error-prone" PCR, chemical mutagenesis, site-directed mutagenesis, and other methods well known in the art (for a comprehensive listing of current mutagenesis methods, see T. Maniatis et al., Molecular Cloning: A Laboratory Manual, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutagenesis has been the most widely recognized method to date. Typically, this has been carried out either through the use of "error-prone" PCR (as described in Moore, J. et al, *Nature Biotechnology* 14:458, (1996), or through the application of randomized synthetic oligonucleotides corresponding to specific regions of interest (as described by Derbyshire, K. M. et al, *Gene,* 46:145-152, (1986), and Hill, D. E. et al, *Methods Enzymol.,* 55:559-568, (1987)). Both approaches have limits to the level of mutagenesis that can be obtained. However, either approach enables the investigator to effectively control the rate of mutagenesis. This is particularly important, since mutations beneficial to the activity of the enzyme are fairly rare. In fact, using too high a level of mutagenesis may counter or inhibit the desired benefit of a useful mutation.

While both of the aforementioned methods are effective for creating randomized pools of macromolecule variants, a third method, termed "DNA Shuffling", or "sexual PCR" (Stemmer, W. P. C., *PNAS,* 91:10747, (1994)) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the invention. The new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, a randomly digested pool of small DNA fragments of a given gene (i.e., a MIST gene according to this invention) is created by DNase I digestion.

The resulting fragments are then introduced into an "error-prone" PCR assembly reaction. During the PCR reaction, the randomly sized DNA fragments hybridize not only to their cognate strand, but also to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments, thus further diversifying the potential hybridization sites during the annealing step of the reaction.

A variety of reaction conditions can be employed to carry out the DNA shuffling reaction. However, specific reaction conditions for DNA shuffling are provided hereinbelow for guidance, (see also, *PNAS*, 91:10747, (1994). Briefly: the DNA substrate that is to be subjected to the DNA shuffling reaction is prepared. The preparation may be in the form of simply purifying the DNA from contaminating cellular material, chemicals, buffers, oligonucleotide primers, deoxynucleotides, RNAs, etc., and may utilize commercially available DNA purification kits, such as those provided by Qiagen, Inc., or by Promega, Corp., for example.

Once the DNA substrate has been purified, it is subjected to DNase I digestion. About 2-4 μg of the DNA substrate(s) is digested with 0.0015 units of DNase I (Sigma) per μl in 100 μl of 50 mM Tris-HCL, pH 7.4/1 mM $MgCl_2$ for 10-20 minutes at room temperature. The resulting fragments of 10-50 bp are then purified by subjecting them to agarose gel electrophoresis (e.g., a 2% low-melting point agarose gel) and then transferring them onto DE81 ion-exchange paper (Whatman); the fragment can also be purified using MICROCON® concentrators (Amicon) of the appropriate molecular weight cutoff, or by using oligonucleotide purification columns (Qiagen), in addition to other methods known in the art. If using DE81 ion-exchange paper, the 10-50 bp fragments are then eluted from said paper using 1M NaCl, followed by ethanol precipitation.

The resulting purified fragments would then be subjected to a PCR assembly reaction by re-suspension in a PCR mixture containing: 2 mM of each dNTP, 2.2 mM $MgCl_2$, 50 mM KCl, 10 mM Tris-HCL, pH 9.0, and 0.1% Triton X-100®, at a final fragment concentration of 10-30 ng/μl. No primers are added at this point.

Taq DNA polymerase (Promega) is used at 2.5 units per 100 μl of reaction mixture. A PCR program used is 94 C for 60 s; 94 C for 30 s, 50-55 C for 30 s, and 72 C for 30 s using 3045 cycles, followed by 72 C for 5 min using an MJ RESEARCH® (Cambridge, Mass.) PTC-150 thermocycler. After the assembly reaction is completed, a 1:40 dilution of the resulting primerless product is then introduced into a PCR mixture (using the same buffer mixture used for the assembly reaction) containing 0.8 μm of each primer and subjecting this mixture to 15 cycles of PCR (using 94 C for 30 s, 50 C for 30 s, and 72 C for 30 s). The referred primers are primers corresponding to the nucleic acid sequences of the polynucleotide(s) utilized in the shuffling reaction. Such primers can contain modified nucleic acid base pairs using methods known in the art and referred to elsewhere herein, or can contain additional sequences (i.e., for adding restriction sites, mutating specific base pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations are understood and practiced by the skilled artisan and are encompassed by the invention. The DNA shuffling method can also be tailored to the desired level of mutagenesis using the methods described by Zhao, et al. (*Nucl Acid Res.*, 25(6):1307-1308, (1997)).

As described above, once the randomized pool has been created, it can then be subjected to a specific screen to identify the variant possessing the desired characteristic(s). Once the variant has been identified, DNA corresponding to the variant can be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology are found in the following publications: J. C. Moore et al., *J. Mol. Biol.*, 272:336-347, (1997), F. R. Cross et al., *Mol. Cell. Biol.*, 18:2923-2931, (1998), and A. Crameri et al., *Nat. Biotech.*, 15:436-438, (1997).

DNA shuffling has several advantages. First, it makes use of beneficial mutations. When combined with screening, DNA shuffling allows the discovery of the best mutational combinations and does not assume that the best combination contains all the mutations in a population. Second, recombination occurs simultaneously with point mutagenesis. An effect of forcing DNA polymerase to synthesize full-length genes from the small fragment DNA pool is a background mutagenesis rate. In combination with a stringent selection method, enzymatic activity has been evolved to up to a 16000-fold increase over the wild-type form of the enzyme. In essence, the background mutagenesis yielded the genetic variability on which recombination acted to enhance the activity.

A third feature of recombination is that it can be used to remove deleterious mutations. As discussed above, during the process of the randomization, for every one beneficial mutation, there may be at least one or more neutral or inhibitory mutation(s). Such mutation(s) can be removed by including in the assembly reaction an excess of the wild-type random-size fragments, in addition to the random-size fragments of the selected mutant from the previous selection. During the subsequent selection, some of the most active variants of the polynucleotide/polypeptide/enzyme should have lost the inhibitory mutations.

Finally, recombination enables parallel processing. This represents a significant advantage, since there are likely to be multiple characteristics that would make a protein more desirable (e.g. solubility, activity, etc.). Since it is increasingly difficult to screen for more than one desirable trait at a time, other methods of molecular evolution tend to be inhibitory. However, using recombination, it is possible to combine the randomized fragments of the best representative variants for the various traits, and then to select for multiple properties at one time.

DNA shuffling can also be applied to the polynucleotides and polypeptides of the present invention to decrease their immunogenicity in a specified host, particularly if the polynucleotides and polypeptides provide a therapeutic use. For example, a particular variant of the present invention may be created and isolated using DNA shuffling technology. Such a variant may have all of the desired characteristics, though it may be highly immunogenic in a host due to its novel intrinsic structure. Specifically, the desired characteristic may cause the polypeptide to have a non-native structure which is no longer be recognized as a "self" molecule, but rather as a "foreign" molecule, and thus activate a host's immune response directed against the novel variant. Such a limitation can be overcome, for example, by including a copy of the gene sequence for a xenobiotic ortholog of the native protein with the gene sequence of the novel variant gene in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel variant that provided the desired characteristics.

Likewise, the invention encompasses the application of DNA shuffling technology to the evolution of polynucleotides and polypeptides of the invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homolog sequences, additional homologous sequences, additional non-homologous sequences, sequences from another species, and any number and combination of the above.

In addition to the described methods described above, there are a number of related methods that may also be applicable, or desirable, in certain cases. Representative among these are the methods discussed in PCT applications WO 98/31700, and WO 98/32845, which are hereby incorporated by reference. Furthermore, related methods can also be applied to the polynucleotide sequences of the present invention in order to evolve and create ideal variants for use in gene therapy, protein engineering, evolution of whole cells containing the variant, or in the evolution of entire enzyme pathways, containing polynucleotides of the invention, such as described in PCT applications WO 98/13485, WO 98/13487, WO 98/27230, WO 98/31837, and Crameri, A. et al., *Nat. Biotechnol.,* 15:436-438, (1997).

Additional methods of applying "DNA Shuffling" technology to the polynucleotides and polypeptides of the present invention, including their proposed applications, may be found in U.S. Pat. No. 5,605,793; PCT Application No. WO 95/22625; PCT Application No. WO 97/20078; PCT Application No. WO 97/35966; and PCT Application No. WO 98/42832. PCT Application No. WO 00/09727 specifically provides methods for applying DNA shuffling to the identification of herbicide selective crops which could be applied, with appropriate modification, if necessary, to the polynucleotides and polypeptides of the present invention. In addition, PCT Application No. WO 00/12680 provides methods and compositions for generating, modifying, adapting and optimizing polynucleotide sequences that confer detectable phenotypic properties on plant species; each of the above is hereby incorporated in its entirety herein for all purposes.

EXAMPLES

The Examples below are provided to illustrate the subject invention and are not intended to limit the invention.

Example 1

Methods

Cloning of the Full Length Human MIST Gene

Genomic sequences in the NIH GENBANK® public database were searched for novel SH2 domain-containing genes, using an SH2 domain hidden Markov model (HMM) from the Pfam database (A. Bateman et al., 2000, "The Pfam protein families database", *Nucleic Acids Res.,* 28:263-266) and the Genewise/Wise2 software package (Wise2 Documentation (version 2.1.20 stable), Ewan Birney, Richard Copley Sanger Centre, Wellcome Trust Genome Campus, Hinxton, Cambridge B10 1SA, England). Using the above software to predict a potential gene, or transcribed sequences as part of a gene, one of the novel predicted gene fragments showed significant homology to SH2 domains of the human BLNK and SLP-76 proteins. To further elucidate the complete structure of this gene, full-length cloning experiments were performed using the GENETRAPPER® methodology (Life Technologies, MD). Briefly, PCR primers PY474 (5'-tggtacattggagaatacag-3'), (SEQ ID NO:8), and PY475 (5'-gctgattcctctccaggaa-3'), (SEQ ID NO:9), were used to screen a human kidney cDNA library (Life Technologies, MD).

A strong positive PCR product was identified in a human spleen cDNA library the plasmid pCMVSPORT (Life Technologies, MD). This dsDNA plasmid library was converted to ssDNA using Gene II and Exonuclease III. Hybrids between the biotinylated oligo PY471

(5'-gtggaagaggcattcatgaaggagaacaag-3'), (SEQ ID NO:10), and ssDNA were formed and then captured on paramagnetic beads (D. A. Tagle et al., 1993, *Nature,* 361:751-753). After washing, the ssDNA was released and converted to dsDNA by DNA polymerase. Following transformation and plating in *E. coli* DH10B, positive clones were identified by PCR analysis. Through this technique, positive clones for this novel gene were identified. Sequence analysis indicated that three of the clones contained the full-length coding region. Additional sequencing primers, namely, PY641: 5'-gtaaggatcttggactctgg-3' (SEQ ID NO:11); PY642: 5'-ctccatccaggactgcagca-3' (SEQ ID NO:12); PY643: 5'-ggtgaatacagttgcaagtc-3' (SEQ ID NO:13); PY644: 5'-gagcttcggatggaagagac-3' (SEQ ID NO:14); PY645: 5'-tacatgtgccatgctggtgc-3' (SEQ ID NO:15); PY646: 5'-ctggaggctggcatctctga-3' (SEQ ID NO:16); PY647: 5'-agtggctgagtgaggtgaca-3' (SEQ ID NO:17); PY648: 5'-acttgtcttgcactgactgc-3' (SEQ ID NO:18); PY649: 5'-cactgagtgagctgatatgg-3' (SEQ ID NO:19); PY650: 5'-aggcagtggaagaggcattca-3' (SEQ ID NO:20); PY651: 5'-ttgcctctgtagcctggtct-3' (SEQ ID NO:21); PY652: 5'-tacaggacactgcgctgcct-3' (SEQ ID NO:22) were synthesized and used to sequence the entire clones. The plasmids were prepared using the mini-preparation protocol of QIAGEN® (QIAgen Inc., Valencia, Calif.) and were subjected to sequencing. The vector for these cDNA inserts is pCMVSPORT2 with cloning sites SalI (5'-end) and NotI (3'-end). Sequence analyses were performed using the GCG®/Wisconsin package (Genetics Computer Group, Madison, Wis.). As described herein, two of the clones encoded splice variants of MIST (FIGS. 4A-4B through 9A-9B), clones #7 and #12, respectively, and one clone encoded the full-length MIST cDNA. (FIGS. 1A-1B through 3A-3B, clone #8).

Sequence Analysis

As shown in FIGS. 3A-3B, sequencing of one of the isolated cDNA clones, clone #8, showed that this isolate has an 1851 nucleotide coding region, encoding a polypeptide of 443 amino acids. An SH2 domain was observed at the C-terminal region, from residues 324 to 407. Near the N-terminus, there are two putative tyrosine phosphorylation sites (tyrosine residue at position 84 and 111) and several PXXP sites (putative SH3 binding sites). The other two cDNA clones (clones #7 and #12) were found to encode polypeptides of 428 and 353 amino acids due to differential splicing at the 5'-end of the sequence (FIGS. 6A-6B and 9A-9B) and are different splice variants provided by the present invention.

Example 2

Binding Studies with MIST Protein

In this Example, experiments were performed to determine if human MIST provided by the present invention associated with signaling proteins critical for cell activation. For this purpose, cell lysates from unstimulated Jurkat T cells, or TCR/CD3-activated Jurkat T cells, were prepared and precipitated with TALON® resin beads (Clontech, Palo Alto, Calif.) preloaded with equivalent amounts (5 □g total) of His-MIST fusion proteins. The phosphotyrosine content of precipitated proteins was analyzed by SDS-PAGE followed by Western blotting with an anti-phosphotyrosine specific antibody (4G10, UBI, Hauppague, N.Y.).

More specifically, Jurkat T cells ($10^7$/lane) were unstimulated, or were stimulated with monoclonal antibody (MoAb) to the T-cell receptor TCR/CD3 (G19-4-BMS) for 5 minutes at 37° C., and then lysed in 1% NP40-containing lysis buffer and incubated with TALON® beads preloaded with equivalent amounts (50 □l of slurry resin) of the indicated His-MIST fusion proteins. Reactants and immunoprecipitates were subjected to SDS-PAGE on 4-20% gradient gels. Immunoblotting was performed with anti-phosphotyrosine MoAb 4G10. Blot stripping was performed and the membrane was subsequently re-probed with anti-Grb2 MoAb (Santa Cruz Biotechnology, Inc., Santa Cruz, Calif.), anti-Cbl MoAb (Santa Cruz Biotechnology, Inc., Santa Cruz, Calif.), or anti-Vav1 MoAb (Upstate Biotechnology, Inc., Lake Placid, N.Y.).

Figure 12:
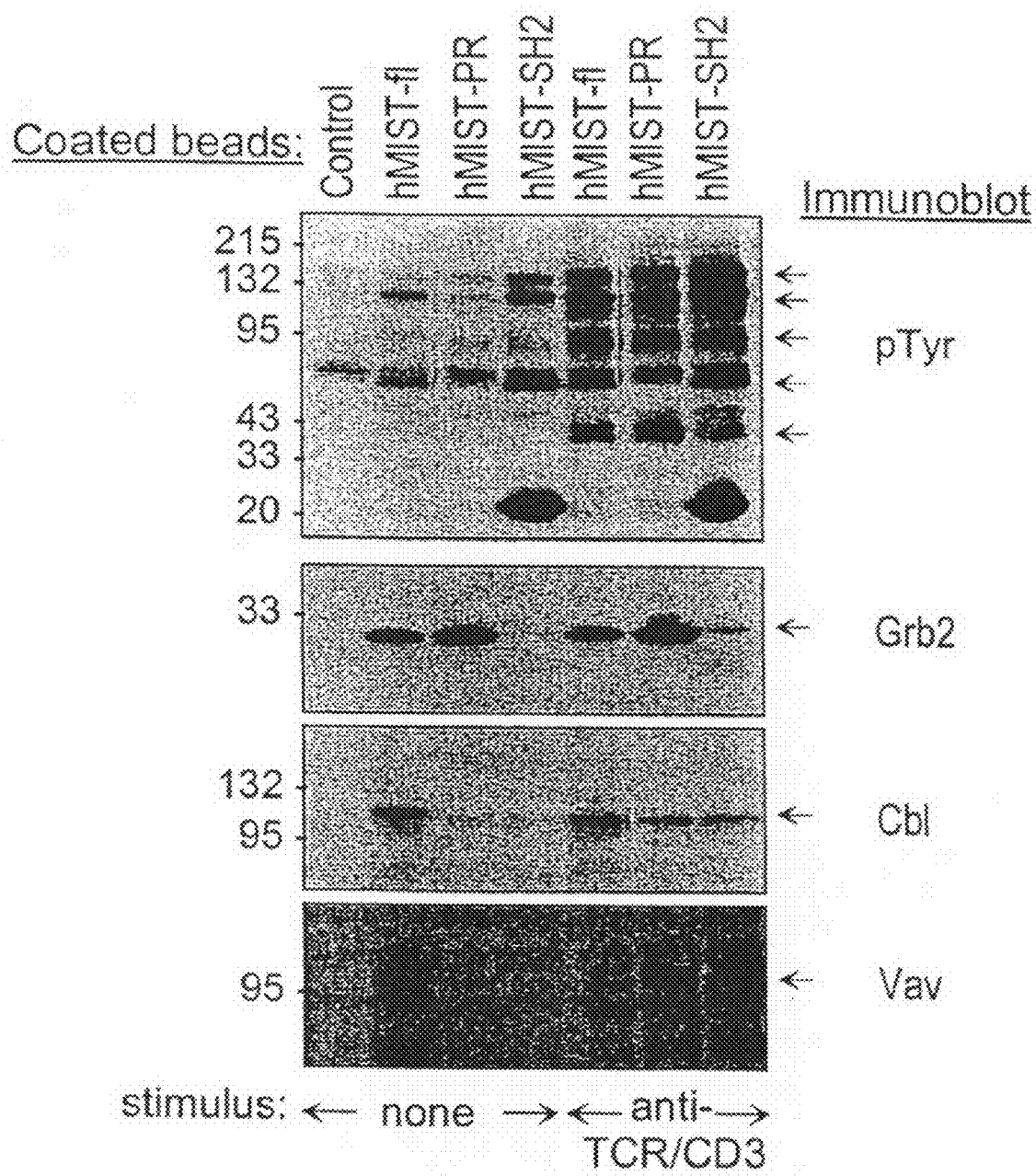
FIG. 12 shows the results of immunoblotting analyses using the recombinant MIST proteins as described above for FIG. 11 and in Example 2.

As shown in FIG. 12, (upper panel), at least two tyrosine phosphorylated proteins (MW: 116- and 55-kDa) co-precipitated with the His-MIST-fl and His-MIST-SH2 fusion proteins prior to cell activation. However, after 5 minutes of anti-TCR/CD3 mediated stimulation of the cells, numerous tyrosine phosphorylated proteins (i.e., proteins having MW: 140-, 116-, 95-, 55- and 38-kDa) were detected upon co-precipitation with the panel of MIST fusion proteins.

Figure 13:
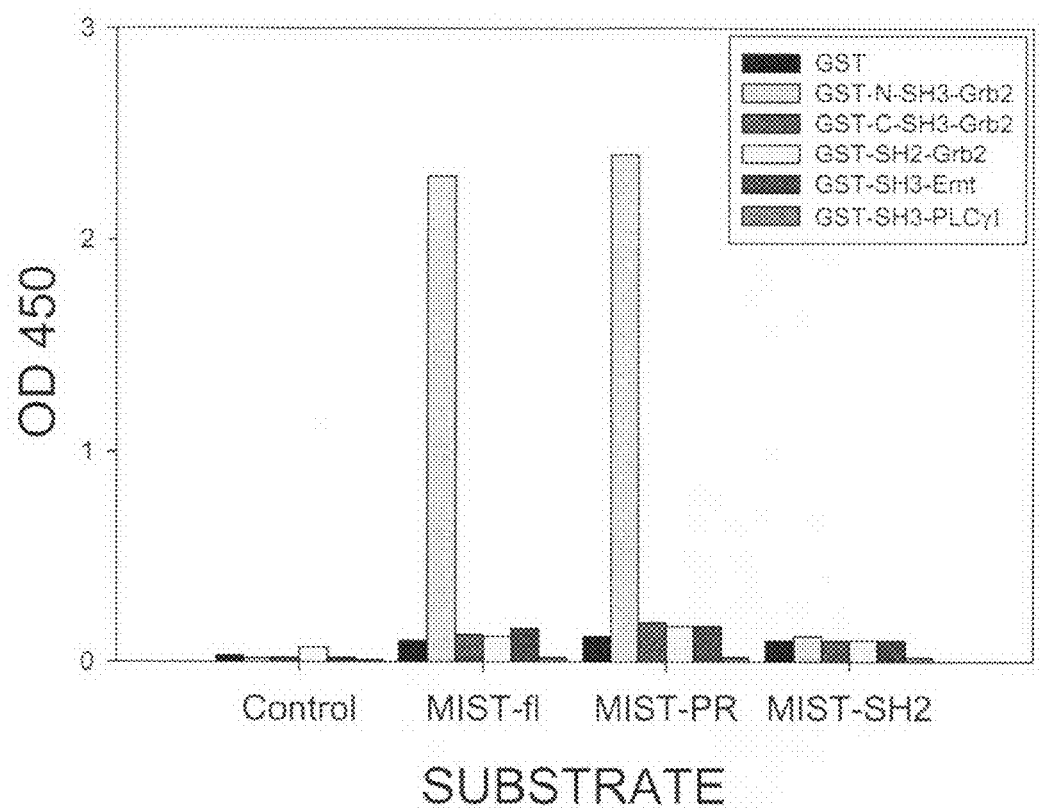
FIG. 13 presents the results of in vitro analysis of the interaction of MIST and Grb2, as further described in Example 2. The data shown are representative means of quadruplicate samples.

In an attempt to identify the tyrosine phosphorylated proteins associated to MIST, the same membrane was stripped and re-probed with different monoclonal antibodies specific for known signaling proteins. The adapter protein Grb2 was found to co-precipitate with the His-MIST-fl and His-MIST-PR protein products, but not with the His-MIST-SH2 fusion protein, under both unstimulated or TCR/CD3-activated conditions (FIG. 12). In addition, other important signaling proteins, namely, Vav, LAT and c-Cbl, were identified in association with the MIST fusion proteins Furthermore, the MIST/Grb2 association was specifically mediated by the MIST proline-rich motif and the N-terminal SH3 domain of Grb2. This was demonstrated using a recombinant N-terminal SH3 domain of Grb2 and the His-MIST-PR protein in an ELISA format (FIG. 13).

Specifically, for the ELISA, substrate proteins (Control, His-MIST-fl, His-MIST-PR and His-MIST-SH2) at 4 µg/ml were placed into standard 96-well ELISA plates in 50 mM NaHCO₃, pH 9, overnight at 4° C. Wells were blocked for 1 hour with 5% non-fat milk in PBS+0.05% Tween 20 (PBS-T) and then were washed 3 times with PBS-T. Next, GST alone, or the indicated GST-SH3 or -SH2 fusion proteins, and 5 µg/ml horse radish peroxidase (HRP) in blocking buffer were added to the wells for one hour. Wells were then washed three times with PBS-T. GST bound proteins were detected using an anti-GST rabbit specific antiserum, followed by anti-rabbit Ig-HRP conjugated antiserum. Reactions were developed using the Kirkegaard & Perry Laboratory TMB ELISA kit (100 µl/well of 50:50 mix TMB substrate and H₂O₂ solutions). Color reactions were stopped with 100 µl/well 1 N H₂SO₄, and the absorbance was measured at 450 nm-650 nm. Interestingly, there was no detectable binding of the His-MIST fusion protein to either the Emt domain (i.e., tyrosine kinase SH3 domain) or the PLC-yl SH3 domain, indicating specificity for the N-terminal Grb2 SH3 domain.

Additional studies were undertaken to compare the binding of human MIST SH2-Ig with that of other SH2-Ig fusion proteins for binding to a phosphopeptide derived from the sequence of human SLP-76 (DDpYESPND), (SEQ ID NO:7), in standard amino acid code where pY=phosphotyrosine). As shown in FIG. 14, binding of hMIST-SH2-Ig to the phosphopeptide was detectable, but bound with less affinity than the SH2-Ig from the Vav guanine nucleotide exchange factor (GEF). In contrast, the SH2 fusion protein derived from SLP-76 did not bind to the phosphopeptide. Similar results were obtained using a phosphopeptide derived from the sequence of human Src-like adapter protein (SLAP).

Example 3

Labeling of Hybridization Probes and Use Thereof

Hybridization probes derived from SEQ ID NO:1 are employed to screen cDNAs, genomic DNAs, or mRNAs. Although the labeling of oligonucleotides containing about 20 base pairs is described in this Example, essentially the same procedure is used with larger cDNA fragments. Oligonucleotides are designed using state-of-the-art software such as OLIGO 4.06 (National Biosciences), labeled by combining 50 pmol of each oligomer and 250 µCi of [$\gamma$-$^{32}$P] adenosine triphosphate (Amersham) and T4 polynucleotide kinase (DuPont NEN, Boston, Mass.). The labeled oligonucleotides are substantially purified with SEPHADEX® G-25 superfine resin column (Amersham Pharmacia Biotech). A portion containing $10^7$ counts per minute of each of the sense and antisense oligonucleotides is used in a typical membrane based hybridization analysis of human genomic DNA digested with one of the following endonucleases (e.g., Ase I, Bgl II, Eco RI, Pst I, Xba 1, or Pvu II, DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMATAR film (Kodak, Rochester, N.Y.) is exposed to the blots in a Phosphoimager cassette (Molecular Dynamics, Sunnyvale, Calif.) for several hours, hybridization patterns are compared visually.

Example 4

Complementary Polynucleotides

Antisense molecules or nucleic acid sequence complementary to the MIST protein-encoding sequence, or any part thereof, is used to decrease or to inhibit the expression of naturally occurring MIST. Although the use of antisense or complementary oligonucleotides comprising about 15 to 35 base-pairs is described, essentially the same procedure is used with smaller or larger nucleic acid sequence fragments. An oligonucleotide based on the coding sequence of MIST protein, as shown in FIGS. 2 and 3A-3B, is used to inhibit expression of naturally occurring MIST. The complementary oligonucleotide is designed from the most unique 5' sequence (FIGS. 1A-1B and 3A-3B), and is used either to inhibit transcription by preventing promoter binding to the coding sequence, or to inhibit translation by preventing the ribosome from binding to the MIST protein-encoding transcript.

Using an appropriate portion of the signal and 5' sequence of SEQ ID NO:1, an effective antisense oligonucleotide includes any of about 15-35 nucleotides spanning the region which translates into the signal or 5' coding sequence of the polypeptide as shown in FIGS. 2 and 3A-3B. Appropriate oligonucleotides are designed using OLIGO 4.06 software and the MIST protein coding sequence (SEQ ID NO:1).

Example 5

Northern Analysis

Northern analysis is used to detect the presence of a transcript of a gene and involves the hybridization of a labeled nucleotide sequence to a membrane on which RNA from a particular cell or tissue type has been bound (See, J. Sambrook et al., supra). Analogous computer techniques using BLAST® (S. F. Altschul, 1993, *J. Mol. Evol.*, 36:290-300 and S. F. Altschul et al., 1990, *J. Mol. Evol.*, 215:403-410) are used to search for identical or related molecules in nucleotide databases, such as GENBANK® or the LIFESEQ database (Incyte Pharmaceuticals). This analysis is much more rapid and less labor-intensive than performing multiple, membrane-based hybridizations. In addition, the sensitivity of the computer search can be modified to determine whether any particular match is categorized as being exact (identical) or homologous.

The basis of the search is the product score, which is defined as follows: (% sequence identity×maximum BLAST score)/100.

The product score takes into account both the degree of similarity between two sequences and the length of the sequence match. For example, with a product score of 40, the match will be exact within a 1-2% error; at 70, the match will be exact. Homologous molecules are usually identified by selecting those which show product scores between 15 and 40, although lower scores may identify related molecules. The results of Northern analysis are reported as a list of libraries in which the transcript encoding MIST occurs. Abundance and percent abundance are also reported. Abundance directly reflects the number of times that a particular transcript is represented in a cDNA library, and percent abundance is abundance divided by the total number of sequences that are examined in the cDNA library.

Example 6

Microarrays

For the production of oligonucleotides for a microarray, SEQ ID NO:1 (or SEQ ID NO:3 or 5) is examined using a computer algorithm which starts at the 3' end of the nucleotide sequence. The algorithm identifies oligomers of defined length that are unique to the gene, have a GC content within a range that is suitable for hybridization and lack predicted secondary structure that would interfere with hybridization. The algorithm identifies specific oligonucleotides of 20 nucleotides in length, i.e., 20-mers. A matched set of oligonucleotides is created in which one nucleotide in the center of each sequence is altered. This process is repeated for each gene in the microarray, and double sets of 20-mers are synthesized in the presence of fluorescent or radioactive nucleotides and arranged on the surface of a substrate. When the substrate is a silicon chip, a light-directed chemical process is used for deposition (WO 95/11995, M. Chee et al.).

Alternatively, a chemical coupling procedure and an ink jet device is used to synthesize oligomers on the surface of a substrate. (WO 95/25116, J. D. Baldeschweiler et al.). As another alternative, a "gridded" array that is analogous to a dot (or slot) blot is used to arrange and link cDNA fragments or oligonucleotides to the surface of a substrate using, for example, a vacuum system, or thermal, UV, mechanical, or chemical bonding techniques. A typical array may be produced by hand, or by using available materials and equipment, and may contain grids of 8 dots, 24 dots, 96 dots, 384 dots, 1536 dots, or 6144 dots. After hybridization, the microarray is washed to remove any non-hybridized probe, and a detection device is used to determine the levels and patterns of radioactivity or fluorescence. The detection device may be as simple as X-ray film, or as complicated as a light scanning apparatus. Scanned fluorescent images are examined to determine degree of complementarity and the relative abundance/expression level of each oligonucleotide sequence in the microarray.

Example 7

Purification of Naturally Occurring MIST Protein Using Specific Antibodies

Naturally occurring or recombinant MIST polypeptide is substantially purified by immunoaffinity chromatography using antibodies specific for the MIST polypeptide, or a peptide derived therefrom. An immunoaffinity column is constructed by covalently coupling anti-MIST polypeptide antibody to an activated chromatographic resin, such as CNBr-activated SEPHAROSE® (Amersham Pharmacia Biotech). After the coupling, the resin is blocked and washed according to the manufacturer's instructions.

Medium containing MIST polypeptide is passed over the immunoaffinity column, and the column is washed under conditions that allow the preferential absorbance of the MIST polypeptide (e.g., high ionic strength buffers in the presence of detergent). The column is eluted under conditions that disrupt antibody/MIST polypeptide binding (e.g., a buffer of pH 2-3, or a high concentration of a chaotrope, such as urea or thiocyanate ion), and MIST polypeptide is collected.

Example 8

Identification of Molecules that Interact with the MIST Protein

MIST polypeptide, or biologically active fragments thereof, are labeled with $^{125}$I Bolton-Hunter reagent (Bolton et al., 1973, *Biochem. J.*, 133:529). Candidate molecules previously arrayed in wells of a multi-welled plate are incubated with the labeled MIST polypeptide, washed, and any wells having labeled MIST polypeptide-candidate molecule complexes are assayed. Data obtained using different concentrations of the MIST polypeptide are used to calculate values for the number, affinity and association of the MIST polypeptide with the candidate molecules.

Example 9

Production of Recombinant MIST linked to a His Tag

For His tags, the initial expression vector used for human MIST (hMIST) proteins was pFasBac (Life Technologies, MD), (D. Polayes et al., 1996, *Focus*, 18:10) containing hMIST (fl, 1/320, PR, SH2) transformed into MAX Efficiency DH10Bac cells containing bacmid and helper. The colonies with recombinant Bacmid were cultured overnight and the recombinant Bacmid DNA was isolated and transfected into insect cells (Sf9) using CELLFECTIN® reagent (Life Technologies, MD). Recombinant baculovirus was produced and used for further Sf9 cell infection and production of the recombinant proteins. This rapid and efficient method was used to generate recombinant baculovirus, as described by V. A. Luckow et al., 1996, *J. Virol.*, 67:4566. When the gene of interest is cloned into a pFastBac expression vector, the expressed protein contains 6 tandem histidines (6×His) as the "affinity tag" at its amino terminus. The tag is small and is uncharged at physiological pH. It also rarely interferes with protein structure and function. The 6×His affinity tag has a strong affinity for Ni-NTA resin (E. Hochuli et al., 1987, *J. Chromatography*, 411:177), thereby allowing the desired protein to be purified and easily detected.

Example 10

Method of Creating N- and C-Terminal Deletion Mutants Corresponding to MIST Polypeptides of the Present Invention As described elsewhere herein, the present invention encompasses the creation of N- and C-terminal deletion mutants, in addition to any combination of N- and C-terminal deletions thereof, corresponding to the MIST polypeptide of the present invention. A number of methods are available to one skilled in the art for creating such mutants. Such methods include a combination of PCR amplification and gene cloning methodology. Although one of skill in the art of molecular biology, through the use of the teachings provided or referenced herein, and/or otherwise known in the art as standard methods, could readily create each deletion mutants of the present invention, exemplary methods are described below.

Briefly, using the isolated cDNA clone encoding the full-length MIST polypeptide sequence, or splice variant sequences, appropriate primers of about 15-25 nucleotides derived from the desired 5' and 3' positions of SEQ ID NO:1 (or SEQ ID NOs:3 or 5) may be designed to PCR amplify, and subsequently clone, the intended N- and/or C-terminal deletion mutant. Such primers can comprise, for example, an initiation and stop codon for the 5' and 3' primer, respectively. Such primers can also comprise restriction sites to facilitate cloning of the deletion mutant post-amplification. Moreover, the primers may comprise additional sequences, such as, for example, flag-tag sequences, kozac sequences, or other sequences discussed and/or referenced herein.

For example, in the case of the D83 to L443 N-terminal deletion mutant, the following primers presented in Table 3 can be used to amplify a cDNA fragment corresponding to this deletion mutant:

TABLE 3

```
5' Primer  5'-gcagca gcggccgc gactatgatgaccctgagcttcgg -3',   (SEQ ID NO: 49)
           where the underlined sequence represents the NotI
           restriction enzyme site.

3' Primer  5'-gcagca gtcgac cagaggcaagaggtgtctggtgag -3',     (SEQ ID NO: 50)
           where the underlined sequence represents the SalI
           restriction enzyme site.
```

In addition, in the case of the M1 to E323 C-terminal deletion mutant, for example, the following primers presented in Table 4 can be used to amplify a cDNA fragment corresponding to this deletion mutant:

TABLE 4

```
5' Primer  5'- gcagca gcggccgc atggctgaattgaagatccctc 3',     (SEQ ID NO: 51)
           where the underlined sequence represents the NotI
           restriction enzyme site.

3' Primer  5'- gcagca gtcgac ttcattgtgctggacatcctttct -3',    (SEQ ID NO: 52)
           where the underlined sequence represents the SalI
           restriction enzyme site.
```

Such deletions may be useful as decoy receptors for downstream and/or upstream effectors of the MIST polypeptide.

Representative PCR amplification conditions are provided below, although the skilled artisan will appreciate that other conditions may be required for efficient amplification. A 100 µl PCR reaction mixture may be prepared using 10 ng of the template DNA (cDNA clone of MIST), 200 µM 4dNTPs, 1 µM primers, 0.25 U Taq DNA polymerase (PE), and standard Taq DNA polymerase buffer. Typical PCR cycling condition are as follows:

| 20-25 cycles: | 45 sec, 93 degrees |
|               | 2 min, 50 degrees |
|               | 2 min, 72 degrees |
| 1 cycle:      | 10 min, 72 degrees |

After the final extension step of PCR, 5 U Klenow Fragment may be added and incubated for 15 minutes at 30 degrees.

Upon digestion of the fragment with the NotI and SalI restriction enzymes, the fragment can be cloned into an appropriate expression and/or cloning vector which has been similarly digested (e.g., pSport1, among others). The skilled artisan will appreciate that other plasmids can be equally substituted, and may be desirable in certain circumstances. The digested fragment and vector are then ligated using a DNA ligase, and then used to transform competent *E. coli* cells, using methods provided herein and/or as otherwise known in the art.

The 5' primer sequence for amplifying any additional N-terminal deletion mutants may be determined by reference to the following formula:

(S+(X*3)) to ((S+(X*3))+25), wherein 'S' is equal to the nucleotide position of the initiating start codon of the MIST gene (SEQ ID NO:1, or SEQ ID NOS: 3 or 5), and 'X' is equal to the most N-terminal amino acid of the intended N-terminal deletion mutant. The first term provides the start 5' nucleotide position of the 5' primer, while the second term provides the end 3' nucleotide position of the 5' primer corresponding to sense strand of SEQ ID NO:1, or SEQ ID NOS: 3 or 5). Once the corresponding nucleotide positions of the primer are determined, the final nucleotide sequence can be created by the addition of applicable restriction site sequences to the 5' end of the sequence, for example. As described herein, the addition of other sequences to the 5' primer may be desired in certain circumstances (e.g., kozac sequences, etc.). The 3' primer sequence for amplifying any additional N-terminal deletion mutants can be determined by reference to the following formula:

(S+(X*3)) to ((S+(X*3))−25), wherein 'S' is equal to the nucleotide position of the initiating start codon of the MIST gene (SEQ ID NO:1, or SEQ ID NOS: 3 or 5), and 'X' is equal to the most C-terminal amino acid of the intended N-terminal deletion mutant. The first term provides the start 5' nucleotide position of the 3' primer, while the second term provides the end 3' nucleotide position of the 3' primer corresponding to the antisense strand of SEQ ID NO:1, (or SEQ ID NOS: 3 or 5). Once the corresponding nucleotide positions of the primer are determined, the final nucleotide sequence can be created by the addition of applicable restriction site sequences to the 5' end of the sequence, for example. As described herein, the addition of other sequences to the 3' primer may be desired in certain circumstances (e.g., stop codon sequences, etc.). The skilled artisan will appreciate that modifications to the above nucleotide positions may be necessary for optimizing PCR amplification.

The same general formulas provided above can be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan will appreciate that modifications of the above nucleotide positions may be necessary for optimizing PCR amplification.

Preferably, the following N-terminal MIST deletion polypeptides of SEQ ID NO:2 are encompassed by the present invention: M1-L443, A2-L443, E3-L443, L4-L443, K5-L443, I6-L443, P7-L443, L8-L443, T9-L443, R10-L443, Q11-L443, V12-L443, P13-L443, R14-L443, T15-L443, M16-L443, N17-L443, R18-L443, Q19-L443, G20-L443, N21-L443, R22-L443, K23-L443, T24-L443, T25-L443, K26-L443, E27-L443, G28-L443, S29-L443, N30-L443, D31-L443, L32-L443, K33-L443, F34-L443, Q35-L443, N36-L443, F37-L443, S38-L443, L39-L443, P40-L443, K41-L443, N42-L443, R43-L443, S44-L443, W45-L443, P46-L443, R47-L443, I48-L443, N49-L443, S50-L443, A51-L443, T52-L443, G53-L443, Q54-L443, Y55-L443, Q56-L443, R57-L443, M58-L443, N59-L443, K60-L443, P61-L443, L62-L443, L63-L443, D64-L443, W65-L443, E66-L443, R67-L443, N68-L443, F69-L443, A70-L443, A71-L443, V72-L443, L73-L443, D74-L443, G75-L443, A76-L443, K77-L443, G78-L443, H79-L443, S80-L443, D81-L443, D82-L443, D83-L443, Y84-L443, D85-L443, D86-L443, P87-L443, E88-L443, L89-L443, R90-L443, M91-L443, E92-L443, E93-L443, T94-L443, W95-L443, Q96-L443, S97-L443, I98-L443, K99-L443, I100-L443, L101-L443, P102-L443, A103-L443, R104-L443, P105-L443, I106-L443, K107-L443, E108-L443, S109-L443, E110-L443, Y111-L443, A112-L443, D113-L443, T114-L443, H115-L443, Y116-L443, F117-L443, K118-L443, V119-L443, A120-L443, M121-L443, D122-L443, T123-L443, P124-L443, L125-L443, P126-L443, L127-L443, D128-L443, T129-L443, R130-L443, T131-L443, S132-L443, I133-L443, S134-L443, I135-L443, G136-L443, Q137-L443, P138-L443, T139-L443, W140-L443, N141-L443, T142-L443, Q143-L443, T144-L443, R145-L443, L146-L443, E147-L443, R148-L443, V149-L443, D150-L443, K151-L443, P152-L443, I153-L443, S154-L443, K155-L443, D156-L443, V157-L443, R158-L443, S159-L443, Q160-L443, N161-L443, I162-L443, K163-L443, G164-L443, D165-L443, A166-L443, S167-L443, V168-L443, R169-L443, K170-L443, N171-L443, K172-L443, I173-L443, P174-L443, L175-L443, P176-L443, P177-L443, P178-L443, R179-L443, P180-L443, L181-L443, I182-L443, T183-L443, L184-L443, P185-L443, K186-L443, K187-L443, Y188-L443, Q189-L443, P190-L443, L191-L443, P192-L443, P193-L443, E194-L443, P195-L443, E196-L443, S197-L443, S198-L443, R199-L443, P200-L443, P201-L443, L202-L443, S203-L443, Q204-L443, R205-L443, H206-L443, T207-L443, F208-L443, P209-L443, E210-L443, V211-L443, Q212-L443, R213-L443, M214-L443, P215-L443, S216-L443, Q217-L443, I218-L443, S219-L443, L220-L443, R221-L443, D222-L443, L223-L443, S224-L443, E225-L443, V226-L443, L227-L443, E228-L443, A229-L443, E230-L443, K231-L443, V232-L443, P233-L443, H234-L443, N235-L443, Q236-L443, R237-L443, K238-L443, P239-L443, E240-L443, S241-L443, T242-L443, H243-L443, L244-L443, L245-L443, E246-L443, N247-L443, Q248-L443, N249-L443, T250-L443, Q251-L443, E252-L443, I253-L443, P254-L443, L255-L443, A256-L443, I257-L443, S258-L443, S259-L443, S260-L443, S261-L443, F262-L443, T263-L443, T264-L443, S265-L443, N266-L443, H267-L443, S268-L443, V269-L443, Q270-L443, N271-L443, R272-L443, D273-L443, H274-L443, R275-L443, G276-L443, G277-L443, M278-L443, Q279-L443, P280-L443, C281-L443, S282-L443, P283-L443, Q284-L443, R285-L443, C286-L443, Q287-L443, P288-L443, P289-L443, A290-L443, S291-L443, C292-L443, S293-L443, P294-L443, H295-L443, E296-L443, N297-L443, I298-L443, L299-L443, P300-L443, Y301-L443, K302-L443, Y303-L443, T304-L443, S305-L443, W306-L443, R307-L443, P308-L443, P309-L443, F310-L443, P311-L443, K312-L443, R313-L443, S314-L443, D315-L443, R316-L443, K317-L443, D318-L443, V319-L443, Q320-L443, H321-L443, N322-L443, E323-L443, W324-L443, Y325-L443, I326-L443, G327-L443, E328-L443, Y329-L443, S330-L443, R331-L443, Q332-L443, A333-L443, V334-L443, E335-L443, E336-L443, A337-L443, F338-L443, M339-L443, K340-L443, E341-L443, N342-L443, K343-L443, D344-L443, G345-L443, S346-L443, F347-L443, L348-L443, V349-L443, R350-L443, D351-L443, C352-L443, S353-L443, T354-L443, K355-L443, S356-L443, K357-L443, E358-L443, E359-L443, P360-L443, Y361-L443, V362-L443, L363-L443, A364-L443, V365-L443, F366-L443, Y367-L443, E368-L443, N369-L443, K370-L443, V371-L443, Y372-L443, N373-L443, V374-L443, K375-L443, I376-L443, R377-L443, F378-L443, L379-L443, E380-L443, R381-L443, N382-L443, Q383-L443, Q384-L443, F385-L443, A386-L443, L387-L443, G388-L443, T389-L443, G390-L443, L391-L443, R392-L443, G393-L443, D394-L443, E395-L443, K396-L443, F397-L443, D398-L443, S399-L443, V400-L443, E401-L443, D402-L443, I403-L443, I404-L443, E405-L443, H406-L443, Y407-L443, K408-L443, N409-L443, F410-L443, P411-L443, I412-L443, I413-L443, L414-L443, I415-L443, D416-L443, G417-L443, K418-L443, D419-L443, K420-L443, T421-L443, G422-L443, V423-L443, H424-L443, R425-L443, K426-L443, Q427-L443, C428-L443, H429-L443, L430-L443, T431-L443, Q432-L443, P433-L443, L434-L443, P435-L443, L436-L443, and/or T437-L443 (of SEQ ID NO:2). Polynucleotide sequences encoding these polypeptides are also provided. These N-terminal MIST deletion polypeptides can be employed as immunogenic and/or antigenic epitopes as described elsewhere herein.

Also, preferably, the following C-terminal MIST deletion polypeptides of SEQ ID NO:2 are encompassed by the present invention: M1-L443, M1-P442, M1-L441, M1-L440, M1-H439, M1-R438, M1-T437, M1-L436, M1-P435, M1-L434, M1-P433, M1-Q432, M1-T431, M1-L430, M1-H429, M1-C428, M1-Q427, M1-K426, M1-R425, M1-H424, M1-V423, M1-G422, M1-T421, M1-K420, M1-D419, M1-K418, M1-G417, M1-D416, M1-I415, M1-L414, M1-I413, M1-I412, M1-P411, M1-F410, M1-N409, M1-K408, M1-Y407, M1-H406, M1-E405, M1-I404, M1-I403, M1-D402, M1-E401, M1-V400, M1-S399, M1-D398, M1-F397, M1-K396, M1-E395, M1-D394, M1-G393, M1-R392, M1-L391, M1-G390, M1-T389, M1-G388, M1-L387, M1-A386, M1-F385, M1-Q384, M1-Q383, M1-N382, M1-R381, M1-E380, M1-L379, M1-F378, M1-R377, M1-I376, M1-K375, M1-V374, M1-N373, M1-Y372, M1-V371, M1-K370, M1-N369, M1-E368, M1-Y367, M1-F366, M1-V365, M1-A364, M1-L363, M1-V362, M1-Y361, M1-P360, M1-E359, M1-E358, M1-K357, M1-S356, M1-K355, M1-T354, M1-S353, M1-C352, M1-D351, M1-R350, M1-V349, M1-L348, M1-F347, M1-S346, M1-G345, M1-D344, M1-K343, M1-N342, M1-E341, M1-K340, M1-M339, M1-F338, M1-A337, M1-E336, M1-E335, M1-V334, M1-A333, M1-Q332, M1-R331, M1-S330, M1-Y329, M1-E328, M1-G327, M1-I326, M1-Y325, M1-W324, M1-E323, M1-N322, M1-H321, M1-Q320, M1-V319, M1-D318, M1-K317, M1-R316, M1-D315, M1-S314, M1-R313, M1-K312, M1-P311, M1-F310, M1-P309, M1-P308, M1-R307, M1-W306, M1-S305, M1-T304, M1-Y303, M1-K302, M1-Y301, M1-P300, M1-L299, M1-I298, M1-N297, M1-E296, M1-H295, M1-P294, M1-S293, M1-C292, M1-S291, M1-A290, M1-P289, M1-P288, M1-Q287, M1-C286, M1-R285, M1-Q284, M1-P283, M1-S282, M1-C281, M1-P280, M1-Q279, M1-M278, M1-G277, M1-G276, M1-R275, M1-H274, M1-D273, M1-R272, M1-N271, M1-Q270, M1-V269, M1-S268, M1-H267, M1-N266, M1-S265, M1-T264, M1-T263, M1-F262, M1-S261, M1-S260, M1-S259, M1-S258, M1-I257, M1-A256, M1-L255, M1-P254, M1-I253, M1-E252, M1-Q251, M1-T250, M1-N249, M1-Q248, M1-N247, M1-E246, M1-L245, M1-L244, M1-H243, M1-T242, M1-S241, M1-E240, M1-P239, M1-K238, M1-R237, M1-Q236, M1-N235, M1-H234, M1-P233, M1-V232, M1-K231, M1-E230, M1-A229, M1-E228, M1-L227, M1-V226, M1-E225, M1-S224, M1-L223, M1-D222, M1-R221, M1-L220, M1-S219, M1-I218, M1-Q217, M1-S216, M1-P215, M1-M214, M1-R213, M1-Q212, M1-V211, M1-E210, M1-P209, M1-F208, M1-T207, M1-H206, M1-R205, M1-Q204, M1-S203, M1-L202, M1-P201, M1-P200, M1-R199, M1-S198, M1-S197, M1-E196, M1-P195, M1-E194, M1-P193, M1-P192, M1-L191, M1-P190, M1-Q189, M1-Y188, M1-K187, M1-K186, M1-P185, M1-L184, M1-T183, M1-I182, M1-L181, M1-P180, M1-R179, M1-P178, M1-P177, M1-P176, M1-L175, M1-P174, M1-I173, M1-K172, M1-N171, M1-K170, M1-R169, M1-V168, M1-S167, M1-A166, M1-D165, M1-G164, M1-K163, M1-I162, M1-N161, M1-Q160, M1-S159, M1-R158, M1-V157, M1-D156, M1-K155, M1-S154, M1-I153, M1-P152, M1-K151, M1-D150, M1-V149, M1-R148, M1-E147, M1-L146, M1-R145, M1-T144, M1-Q143, M1-T142, M1-N141, M1-W140, M1-T139, M1-P138, M1-Q137, M1-G136, M1-I135, M1-S134, M1-I133, M1-S132, M1-T131, M1-R130, M1-T129, M1-D128, M1-L127, M1-P126, M1-L125, M1-P124, M1-T123, M1-D122, M1-M121, M1-A120, M1-V119, M1-K118, M1-F117, M1-Y116, M1-H115, M1-T114, M1-D113, M1-A112, M1-Y111, M1-E110, M1-S109, M1-E108, M1-K107, M1-I106, M1-P105, M1-R104, M1-A103, M1-P102, M1-L101, M1-I100, M1-K99, M1-I98, M1-S97, M1-Q96, M1-W95, M1-T94, M1-E93, M1-E92, M1-M91, M1-R90, M1-L89, M1-E88, M1-P87, M1-D86, M1-D85, M1-Y84, M1-D83, M1-D82, M1-D81, M1-S80, M1-H79, M1-G78, M1-K77, M1-A76, M1-G75, M1-D74, M1-L73, M1-V72, M1-A71, M1-A70, M1-F69, M1-N68, M1-R67, M1-E66, M1-W65, M1-D64, M1-L63, M1-L62, M1-P61, M1-K60, M1-N59, M1-M58, M1-R57, M1-Q56, M1-Y55, M1-Q54, M1-G53, M1-T52, M1-A51, M1-S50, M1-N49, M1-I48, M1-R47, M1-P46, M1-W45, M1-S44, M1-R43, M1-N42, M1-K41, M1-P40, M1-L39, M1-S38, M1-F37, M1-N36, M1-Q35, M1-F34, M1-K33, M1-L32, M1-D31, M1-N30, M1-S29, M1-G28, M1-E27, M1-K26, M1-T25, M1-T24, M1-K23, M1-R22, M1-N21, M1-G20, M1-Q19, M1-R18, M1-N17, M1-M16, M1-T15, M1-R14, M1-P13, M1-V12, M1-Q11, M1-R10, M1-T9, M1-L8, and/or M1-P7 (of SEQ ID NO:2). Polynucleotide sequences encoding these polypeptides are also provided. These C-terminal MIST deletion polypeptides can be used as immunogenic and/or antigenic epitopes as described elsewhere herein.

Alternatively, preferred polypeptides/peptides of the present invention may comprise polypeptide sequences corresponding to, for example, internal regions of the MIST polypeptide (e.g., any combination of both N- and C-terminal MIST polypeptide deletions) of SEQ ID NO:2). For example, internal regions can be defined by the equation: amino acid "NX" to amino acid "CX", where "NX" refers to any N-terminal deletion polypeptide amino acid of MIST (SEQ ID NO:2), and where "CX" refers to any C-terminal deletion polypeptide amino acid of MIST (SEQ ID NO:2). Polynucleotides encoding these polypeptides are also provided. The present invention also encompasses the use of these polypeptides as an immunogenic and/or antigenic epitope as described elsewhere herein.

In a preferred embodiment, the following N-terminal MIST splice variant clone #7 (SEQ ID NO:4) deletion polypeptides are encompassed by the present invention: M1-L428, N2-L428, R3-L428, Q4-L428, G5-L428, N6-L428, R7-L428, K8-L428, T9-L428, T10-L428, K11-L428, E12-L428, G13-L428, S14-L428, N15-L428, D16-L428, L17-L428, K18-L428, F19-L428, Q20-L428, N21-L428, F22-L428, S23-L428, L24-L428, P25-L428, K26-L428, N27-L428, R28-L428, S29-L428, W30-L428, P31-L428, R32-L428, I33-L428, N34-L428, S35-L428, A36-L428, T37-L428, G38-L428, Q39-L428, Y40-L428, Q41-L428, R42-L428, M43-L428, N44-L428, K45-L428, P46-L428, L47-L428, L48-L428, D49-L428, W50-L428, E51-L428, R52-L428, N53-L428, F54-L428, A55-L428, A56-L428, V57-L428, L58-L428, D59-L428, G60-L428, A61-L428, K62-L428, G63-L428, H64-L428, S65-L428, D66-L428, D67-L428, D68-L428, Y69-L428, D70-L428, D71-L428, P72-L428, E73-L428, L74-L428, R75-L428, M76-L428, E77-L428, E78-L428, T79-L428, W80-L428, Q81-L428, S82-L428, I83-L428, K84-L428, I85-L428, L86-L428, P87-L428, A88-L428, R89-L428, P90-L428, I91-L428, K92-L428, E93-L428, S94-L428, E95-L428, Y96-L428, A97-L428, D98-L428, T99-L428, H100-L428, Y101-L428, F102-L428, K103-L428, V104-L428, A105-L428, M106-L428, D107-L428, T108-L428, P109-L428, L110-L428, P111-L428, L112-L428, D113-L428, T114-L428, R115-L428, T1±6-L428, S117-L428, I118-L428, S119-L428, I120-L428, G121-L428, Q122-L428, P123-L428, T124-L428, W125-L428, N126-L428, T127-L428, Q128-L428, T129-L428, R130-L428, L131-L428, E132-L428, R133-L428, V134-L428, D135-L428, K136-L428, P137-L428, I138-L428, S139-L428, K140-L428, D141-L428, V142-L428, R143-L428, S144-L428, Q145-L428, N146-L428, I147-L428, K148-L428, G149-L428, D150-L428, A151-L428, S152-L428, V153-L428, R154-L428, K155-L428, N156-L428, K157-L428, I158-L428, P159-L428, L160-L428, P161-L428, P162-L428, P163-L428, R164-L428, P165-L428, L166-L428, I167-L428, T168-L428, L169-L428, P170-L428, K171-L428, K172-L428, Y173-L428, Q174-L428, P175-L428, L176-L428, P177-L428, P178-L428, E179-L428, P180-L428, E181-L428, S182-L428, S183-L428, R184-L428, P185-L428, P186-L428, L187-L428, S188-L428, Q189-L428, R190-L428, H191-L428, T192-L428, F193-L428, P194-L428, E195-L428, V196-L428, Q197-L428, R198-L428, M199-L428, P200-L428, S201-L428, Q202-L428, I203-L428, S204-L428, L205-L428, R206-L428, D207-L428, L208-L428, S209-L428, E210-L428, V211-L428, L212-L428, E213-L428, A214-L428, E215-L428, K216-L428, V217-L428, P218-L428, H219-L428, N220-L428, Q221-L428, R222-L428, K223-L428, P224-L428, E225-L428, S226-L428, T227-L428, H228-L428, L229-L428, L230-L428, E231-L428, N232-L428, Q233-L428, N234-L428, T235-L428, Q236-L428, E237-L428, I238-L428, P239-L428, L240-L428, A241-L428, I242-L428, S243-L428, S244-L428, S245-L428, S246-L428, F247-L428, T248-L428, T249-L428, S250-L428, N251-L428, H252-L428, S253-L428, V254-L428, Q255-L428, N256-L428, R257-L428, D258-L428, H259-L428, R260-L428, G261-L428, G262-L428, M263-L428, Q264-L428, P265-L428, C266-L428, S267-L428, P268-L428, Q269-L428, R270-L428, C271-L428, Q272-L428, P273-L428, P274-L428, A275-L428, S276-L428, C277-L428, S278-L428, P279-L428, H280-L428, E281-L428, N282-L428, I283-L428, L284-L428, P285-L428, Y286-L428, K287-L428, Y288-L428, T289-L428, S290-L428, W291-L428, R292-L428, P293-L428, P294-L428, F295-L428, P296-L428, K297-L428, R298-L428, S299-L428, D300-L428, R301-L428, K302-L428, D303-L428, V304-L428, Q305-L428, H306-L428, N307-L428, E308-L428, W309-L428, Y310-L428, I311-L428, G312-L428, E313-L428, Y314-L428, S315-L428, R316-L428, Q317-L428, A318-L428, V319-L428, E320-L428, E321-L428, A322-L428, F323-L428, M324-L428, K325-L428, E326-L428, N327-L428, K328-L428, D329-L428, G330-L428, S331-L428, F332-L428, L333-L428, V334-L428, R335-L428, D336-L428, C337-L428, S338-L428, T339-L428, K340-L428, S341-L428, K342-L428, E343-L428, E344-L428, P345-L428, Y346-L428, V347-L428, L348-L428, A349-L428, V350-L428, F351-L428, Y352-L428, E353-L428, N354-L428, K355-L428, V356-L428, Y357-L428, N358-L428, V359-L428, K360-L428, I361-L428, R362-L428, F363-L428, L364-L428, E365-L428, R366-L428, N367-L428, Q368-L428, Q369-L428, F370-L428, A371-L428, L372-L428, G373-L428, T374-L428, G375-L428, L376-L428, R377-L428, G378-L428, D379-L428, E380-L428, K381-L428, F382-L428, D383-L428, S384-L428, V385-L428, E386-L428, D387-L428, I388-L428, I389-L428, E390-L428, H391-L428, Y392-L428, K393-L428, N394-L428, F395-L428, P396-L428, I397-L428, I398-L428, L399-L428, I400-L428, D401-L428, G402-L428, K403-L428, D404-L428, K405-L428, T406-L428, G407-L428, V408-L428, H409-L428, R410-L428, K411-L428, Q412-L428, C413-L428, H414-L428, L415-L428, T416-L428, Q417-L428, P418-L428, L419-L428, P420-L428, L421-L428, and/or T422-L428 (of SEQ ID NO:4). Polynucleotide sequences encoding these polypeptides are also provided. These N-terminal MIST splice variant clone 7 deletion polypeptides are useful as immunogenic and/or antigenic epitopes as described elsewhere herein.

In another preferred embodiment, the following C-terminal MIST splice variant clone 7 (SEQ ID NO:4) deletion polypeptides are encompassed by the present invention: M1-L428, M1-P427, M1-L426, M1-L425, M1-H424, M1-R423, M1-T422, M1-L421, M1-P420, M1-L419, M1-P418, M1-Q417, M1-T416, M1-L415, M1-H414, M1-C413, M1-Q412, M1-K411, M1-R410, M1-H409, M1-V408, M1-G407, M1-T406, M1-K405, M1-D404, M1-K403, M1-G402, M1-D401, M1-I400, M1-L399, M1-I398, M1-I397, M1-P396, M1-F395, M1-N394, M1-K393, M1-Y392, M1-H391, M1-E390, M1-I389, M1-I388, M1-D387, M1-E386, M1-V385, M1-S384, M1-D383, M1-F382, M1-K381, M1-E380, M1-D379, M1-G378, M1-R377, M1-L376, M1-G375, M1-T374, M1-G373, M1-L372, M1-A371, M1-F370, M1-Q369, M1-Q368, M1-N367, M1-R366, M1-E365, M1-L364, M1-F363, M1-R362, M1-I361, M1-K360, M1-V359, M1-N358, M1-Y357, M1-V356, M1-K355, M1-N354, M1-E353, M1-Y352, M1-F351, M1-V350, M1-A349, M1-L348, M1-V347, M1-Y346, M1-P345, M1-E344, M1-E343, M1-K342, M1-S341, M1-K340, M1-T339, M1-S338, M1-C337, M1-D336, M1-R335, M1-V334, M1-L333, M1-F332, M1-S331, M1-G330, M1-D329, M1-K328, M1-N327, M1-E326, M1-K325, M1-M324, M1-F323, M1-A322, M1-E321, M1-E320, M1-V319, M1-A318, M1-Q317, M1-R316, M1-S315, M1-Y314, M1-E313, M1-G312, M1-I311, M1-Y310, M1-W309, M1-E308, M1-N$_3$O$_7$, M1-H306, M1-Q305, M1-V304, M1-D303, M1-K302, M1-R301, M1-D300, M1-S299, M1-R298, M1-K297, M1-P296, M1-F295, M1-P294, M1-P293, M1-R292, M1-W291, M1-S290, M1-T289, M1-Y288, M1-K287, M1-Y286, M1-P285, M1-L284, M1-I283, M1-N282, M1-E281, M1-H280, M1-P279, M1-S278, M1-C277, M1-S276, M1-A275, M1-P274, M1-P273, M1-Q272, M1-C271, M1-R270, M1-Q269, M1-P268, M1-S267, M1-C266, M1-P265, M1-Q264, M1-M263, M1-G262, M1-G261, M1-R260, M1-H259, M1-D258, M1-R257, M1-N256, M1-Q255, M1-V254, M1-S253, M1-H252, M1-N251, M1-S250, M1-T249, M1-T248, M1-F247, M1-S246, M1-S245, M1-S244, M1-S243, M1-I242, M1-A241, M1-L240, M1-P239, M1-I238, M1-E237, M1-Q236, M1-T235, M1-N234, M1-Q233, M1-N232, M1-E231, M1-L230, M1-L229, M1-H228, M1-T227, M1-S226, M1-E225, M1-P224, M1-K223, M1-R222, M1-Q221, M1-N220, M1-H219, M1-P218, M1-V217, M1-K216, M1-E215, M1-A214, M1-E213, M1-L212, M1-V211, M1-E210, M1-S209, M1-L208, M1-D207, M1-R206, M1-L205, M1-S204, M1-I203, M1-Q202, M1-S201, M1-P200, M1-M199, M1-R198, M1-Q197, M1-V196, M1-E195, M1-P194, M1-F193, M1-T192, M1-H191, M1-R190, M1-Q189, M1-S188, M1-L187, M1-P186, M1-P185, M1-R184, M1-S183, M1-S182, M1-E181, M1-P180, M1-E179, M1-P178, M1-P177, M1-L176, M1-P175, M1-Q174, M1-Y173, M1-K172, M1-K171, M1-P170, M1-L169, M1-T168, M1-I167, M1-L166, M1-P165, M1-R164, M1-P163, M1-P162, M1-P161, M1-L160, M1-P159, M1-I158, M1-K157, M1-N156, M1-K155, M1-R154, M1-V153, M1-S152, M1-A151, M1-D150, M1-G149, M1-K148, M1-I147, M1-N146, M1-Q145, M1-S144, M1-R143, M1-V142, M1-D141, M1-K140, M1-S139, M1-I138, M1-P137, M1-K136, M1-D135, M1-V134, M1-R133, M1-E132, M1-L131, M1-R130, M1-T129, M1-Q128, M1-T127, M1-N126, M1-W125, M1-T124, M1-P123, M1-Q122, M1-G121, M1-I120, M1-S119, M1-I118, M1-S117, M1-T116, M1-R115, M1-T114, M1-D113, M1-L112, M1-Pill, M1-L110, M1-P109, M1-T108, M1-D107, M1-M106, M1-A105, M1-V104, M1-K103, M1-F102, M1-Y100, M1-H100, M1-T99, M1-D98, M1-A97, M1-Y96, M1-E95, M1-S94, M1-E93, M1-K92, M1-I91, M1-P90, M1-R89, M1-A88, M1-P87, M1-L86, M1-I85, M1-K84, M1-I83, M1-S82, M1-Q81, M1-W80, M1-T79, M1-E78, M1-E77, M1-M76, M1-R75, M1-L74, M1-E73, M1-P72, M1-D71, M1-D70, M1-Y69, M1-D68, M1-D67, M1-D66, M1-S65, M1-H64, M1-G63, M1-K62, M1-A61, M1-G60, M1-D59, M1-L58, M1-V57, M1-A56, M1-A55, M1-F54, M1-N53, M1-R52, M1-E51, M1-W50, M1-D49, M1-L48, M1-L47, M1-P46, M1-K45, M1-N44, M1-M43, M1-R42, M1-Q41, M1-Y40, M1-Q39, M1-G38, M1-T37, M1-A36, M1-S35, M1-N34, M1-I33, M1-R32, M1-P31, M1-W30, M1-S29, M1-R28, M1-N27, M1-K26, M1-P25, M1-L24, M1-S23, M1-F22, M1-N21, M1-Q20, M1-F19, M1-K18, M1-L17, M1-D16, M1-N15, M1-S14, M1-G13, M1-E12, M1-K11, M1-T10, M1-T9, M1-K8, and/or M1-R7 (of SEQ ID NO:4). Polynucleotide sequences encoding these polypeptides are also provided. These C-terminal MIST splice variant clone #7 deletion polypeptides are useful as immunogenic and/or antigenic epitopes as described elsewhere herein.

Alternatively, the preferred polypeptides of the present invention may comprise polypeptide sequences corresponding to, for example, internal regions of the MIST splice variant clone #7 polypeptide (e.g., any combination of both N- and C-terminal MIST splice variant clone #7 polypeptide deletions) of SEQ ID NO:4. For example, internal regions can be defined by the equation: amino acid "NX" to amino acid "CX", wherein "NX" refers to any N-terminal deletion polypeptide amino acid of MIST splice variant clone #7 (SEQ ID NO:4), and where "CX" refers to any C-terminal deletion polypeptide amino acid of MIST splice variant clone #7 (SEQ ID NO:4). Polynucleotides encoding these polypeptides are also provided. These polypeptides are useful as an immunogenic and/or antigenic epitope as described elsewhere herein.

In another preferred embodiment, the following N-terminal MIST splice variant clone #12 (SEQ ID NO:6) deletion polypeptides are encompassed by the present invention: M1-L353, E2-L353, E3-L353, T4-L353, W5-L353, Q6-L353, S7-L353, I8-L353, K9-L353, I10-L353, L11-L353, P12-L353, A13-L353, R14-L353, P15-L353, I16-L353, K17-L353, E18-L353, S19-L353, E20-L353, Y21-L353, A22-L353, D23-L353, T24-L353, H25-L353, Y26-L353, F27-L353, K28-L353, V29-L353, A30-L353, M31-L353, D32-L353, T33-L353, P34-L353, L35-L353, P36-L353, L37-L353, D38-L353, T39-L353, R40-L353, T41-L353, S42-L353, I43-L353, S44-L353, I45-L353, G46-L353, Q47-L353, P48-L353, T49-L353, W50-L353, N51-L353, T52-L353, Q53-L353, T54-L353, R55-L353, L56-L353, E57-L353, R58-L353, V59-L353, D60-L353, K61-L353, P62-L353,163-L353, S64-L353, K65-L353, D66-L353, V67-L353, R68-L353, S69-L353, Q70-L353, N71-L353,172-L353, K73-L353, G74-L353, D75-L353, A76-L353, S77-L353, V78-L353, R79-L353, K80-L353, N81-L353, K82-L353, 183-L353, P84-L353, L85-L353, P86-L353, P87-L353, P88-L353, R89-L353, P90-L353, L91-L353,192-L353, T93-L353, L94-L353, P95-L353, K96-L353, K97-L353, Y98-L353, Q99-L353, P100-L353, L101-L353, P102-L353, P103-L353, E104-L353, P105-L353, E106-L353, S107-L353, S108-L353, R109-L353, P110-L353, P111-L353, L112-L353, S113-L353, Q114-L353, R115-L353, H116-L353, T117-L353, F118-L353, P119-L353, E120-L353, V121-L353, Q122-L353, R123-L353, M124-L353, P125-L353, S126-L353, Q127-L353, I128-L353, S129-L353, L130-L353, R131-L353, D132-L353, L133-L353, S134-L353, E135-L353, V136-L353, L137-L353, E138-L353, A139-L353, E140-L353, K141-L353, V142-L353, P143-L353, H144-L353, N145-L353, Q146-L353, R147-L353, K148-L353, P149-L353, E150-L353, S151-L353, T152-L353, H153-L353, L154-L353, L155-L353, E156-L353, N157-L353, Q158-L353, N159-L353, T160-L353, Q161-L353, E162-L353, I163-L353, P164-L353, L165-L353, A166-L353, I167-L353, S168-L353, S169-L353, S170-L353, S171-L353, F172-L353, T173-L353, T174-L353, S175-L353, N176-L353, H177-L353, S178-L353, V179-L353, Q180-L353, N181-L353, R182-L353, D183-L353, H184-L353, R185-L353, G186-L353, G187-L353, M188-L353, Q189-L353, P190-L353, C191-L353, S192-L353, P193-L353, Q194-L353, R195-L353, C196-L353, Q197-L353, P198-L353, P199-L353, A200-L353, S201-L353, C202-L353, S203-L353, P204-L353, H205-L353, E206-L353, N207-L353, I208-L353, L209-L353, P210-L353, Y211-L353, K212-L353, Y213-L353, T214-L353, S215-L353, W216-L353, R217-L353, P218-L353, P219-L353, F220-L353, P221-L353, K222-L353, R223-L353, S224-L353, D225-L353, R226-L353, K227-L353, D228-L353, V229-L353, Q230-L353, H231-L353, N232-L353, E233-L353, W234-L353, Y235-L353, I236-L353, G237-L353, E238-L353, Y239-L353, S240-L353, R241-L353, Q242-L353, A243-L353, V244-L353, E245-L353, E246-L353, A247-L353, F248-L353, M249-L353, K250-L353, E251-L353, N252-L353, K253-L353, D254-L353, G255-L353, S256-L353, F257-L353, L258-L353, V259-L353, R260-L353, D261-L353, C262-L353, S263-L353, T264-L353, K265-L353, S266-L353, K267-L353, E268-L353, E269-L353, P270-L353, Y271-L353, V272-L353, L273-L353, A274-L353, V275-L353, F276-L353, Y277-L353, E278-L353, N279-L353, K280-L353, V281-L353, Y282-L353, N283-L353, V284-L353, K285-L353, I286-L353, R287-L353, F288-L353, L289-L353, E290-L353, R291-L353, N292-L353, Q293-L353, Q294-L353, F295-L353, A296-L353, L297-L353, G298-L353, T299-L353, G300-L353, L301-L353, R302-L353, G303-L353, D304-L353, E305-L353, K306-L353, F307-L353, D308-L353, S309-L353, V310-L353, E311-L353, D312-L353, I313-L353, I314-L353, E315-L353, H316-L353, Y317-L353, K318-L353, N319-L353, F320-L353, P321-L353, I322-L353, I323-L353, L324-L353, I325-L353, D326-L353, G327-L353, K328-L353, D329-L353, K330-L353, T331-L353, G332-L353, V333-L353, H334-L353, R335-L353, K336-L353, Q337-L353, C338-L353, H339-L353, L340-L353, T341-L353, Q342-L353, P343-L353, L344-L353, P345-L353, L346-L353, and/or T347-L353 (of SEQ ID NO:6). Polynucleotide sequences encoding these polypeptides are also provided. These N-terminal MIST splice variant clone #12 deletion polypeptides are useful as immunogenic and/or antigenic epitopes as described elsewhere herein.

In a further preferred embodiment, the following C-terminal MIST splice variant clone #12 (SEQ ID NO:6) deletion polypeptides are encompassed by the present invention: M1-L353, M1-P352, M1-L351, M1-L350, M1-H349, M1-R348, M1-T347, M1-L346, M1-P345, M1-L344, M1-P343, M1-Q342, M1-T341, M1-L340, M1-H339, M1-C338, M1-Q337, M1-K336, M1-R335, M1-H334, M1-V333, M1-G332, M1-T331, M1-K330, M1-D329, M1-K328, M1-G327, M1-D326, M1-I325, M1-L324, M1-I323, M1-I322, M1-P321, M1-F320, M1-N319, M1-K318, M1-Y317, M1-H316, M1-E315, M1-I314, M1-I313, M1-D312, M1-E311, M1-V310, M1-S309, M1-D308, M1-F307, M1-K306, M1-E305, M1-D304, M1-G303, M1-R302, M1-L301, M1-G300, M1-T299, M1-G298, M1-L297, M1-A296, M1-F295, M1-Q294, M1-Q293, M1-N292, M1-R291, M1-E290, M1-L289, M1-F288, M1-R287, M1-I286, M1-K285, M1-V284, M1-N283, M1-Y282, M1-V281, M1-K280, M1-N279, M1-E278, M1-Y277, M1-F276, M1-V275, M1-A274, M1-L273, M1-V272, M1-Y271, M1-P270, M1-E269, M1-E268, M1-K267, M1-S266, M1-K265, M1-T264, M1-S263, M1-C262, M1-D261, M1-R260, M1-V259, M1-L258, M1-F257, M1-S256, M1-G255, M1-D254, M1-K253, M1-N252, M1-E251, M1-K250, M1-M249, M1-F248, M1-A247, M1-E246, M1-E245, M1-V244, M1-A243, M1-Q242, M1-R241, M1-S240, M1-Y239, M1-E238, M1-G237, M1-I236, M1-Y235, M1-W234, M1-E233, M1-N232, M1-H231, M1-Q230, M1-V229, M1-D228, M1-K227, M1-R226, M1-D225, M1-S224, M1-R223, M1-K222, M1-P221, M1-F220, M1-P219, M1-P218, M1-R217, M1-W216, M1-S215, M1-T214, M1-Y213, M1-K212, M1-Y211, M1-P210, M1-L209, M1-I208, M1-N$_2$O$_7$, M1-E206, M1-H205, M1-P204, M1-S203, M1-C202, M1-S201, M1-A200, M1-P199, M1-P198, M1-Q197, M1-C196, M1-R195, M1-Q194, M1-P193, M1-S192, M1-C191, M1-P190, M1-Q189, M1-M188, M1-G187, M1-G186, M1-R185, M1-H184, M1-D183, M1-R182, M1-N181, M1-Q180, M1-V179, M1-S178, M1-H177, M1-N176, M1-S175, M1-T174, M1-T173, M1-F172, M1-S171, M1-S170, M1-S169, M1-S168, M1-I167, M1-A166, M1-L165, M1-P164, M1-I163, M1-E162, M1-Q161, M1-T160, M1-N159, M1-Q158, M1-N157, M1-E156, M1-L155, M1-L154, M1-H153, M1-T152, M1-S151, M1-E150, M1-P149, M1-K148, M1-R147, M1-Q146, M1-N145, M1-H144, M1-P143, M1-V142, M1-K141, M1-E140, M1-A139, M1-E138, M1-L137, M1-V136, M1-E135, M1-S134, M1-L133, M1-D132, M1-R131, M1-L130, M1-S129, M1-I128, M1-Q127, M1-S126, M1-P125, M1-M124, M1-R123, M1-Q122, M1-V121, M1-E120, M1-P119, M1-F118, M1-T117, M1-H116, M1-R115, M1-Q114, M1-S113, M1-L112, M1-P111, M1-P110, M1-R109, M1-S108, M1-S107, M1-E106, M1-P105, M1-E104, M1-P103, M1-P102, M1-L101, M1-P100, M1-Q99, M1-Y98, M1-K97, M1-K96, M1-P95, M1-L94, M1-T93, M1-I92, M1-L91, M1-P90, M1-R89, M1-P88, M1-P87, M1-P86, M1-L85, M1-P84, M1-I83, M1-K82, M1-N81, M1-K80, M1-R79, M1-V78, M1-S77, M1-A76, M1-D75, M1-G74, M1-K73, M1-I72, M1-N71, M1-Q70, M1-S69, M1-R68, M1-V67, M1-D66, M1-K65, M1-S64, M1-I63, M1-P62, M1-K61, M1-D60, M1-V59, M1-R58, M1-E57, M1-L56, M1-R55, M1-T54, M1-Q53, M1-T52, M1-N51, M1-W50, M1-T49, M1-P48, M1-Q47, M1-G46, M1-I45, M1-S44, M1-I43, M1-S42, M1-T41, M1-R40, M1-T39, M1-D38, M1-L37, M1-P36, M1-L35, M1-P34, M1-T33, M1-D32, M1-M31, M1-A30, M1-V29, M1-K28, M1-F27, M1-Y26, M1-H25, M1-T24, M1-D23, M1-A22, M1-Y21, M1-E20, M1-S19, M1-E18, M1-K17, M1-I16, M1-P15, M1-R14, M1-A13, M1-P12, M1-L11, M1-I10, M1-K9, M1-I8, and/or M1-S7 (of SEQ ID NO:6). Polynucleotide sequences encoding these polypeptides are also provided. These C-terminal MIST splice variant clone #12 deletion polypeptides are also useful as immunogenic and/or antigenic epitopes as described elsewhere herein.

Alternatively, the preferred polypeptides of the present invention may comprise polypeptide sequences corresponding to, for example, internal regions of the MIST splice variant clone #12 polypeptide (e.g., any combination of both N- and C-terminal MIST splice variant clone #12 polypeptide deletions) of SEQ ID NO:6. For example, internal regions could be defined by the equation: amino acid "NX" to amino acid "CX", wherein "NX" refers to any N-terminal deletion polypeptide amino acid of MIST splice variant clone #12 (SEQ ID NO:6), and where "CX" refers to any C-terminal deletion polypeptide amino acid of MIST splice variant clone #12 (SEQ ID NO:6). Polynucleotides encoding these polypeptides are also provided. These polypeptides are also useful as an immunogenic and/or antigenic epitope as described elsewhere herein.

Example 11

Use of Anti-MIST Antibodies to Detect MIST Expression

Anti-MIST mAb generation: To produce anti-MIST monoclonal antibodies (mAb), several poly-histidine (His) tagged MIST fusion proteins including: MIST full length (His-MIST-fl, residues 1-443), the proline-rich domain (His-MIST-PR, residues 160-320) and the SH2 domain (His-MIST-SH2, residues 320-443) (FIG. 6) were prepared. Mice (Balb/c) were immunized with the His-MIST-PR fusion protein (50 µg) and selected depending upon their serum activity against the His-MIST-PR protein in ELISA experiments. Anti-MIST mAbs were produced following standard procedures. One of the mAbs (#45) was reactive against MIST in both native (IP) and denatured (WB) conditions.

MIST protein expression and tyrosine phosphorylation analysis. The human leukemic B-cell lines Daudi (ATCC® Designation: CCL-213) and Raji (ATCC® Designation: CCL-86), the human leukemic T-cell lines CEM (ATCC® Designation: CCL-119) and Jurkat (ATCC® Designation: TIB-152), the Mast-cell lines P815 (mouse), (ATCC® Designation: TIB-64), RBL (rat) and HMC-1 (human) and the mouse monocyte cell line Raw were cultured in RPMI 1640 containing 10% heat-inactivated FCS, 100 U/ml penicillin and 100 µg/ml streptomycin. For MIST expression analysis, equivalent number of cells ($10^7$) were washed and lysed in 1 ml of lysis buffer containing 50 mM Tris, pH 7.5, 1% NP-40, 150 mM NaCl, 2 mM EGTA, 1 mM NaF, 1 mM sodium orthovanadate, plus Complete Protease Inhibitor Mixture (Boehringer Mannheim, Indianapolis, Ind.). Samples were centrifuged at 14,000 rpm for 2 minutes (to remove nuclei and other insoluble material). A 10 μl aliquot from each lysate was resuspended in 20 μl of Laemmli sample buffer (Biorad, Hercules Calif.), boiled for 5 minutes, analyzed by SDS-PAGE gradient (4-20% gels) under reducing conditions. Separated protein was subsequently transferred to polyvinylidene difluoride membranes (Immobilon-P, Millipore, Marlborough, Mass.). For MIST protein detection, membranes were blocked in 3% BSA and treated with the anti-MIST #45 monoclonal antibody (1 μg/ml) as a primary reagent, and anti-mouse linked to horseradish peroxidase (HRP) (Biosource International) as the secondary reagent.

For MIST tyrosine phosphorylation analysis, 107 RBL or HMC-1 mast cells were stimulated with pervanadate (1 μM sodium orthovanadate and 100 μM $H_2O_2$) at 37° C. for the indicated time periods. After stimulation, cells were lysed in 1 ml of lysis buffer (see above). Samples were centrifuged at 14,000 rpm for 2 minutes (to remove nuclei and other insoluble material); lysates were precleared twice with protein A SEPHAROSE® beads (Pharmacia Biotech) for 60 minutes at 4° C. and subjected to immunoprecipitation with the anti-MIST mAb #45. Immunoprecipitated proteins were washed once with 10% buffer lysis in PBS and twice with PBS alone.

After washing, immunoprecipitates were resuspended in 201 of Laemmli sample buffer (Biorad, Hercules Calif.), boiled for 5 minutes, and analyzed by SDS-PAGE on gradient 4-20% gels under reducing conditions. Separated proteins were subsequently transferred to polyvinylidene difluoride membranes (Immobilon-P, Millipore, Marlborough, Mass.). For phosphotyrosine analysis, blots were incubated with anti-phosphotyrosine mAb 4G10-HRP (Upstate Biotechnology, Inc.) at 0.1 μg/ml. Where indicated, blot stripping was carried out by membrane incubation in 62.5 mM Tris-HCl, pH 6.8, 2% SDS and 50 mM β-mercaptoethanol at room temperature for 60 minutes. For determination of the levels of MIST protein expression, membranes were blocked in 3% BSA and treated with the indicated anti-MIST #45 mAb as primary reagent, and anti-mouse linked to horseradish peroxidase (anti-mouse HRP) (Biosource International) as the secondary reagent. The binding of HRP was detected by ECL (Amersham, Buckinghamshire, England) and exposure to X-ray film.

Figure 15A:
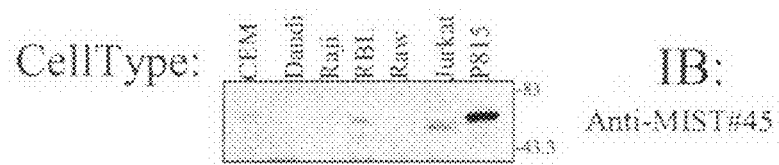
FIGS. 15A and 15B present the expression pattern and tyrosine phosphorylation of MIST.

Using the above-described procedures, a panel of mouse mAbs against the His-MIST-PR fusion protein (including residues 160-320) were generated. One of these mAbs, termed #45, was found to react specifically with the His-MIST-PR fusion protein and not with other non-related poly-His fusion proteins used as controls. To analyze the expression of the native MIST protein by Western blot (WB), a panel of mast, B, T and monocyte cells lines were evaluated using this mAb. As shown in FIG. 15A, MIST was specifically expressed only in mast cell lines (P815 and RBL).

In experiments to link MIST to the signal transduction pathway in mast cells, the ability of MIST to become tyrosine phosphorylated following cellular activation was assessed. To perform these experiments, two different MIST-expressing mast cell lines, i.e., human (HMC-1) mast cells and rat (RBL) mast cells, were stimulated with pervanadate, (an inhibitor of protein-tyrosine phosphatases that induces protein-tyrosine phosphorylation and cell activation (J. J. O'Shea et al, 1992, *Proc. Natl. Acad. Sci. USA,* 89(21):10306-10310), for different time periods.

Figure 15B:
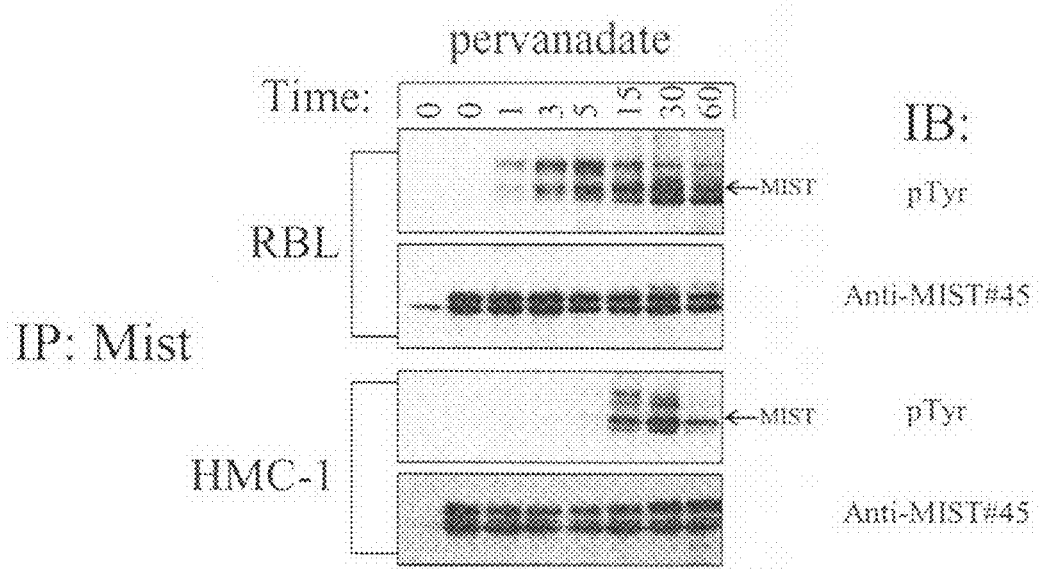

After the stimulation, cells were lysed and the MIST proteins were immunoprecipitated with the anti-MIST mAb #45 and probed with the anti-phosphotyrosine mAb, 4G10-HRP. As shown in FIG. 15B, phosphotyrosine-containing proteins were detected in the anti-MIST immunoprecipitates from the RBL and HMC-1 cell lines following pervanadate stimulation. In these two cell lines, the tyrosine phosphorylation of MIST (indicated by arrows) clearly increased following pervanadate stimulation. In addition, several unidentified tyrosine phosphorylated proteins also co-precipitated with MIST (FIG. 15B).

The data presented in this Example indicate that MIST is specifically expressed in mast cells and support the MIST protein's ability to function as a crucial signaling component for mast cell activation. In this regard, tyrosine phosphorylated BASH/SLP-65/BLNK, a B cell analogue of MIST, was recently reported to bind to the SH2 domain of Btk (a Tec family tyrosine kinase crucial for B cell activation through the phosphorylation and activation of PLCγ2) (D. Watanabe et al., 2001, *J. Biol. Chem.*, PMID: 11507089, PubMed). Without wishing to be bound by theory, and based on the results of the studies described herein, a functional and plausible role for the novel MIST protein is provided. Since following mast cell activation the MIST protein becomes tyrosine phosphorylated and Btk is critical for mast cell function, MIST may serve as a linker between associated protein tyrosine kinases (i.e. Btk) and downstream signaling molecules (e.g., PLCγ2), thus regulating degranulation and cytokine production in mast cells.

The contents of all patents, patent applications, published PCT applications and articles, books, references, reference manuals and abstracts cited herein are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. An isolated antibody or fragment thereof selected from the group consisting of:
   (a) an isolated antibody or fragment thereof that binds to the polypeptide consisting of amino acids 1 to 443 of SEQ ID NO:2; and
   (b) an isolated antibody or fragment thereof that binds to the polypeptide consisting of amino acids 2 to 443 of SEQ ID NO:2.

2. The isolated antibody or fragment thereof of claim 1, wherein said antibody is (a).

3. The isolated antibody or fragment thereof of claim 1, wherein said antibody is (b).

4. The isolated antibody or fragment thereof according to claim 1 which is polyclonal.

5. The isolated antibody or fragment thereof according to claim 1 which is monoclonal.

6. The isolated antibody or fragment thereof according to claim 1 which is chimeric.

7. The isolated antibody or fragment thereof according to claim 1 which is humanized.

8. The isolated antibody or fragment thereof according to claim 1 which is mammalian.

9. The isolated antibody or fragment thereof according to claim 1 which is human.

10. A hybridoma cell which produces the isolated antibody or fragment thereof according to claim 5.

11. The isolated antibody or fragment thereof of claim 1, wherein the fragment is selected from the group consisting of a) a Fab fragment; b) a F(ab')2 fragment; c) a Fv fragment; and d) a single chain fragment.

12. The isolated antibody or fragment thereof of claim 1 further comprising a detectable substance coupled to said antibody.

13. The isolated antibody or fragment thereof of claim 12, wherein said detectable substance is selected from the group consisting of: a) an enzyme; b) a fluorescent label; c) a radioisotope; and d) chemiluminescent label.

14. The isolated antibody or fragment thereof of claim 12, which specifically binds to said polypeptide in an ELISA.

15. The isolated antibody or fragment thereof of claim 12, which specifically binds to said polypeptide in a competitive-binding assay.

16. The isolated antibody or fragment thereof of claim 12, which specifically binds to said polypeptide in a radioimmunoassay.

17. The isolated antibody or fragment thereof of claim 12, which specifically binds to said polypeptide in a FACS.

18. A kit for detecting a polypeptide consisting of amino acids 1 to 443 of SEQ ID NO:2 comprising:
   (a) the isolated antibody of claim 1; and
   (b) at least one component to detect binding of the isolated antibody to said polypeptide.

19. An isolated antibody obtained from an animal that has been immunized with a polypeptide fragment of SEQ ID NO:2 as encoded by the cDNA of hMIST clone #8 contained in ATCC deposit No. PTA-2981, wherein said antibody binds to an antigenic epitope-bearing polypeptide fragment of said polypeptide.

20. An isolated antibody or fragment thereof that binds to a polypeptide consisting of at least 352 contiguous amino acids of SEQ ID NO:2, wherein said polypeptide binds to Grb2, Vav, Lat, c-Cbl, or SLP-76.

21. An isolated antibody or fragment thereof that binds to a polypeptide consisting of 50 contiguous amino acids of SEQ ID NO:2, wherein said polypeptide binds to Grb2, Vav, Lat, c-Cbl, or SLP-76.

22. An isolated antibody or fragment thereof that binds to a fragment of a polypeptide encoded by the cDNA of hMIST clone #8 contained in ATCC deposit No. PTA-2981.

23. An isolated antibody or fragment thereof selected from the group consisting of:
  (a) an isolated antibody or fragment thereof that binds to the polypeptide consisting of amino acids 83 to 443 of SEQ ID NO:2;
  (b) an isolated antibody or fragment thereof that binds to the polypeptide consisting of amino acids 1 to 323 of SEQ ID NO:2;
  (c) an isolated antibody or fragment thereof that binds to the polypeptide consisting of amino acids 160 to 320 of SEQ ID NO:2;
  (d) an isolated antibody or fragment thereof that binds to the polypeptide consisting of amino acids 320 to 443 of SEQ ID NO:2;
  (e) an isolated antibody or fragment thereof that binds to the polypeptide consisting of amino acids 324 to 407 of SEQ ID NO:2; and
  (f) an isolated antibody or fragment thereof that binds to the polypeptide consisting of amino acids 1 to 320 of SEQ ID NO:2;
wherein said polypeptide binds to Grb2, Vav, Lat, c-Cbl, or SLP-76.

24. An isolated antibody or fragment thereof that binds to the polypeptide consisting of SEQ ID NO:2 containing a single amino acid substitution, wherein said polypeptide binds to Grb2, Vav, Lat, c-Cbl, or SLP-76.

25. An isolated antibody or fragment thereof that binds to the polypeptide according to claim 1, 4, 5, 6, 7, 8, 9, 12, 19, 20, 21, 22, 23, or 24, wherein said polypeptide is phosphorylated.

* * * * *